United States Patent
Rosenblum et al.

(10) Patent No.: US 10,323,239 B2
(45) Date of Patent: *Jun. 18, 2019

(54) SERINE PROTEASE MOLECULES AND THERAPIES

(71) Applicant: Research Development Foundation, Carson City, NV (US)

(72) Inventors: Michael G. Rosenblum, Sugar Land, TX (US); Khalid Amanali Mohamedali, Houston, TX (US); Lawrence H. Cheung, Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/916,743

(22) Filed: Mar. 9, 2018

(65) Prior Publication Data

US 2018/0201918 A1 Jul. 19, 2018

Related U.S. Application Data

(62) Division of application No. 14/322,485, filed on Jul. 2, 2014, now Pat. No. 9,951,325, which is a division of application No. 14/046,211, filed on Oct. 4, 2013, now Pat. No. 9,096,840.

(60) Provisional application No. 61/622,216, filed on Feb. 7, 2013, provisional application No. 61/762,173, filed on Feb. 7, 2013, provisional application No. 61/709,763, filed on Oct. 4, 2012.

(51) Int. Cl.
| | |
|---|---|
| *C12N 9/64* | (2006.01) |
| *C07K 14/00* | (2006.01) |
| *C07K 14/47* | (2006.01) |
| *C07K 16/00* | (2006.01) |
| *C07K 16/28* | (2006.01) |
| *C07K 16/30* | (2006.01) |

(52) U.S. Cl.
CPC .......... *C12N 9/6467* (2013.01); *C07K 14/001* (2013.01); *C07K 14/4747* (2013.01); *C07K 16/00* (2013.01); *C07K 16/2863* (2013.01); *C07K 16/30* (2013.01); *C12N 9/6424* (2013.01); *C07K 2319/00* (2013.01); *C07K 2319/01* (2013.01); *C07K 2319/03* (2013.01); *C07K 2319/10* (2013.01); *C07K 2319/30* (2013.01); *C07K 2319/33* (2013.01); *C07K 2319/50* (2013.01); *C07K 2319/55* (2013.01)

(58) Field of Classification Search
CPC combination set(s) only.
See application file for complete search history.

(56) References Cited

U.S. PATENT DOCUMENTS

| | | | |
|---|---|---|---|
| 5,624,827 | A | 4/1997 | Beattie |
| 7,083,957 | B2 | 8/2006 | Rosenblum |
| 7,759,091 | B2 | 7/2010 | Rosenblum |
| 8,043,831 | B2 | 10/2011 | Rosenblum |
| 8,530,225 | B2 | 9/2013 | Rosenblum |
| 2010/0069303 | A1 | 3/2010 | Rosenblum |

FOREIGN PATENT DOCUMENTS

| | | |
|---|---|---|
| CN | 101 684 159 | 3/2010 |
| EP | 1378520 | 1/2004 |
| EP | 1736484 | 12/2006 |
| EP | 2647707 | 9/2018 |
| JP | 2004-535202 | 11/2004 |
| JP | 2005-501517 | 1/2005 |
| JP | 2007-535915 | 12/2007 |
| JP | 2008-526889 | 7/2008 |
| WO | WO 2003/007889 | 1/2003 |
| WO | WO 2004/094478 | 11/2004 |
| WO | WO 2004/108074 | 12/2004 |
| WO | WO 2006/074451 | 7/2006 |
| WO | WO 2007/146968 | 12/2007 |
| WO | WO 2012-073985 | 6/2012 |
| WO | WO 2013/041659 | 3/2013 |

OTHER PUBLICATIONS

Dälken et al., "Targeted induction of apoptosis by chimeric granzyme B fusion proteins carrying antibody and growth factor domains for cell recognition," *Cell Death Differ.*, 13(4):576-585, 2006.
Office Action issued in Japanese Application No. 2017-102733, dated May 2, 2018, and English translation thereof.
"Human GrBLG fusion protein, SEQ:11", EBI accession No. GSP:AYG19884, dated Mar. 31, 2010.
"Subname: Full=Uncharacterized protine", EBI accession No. UNITPROT:H2NKX9, dated Mar. 21, 2012.
Cao et al., "Construction and characterization of novel, completely human serine protease therapeutics targeting Her2/neu", *Molecular Cancer Therapeutics*, 21(6): 979-991, 2013.

(Continued)

*Primary Examiner* — Kagnew H Gebreyesus
(74) *Attorney, Agent, or Firm* — Parker Highlander PLLC

(57) ABSTRACT

Cell-targeted serine protease constructs are provided. Such constructs can be used in methods for targeted cell killing such as for treatment cell of proliferative diseases (e.g., cancer). In some aspects, recombinant serine proteases, such as Granzyme B polypeptides, are provided that exhibit improved stability and cell toxicity. Methods and compositions for treating lapatinib or trastuzumab-resistant cancers are also provided.

16 Claims, 33 Drawing Sheets

Specification includes a Sequence Listing.

(56) References Cited

OTHER PUBLICATIONS

Dälken et al., "Maltose-binding protein enhances secretion of recombinant human granzyme B accompanied by in vivo processing of a precursor MBP fusion protein", *PLoS One*, 5(12): E14404-1, 2010.

Harris et al., "Definition of redesign of the extended substrate specificity of granzyme B", *The Journal of Biological Chemistry*, 273(42):27364-27373, 1998.

Jabulowsky et al., "Surface charge-modification prevents sequestration and enhances tumor-cell specificity of a recombinant granzyme B-TGFα fusion protein", *Bioconjugate Chemistry*, 23(8): 1567-1576, 2012.

Joeckel and Bird, "Are all granzymes cytotoxic in vivo?", *Biological Chemistry*, 395(2): 181-202, 2014.

Liu et al., "Targeted delivery of human pro-apoptotic enzymes to tumor cells: In vitro studies describing a novel class of recombinant highly cytotoxic agents," *Molecular Cancer Therapeutics*, 2(12):1341-1350, 2003.

Losasso et al., "Design of human granzyme B variants resistant to serpin B9", *Proteins: Structure, Function, and Bioinformatics*, 80(11): 2514-2522, 2012.

Mabry et al., "Engineering of stable bispecific antibodies targeting IL-17A and IL-23," *Protein Engineering, Design & Selection*, 23(3):115-127, 2010.

Menzel et al., "Human antibody RNase fusion protein targeting CD30+ lymphomas", *Blood*, 111(7): 3830-3837, 2008.

Office Communication issued in U.S. Appl. No. 14/046,211, dated May 2, 2014.

PCT International Search Report and Written Opinion, issued in International Application No. PCT/US2013/063402, dated Apr. 4, 2014.

PCT Invitation to Pay Additional Fees, issued in International Application No. PCT/US2013/063402, dated Jan. 8, 2014.

Rosenblum et al., "Development of novel, highly cytotoxic fusion constructs containing granzyme B: unique mechanisms and functions", *Current Pharmaceutical Design*, 15(23): 2676-2692, 2009.

Rotonda et al., "The three-dimensional structure of human granzyme B compared to caspase-3, key mediators of cell death with cleavage specificity for aspartic acid in P1", *Chemistry and Biology*, 8(4):357-368, 2001.

Schiffer et al., "Efficacy of an adapted granzyme B-based anti-CD30 cytolytic fusion protein against PI-9-positive classical Hodgkin lymphoma cells in a murine model", *Blood Cancer J.*, 3: e106, 2013.

Schiffer et al., "Granzyme M as a novel effector molecule for human cytolytic fusion proteins: CD64-specific cytotoxicity of Gm-H22(scFv) against leukemic cells", *Cancer Letters*, 341(2): 178-85, 2013.

Shan et al., "Characterization of scFv-Ig Constructs Using Linker Peptides of Varying Lengths Generated from the Anti-CD20 mAb 1F5J," *Immunol.*, 162:6589-6595, 1999.

Shi et al, "Efficient growth inhibition of ErbB2—overexpressing tumor cells by anti-ErbB2 ScFv-Fc-IL-2 fusion protein in vitro and in vivo", *Acta Pharmacologica Sinica*, 28(10): 1611-1620, 2007.

Stahnke et al., "Granzyme B-H22 (scFv), a human immunotoxin targeting CD64 in acute myeloid leukemia of monocytic subtypes," *Mol. Cancer Ther.*, 7(9):2924-2934, 2008.

Weidle et al., "Fully human targeted cytotoxic fusion proteins: new anticancer agents on the horizon", *Cancer Genomics and Proteomics*, 9: 119-134, 2012.

Wowk, "Cytotoxic activity of the lymphocyte toxin granzyme B," *Microbes Infect.*, 6:752-758, 2004.

Zhang et al., "HER2-targeting recombinant protein with truncated *pseudomonas* exotoxin: a translocation domain efficiently kills breast cancer cells", *Cancer Biology*, 7(8): 1226-1231, 2008.

Zhou et al., "Development and characterization of a potent immunoconjugate targeting the Fn14 receptor on solid tumor cells", *Molecular Cancer Therapeutics*, 10: 1276-1288, 2011.

Office Action issued in Japanese Application No. 2017-102733, dated Jan. 7, 2019, and English translation thereof.

```
Gzm B    1  IIGGHEAKPHSRPYMAVLMIWDQKSLKRCGGFLIRDDFVLTAAHCWG----SSINVTLG        55
Gzm A    1  IIGGNEVTPHSRPYMVLLSLD----RKTICAGALIAKDWVLTAAHCNLN----KRSQVILG    53
Gzm H    1  IIGGHEAKPHSRPYMAFVQFLQEKSRKRCGGILVRKDFVLTAAHCQG----SSINVTLG      55
Gzm K    1  IIGGKEVSPHSRPFMASIQYG---GHHVCGGVLIDPQWVLTAAHCQYRFTKGQSPTVVLG     57
Gzm M    1  IIGGREVTPHSRPYMASLQRN----GSHLCGGVLVHPKWVLTAAHCLAQRM--AQLRLVLG    55
            ****.*     *** ** :         ..      ::*******          ::*

Gzm B   56  AHNIKEQEPTQQFIPVKRPIPHPAYNPKN-FSNDIMLLQLERKAKRTRAVQPLRLPSNKA   114
Gzm A   54  AHSITREEPTKQIMLVKKEFPYPCYDPAT-REGDLKLLQLMEKAKINKYVTILHLPKKGD  112
Gzm H   56  AHNIKEQERTQQFIPVKRPIPHPAYNPKN-FSNDIMLLQLERKAKWTTAVRPLRLPSSKA  114
Gzm K   58  AHSLSKNEASKQTLEIKKFIPFSRVTSDP-QSNDIMLVKLQTAAKLNKHVKMLHIRSK-T  115
Gzm M   56  LHTLDSP----GLTFHIKAAIQHPRYKPVPALENDLALLQLDGKVKPSRTIRPLALPSKRQ 112
               :  .       .:                 *: .              *.

Gzm B  115  QVKPGQTCSVAGWGQTAP-LGKHSHTLQEVKMTVQEDRKCESDLRHYYDST----IELCVG  170
Gzm A  113  DVKPGTMCQVAGWGRTHN-SASWSDTLREVNITIIDRKVCNDRNHYNFNPVIGMNMVCAG  171
Gzm H  115  QVKPGQLCSVAGWGYVS--MSTLATTLQEVLLTQKDCQCERLFHGNYSRA---TEICVG   169
Gzm K  116  SLRSGTKCKVTGWGATDPDSLRPSDTLREVTVTVLSRKLCNSQSYYNGDPFITKDMVCAG  175
Gzm M  113  VVAAGTRCSMAGWGLTHQ-GGRLSRVLRELDLQVLDTRMCNNSRFWNGS--LSPSMVCLA  169
                . * . ***                  :   :. *            .   :*.

Gzm B  171  DPEIKKTSFKGDSGGPLVCNK--VAQGIVSYGRN--NG--MPPRACTKVS-SFVHWIKKT  223
Gzm A  172  SLRGGRDSCNGDSGGPLLCEG--VFRGVTSFGLENKCGDPRGPGVYILLSKKHLNWIIMT  229
Gzm H  170  DPKKTQTGFKGDSGGPLVCKD--VAQGILSYGNK--KG--TPPGVYIKVS-HFLPWIKRT  222
Gzm K  176  DAKGQKDSCKGDSGGPLICKG--VFHAIVSGG--HECGVATKPGIYTLLTKKYQTWIKSN  231
Gzm M  170  ADSKDQAPCKGDSGGPLVCGGKGRVLARVLSFSSR-VCTDIFKPPVATAVA-PYVSWIRKV  227
                    ****** :*      .   :                                 *

Gzm B  224  MKRY---        227
Gzm A  230  IKGAV---       234
Gzm H  223  MKRL---        226
Gzm K  232  LVPPHTN        238
Gzm M  228  TGRSA---       232
```

FIG. 1B

| | | | |
|---|---|---|---|
| Granzyme B | 1 | IIGGHEAKPHSRPYMAYLMIWDQKS-LKRCGGFLIRDDFVLTAAHCWG-----SSINVTLG | 55 |
| Cathepsin G | 1 | IIGGRESRPHSRPYMAYLQIQSPAG-QSRCGGFLVREDFVLTAAHCWG-----SNINVTLG | 55 |
| Chymase | 1 | IIGGTECKPHSRPYMAYLEIVTSNGPSKFCGGFLIRRNFVLTAAHCAG-----RSITVTLG | 56 |
| Myeloblastin | 1 | IVGGHEAQPHSRPYMASLQMRGNPG-SHFCGGTLIHPSFVLTAAHCLRDIPQRLVNVVLG | 59 |
| Kallikrein-14 | 1 | IIGGHTCTRSSQPWQAALLAGP--RRRFLCGGALLSGQWVITAAHCGR-----PILQVALG | 54 |
| Complement factor D | 1 | ILGGREAFAHARPYMASVQLNG-----AHLCGGVLVAEQWVLSAAHCLEDAADGKVQVLLG | 56 |
| PRSS3 protein | 1 | IVGGYTCEENSLPYQVSLNSG-----SHFCGGSLISEQWVVSAAHCYK-----TRIQVRLG | 51 |
| Trypsin-1 | 1 | IVGGYNCEENSVPYQVSLNSG-----YHFCGGSLINEQWVVSAGHCYK-----SRIQVRLG | 51 |
| Serine protease 57 | 1 | IIGGHEVTPHSRPYMASVRFGG-----QHHCGGFLLRARWVVSAAHCFSHRDLRTGLVVLG | 56 |
| PRSS1 protein | 1 | IIGGHEVTPHSRPYMASVRFGG-----QHHCGGFLLRARWVVSAAHCFSHRDLRTGLVVLG | 56 |
| | | *** *  *  :**  * ::*:  **:*:** | |
| Granzyme B | 56 | AHNIKEQEPTQQFIPVKRPIPHPAYNPKNFSNDIMLLQLERKAKRTRAVQPLRLP-SNKA | 114 |
| Cathepsin G | 56 | AHNIQRRENTQQHITARRAIRHPQYNQRTIQNDIMLLQLSRRVRRNRVNPVALP-RAQE | 114 |
| Chymase | 57 | AHNITEEDTWQKLEVIKQFRHPKYNTSTLHHDIMLLKLKEKASLTLAVGTLPFP-SQFN | 115 |
| Myeloblastin | 60 | AHNVRTQEPTQQHFSVAQVFL-NNYDAENKLNDVLLIQLSSPANLSASVATVQLP-QQDQ | 117 |
| Kallikrein-14 | 55 | KHNLRRWEATQQVLRVVRQVTHPNYNSRTHDNDIMLLQLQQPARIGRAVRPIEVT----QA | 111 |
| Complement factor D | 57 | AHSLSQPEPSKRLYDVLRAVPHPDSQPDTIDHDLLLLQLSEKATLGPAVRPLP-WQRVDR | 115 |
| PRSS3 protein | 52 | EHNIKVLEGNEQFINAAKIIRHPQYDRKTLNNDIMLIKLSSRAVINARVSTISLP---TA | 108 |
| Trypsin-1 | 52 | EHNIEVLEGNEQFINAAKIIRHPQYDRKTLNNDIMLIKLSSRAVINARVSTISLP---TA | 108 |
| Serine protease 57 | 57 | AHVLSTAEPTQQVFGIDALTTHPDYHPMTHANDICLLRLNGSAVLGPAVGLLRPPGRRAR | 116 |
| PRSS1 protein | 57 | AHVLSTAEPTQQVFGIDALTTHPDYHPMTHANDICLLRLNGSAVLGPAVGLLRLPGRRAR | 116 |
| | | * :  . :  :  .  * | |
| Granzyme B | 115 | QVKPGQTCSVAGWGQTA-PLGKHSHTLQEVKMTVQEDRKCESDLRHYYDST-IELCVG-D | 171 |
| Cathepsin G | 115 | GLRPGTLCTVAGWGRVS--MRRGTDTLREVQLRVQRDRQCLRIFG-SYDPR-RQICVG-D | 169 |
| Chymase | 116 | FVPPGRMCRVAGWGRTG-VLKPGSDTLQEVKIRLMDPQACSHFR---DFDHN-LQLCVG-N | 170 |
| Myeloblastin | 118 | PVPHGTQCLAMGWGRVG-AHDPPAQVLQELNVTVVT------FFCRP-HNICTF-V | 164 |
| Kallikrein-14 | 112 | CASPGTSCRVSGWGTISSPIARYPASLQCVNINISPDEVCQKAY---PRTITPGMVCAG-V | 168 |
| Complement factor D | 116 | DVAPGTLCDVAGWGIVN--HAGRRPDSLQHVLLPVLDRATCNRRTHHDGAITERLMCA--- | 171 |

FIG. 1C

```
PRSS3 protein        109 PPATGTKCLISGWGNTASSGADYPDELQCLDAPVLSQAKCEASY--PGKITSNMFCVG-F 165
Trypsin-1            109 PPATGTKCLISGWGNTASSGADYPDELQCLDAPVLSQAKCEASY--PGKITSNMFCVG-F 165
Serine protease 57   117 PPTAGTRCRVAGWGFVS-DFEELPPGLMEAKVRVLDPDVCNSSW--KGHLTLTMLCTRSG 173
PRSSL1 protein       117 PPTAGTRCRVAGWGFVS-DFEELPPGLMEAKVRVLDPDVFNSSW--KGHLTLTMLCTRSG 173
                         *  *:* :*::****..  *:: *.*:*.*:: :*  :**::*    * :*: :* ..

Granzyme B           172 PEIKKTSFKGDSGGPLVCNKVAQGIVS----YGRNNGMPPRACTKVSSFVHWIKKTMKRY- 227
Cathepsin G          170 RRERKAAFKGDSGGPLLCNNVAHGIVS----YGKSSGVPPEVFTRVSSFLPWIRTTMRSEK 226
Chymase              171 PRKTKSAFKGDSGGPLLCAGVAQGIVS----YGRSDAKPPAVFTRISHYRPWINQILQAN- 226
Myeloblastin         165 PRRKAGICFGDSGGPLICDGIIQGIDSFVIWGCATRLFPDFFTRVALYVDWIRSTLRRVE- 224
Kallikrein-14        169 PQGGKDSCQGDSGGPLVCRGQLQGLVSWGMERCALPGYPGVYTNLCKYRSWIEETMRDK-- 227
Complement factor D  172 ESNRRDSCKGDSGGPLVCGGVLEGVTSGSRVCGNRKKPGIYTRVASYAAWIDSVLA----- 228
PRSS3 protein        166 LEGGKDSCQGDSGGPVVCNGQLQGVSWGD-GCAQKNKPGVYTKVYNYVKWIKNTIAANS 224
Trypsin-1            166 LEGGKDSCQGDSGGPVVCNGQLQGVSWGD-GCAQKNKPGVYTKVYNYVKWIKNTIAANS 224
Serine protease 57   174 DSHRRGFCSADSGGPLVCRNRAHGLVSFSGLWCGDPKTPDVYTQVSAFVAMIWDVVRSS 233
PRSSL1 protein       174 DSHRRGFCSADSGGPLVCRNRAHGLVSFSGLWCGDPKTPDVYTQVSAFVAMIWDVVRSS 233
                             . ****:.*    *: .  :   ::    *      *  ::     ::

Granzyme B           228 ------------- 227
Cathepsin G          227 LLDQMETPL---- 235
Chymase              227 ------------- 226
Myeloblastin         225 AKGRP-------- 229
Kallikrein-14        228 ------------- 227
Complement factor D  229 ------------- 228
PRSS3 protein        225 ------------- 224
Trypsin-1            225 ------------- 224
Serine protease 57   234 PQPGPLPGTTRPPGEAA 250
PRSSL1 protein       234 PQPGPLPGTTRPPGEAA 250
```

FIG. 1C
(Cont'd)

| | | | | | |
|---|---|---|---|---|---|
| (36) | GrB | SSG | CCP | INF7 | ZME(VL-VH) | pSECTag-GrB-Ad-INF7-ZME(WAd) |
| (37) | GrB(d1,N1) | SSG | CCP | INF7 | ZME(VL-VH) | pSECTag-d1N1-GrB-Ad-INF7-ZME (dNW) |
| (38) | GrB(d2,N1) | SSG | CCP | INF7 | ZME(VL-VH) | pSECTag-d2N1-GrB-Ad-INF7-ZME (d2NW) |
| (39) | GrB(d2,K) | SSG | CCP | INF7 | ZME(VL-VH) | pSECTag-d2K-GrB-Ad-INF7-ZME (d2KW) |
| (40) | GrB(d2,K,A) | SSG | CCP | INF7 | ZME(VL-VH) | pSECTag-d2KA-GrB-Ad-INF7-ZME (d2KAW) |
| (41) | GrB(K,A) | SSG | CCP | INF7 | ZME(VL-VH) | pSECTag-KA-GrB-Ad-INF7-ZME (KAW) |
| (42) | GrB | SSG | CCP | H5W | ZME(VL-VH) | pSECTag-d1N1-GrB-Ad-H5W-ZME (H5W) |
| (43

SL: wild type
SL-1: deglycosylation site (d1) (N51S)
SL-2: deglycosylation site (d2) (N84A)
SL-3: deglycosylation sites (d1+d2)

|            | A.A. | M.W.    | P.I. |
|------------|------|---------|------|
| GrB/4D5    | 502  | 53932.4 | 9.56 |
| GrB/4D5/26 | 546  | 57900.6 | 9.23 |

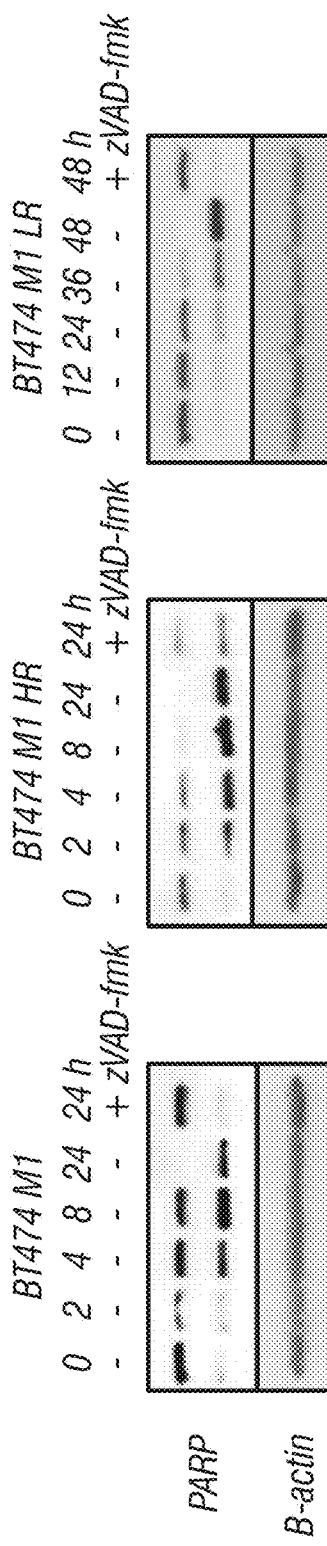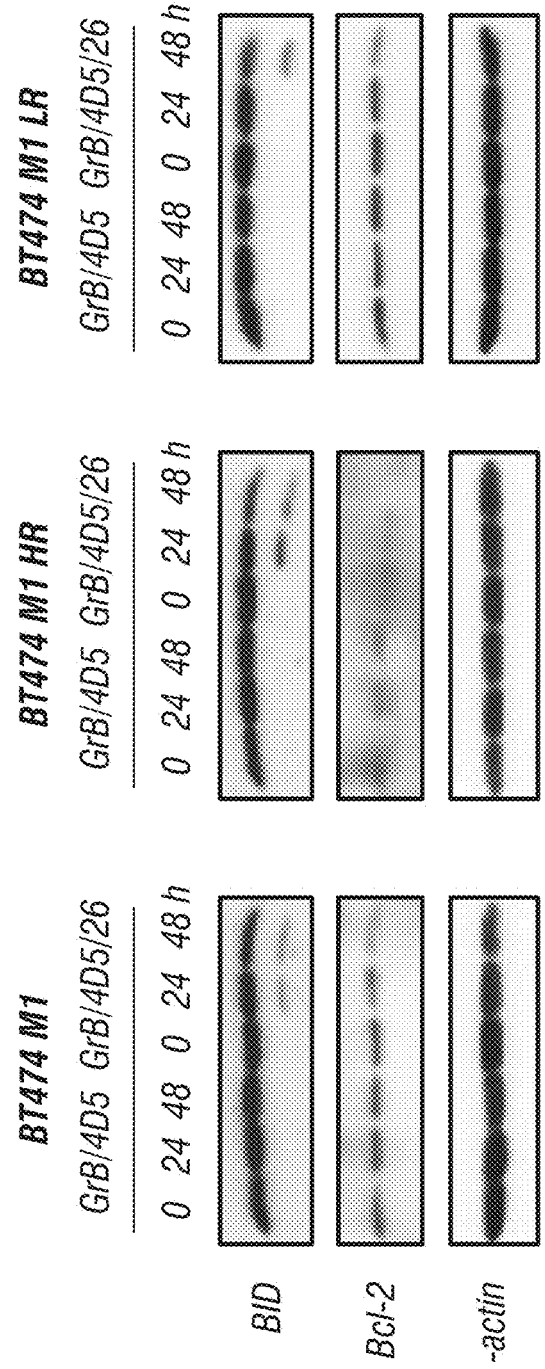
FIG. 7C
FIG. 8A

SEQUENCE LISTING

```
<160> NUMBER OF SEQ ID NOS: 58

<210> SEQ ID NO 1
<211> LENGTH: 227
<212> TYPE: PRT
<213> ORGANISM: Homo sapiens

<400> SEQUENCE: 1

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
                20                  25                  30

Leu Ile Arg Asp Asp Phe Val Leu Thr Ala Ala His Cys Trp Gly Ser
            35                  40                  45

Ser Ile Asn Val Thr Leu Gly Ala His Asn Ile Lys Glu Gln Glu Pro
        50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
                100                 105                 110

Lys Ala Gln Val Lys Pro Gly Gln Thr Cys Ser Val Ala Gly Trp Gly
            115                 120                 125

Gln Thr Ala Pro Leu Gly Lys His Ser His Thr Leu Gln Glu Val Lys
        130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
                180                 185                 190

Ala Gln Gly Ile Val Ser Tyr Gly Arg Asn Asn Gly Met Pro Pro Arg
            195                 200                 205

Ala Cys Thr Lys Val Ser Ser Phe Val His Trp Ile Lys Lys Thr Met
        210                 215                 220

Lys Arg Tyr
225

<210> SEQ ID NO 2
<211> LENGTH: 227
<212> TYPE: PRT
<213> ORGANISM: Pan troglodytes

<400> SEQUENCE: 2

Ile Ile Gly Gly His Glu Ala Lys Pro His Ser Arg Pro Tyr Met Ala
1               5                   10                  15
```

```
Tyr Leu Met Ile Trp Asp Gln Lys Thr Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Pro
50                      55                  60

Thr Gln Gln Phe Ile Pro Val Lys Arg Pro Ile Pro His Pro Ala Tyr
65                  70                  75                  80

Asn Pro Lys Asn Tyr Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Val Cys Ser Val Ala Gly Trp Gly
        115                 120                 125

Gln Thr Ala Pro Leu Gly Lys His Ser His Thr Leu Gln Glu Val Lys
130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
210                 215                 220

Lys Arg His
225

<210> SEQ ID NO 3
<211> LENGTH: 227
<212> TYPE: PRT
<213> ORGANISM: Pan paniscus

<400> SEQUENCE: 3

Ile Ile Gly Gly His Glu Ala Lys Pro His Ser Arg Pro Tyr Met Ala
1               5                   10                  15

Tyr Leu Met Ile Trp Asp Gln Lys Thr Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Pro
50                      55                  60

Thr Gln Gln Phe Ile Pro Val Lys Arg Pro Ile Pro His Pro Ala Tyr
65                  70                  75                  80

Asn Pro Lys Asn Tyr Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Ala Cys Ser Val Ala Gly Trp Gly
        115                 120                 125

Gln Thr Ala Pro Leu Gly Lys His Ser His Thr Leu Gln Glu Val Lys
130                 135                 140

Met Thr Val Gln Glu Asp Arg Lys Cys Glu Ser Asp Leu Arg His Tyr
145                 150                 155                 160
```

Tyr Asp Ser Thr Ile Glu Leu Cys Val Gly Asp Pro Glu Ile Lys Lys
            165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg His
225

<210> SEQ ID NO 4
<211> LENGTH: 227
<212> TYPE: PRT
<213> ORGANISM: Pongo abelii

<400> SEQUENCE: 4

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Glu Asp Phe Val Leu Thr Ala Ala His Cys Trp Gly Ser
        35                  40                  45

Ser Ile Asn Val Thr Leu Gly Ala His Asn Ile Lys Glu Gln Glu Gln
    50                  55                  60

Thr Gln Gln Leu Ile Pro Val Lys Arg Ala Val Arg His Pro Ala Tyr
65                  70                  75                  80

Asn Pro Lys Asn Phe Ser Asn Asp Ile Met Leu Leu Gln Leu Glu Lys
                85                  90                  95

Lys Ala Lys Arg Thr Thr Ala Val Gln Pro Leu Arg Leu Pro Ser Asn
            100                 105                 110

Lys Ala Gln Val Lys Pro Gly Gln Ala Cys Ser Val Ala Gly Trp Gly
        115                 120                 125

Gln Thr Ala Pro Thr Gly Lys Tyr Ser His Thr Leu Gln Glu Val Glu
130                 135                 140

Met Thr Val Gln Glu Asp Arg Lys Cys Lys Ser Asp Leu Arg His Tyr
145                 150                 155                 160

Tyr Asp Ser Thr Ile Glu Leu Cys Val Gly Asp Pro Glu Ile Lys Lys
            165                 170                 175

Ala Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Val Cys Thr Lys Val Ser Ser Phe Val His Trp Ile Lys Lys Thr Met
    210                 215                 220

Lys Arg His
225

<210> SEQ ID NO 5
<211> LENGTH: 227
<212> TYPE: PRT
<213> ORGANISM: Macaca nemestrina

<400> SEQUENCE: 5

Ile Ile Gly Gly His Glu Ala Lys Pro His Ser Arg Pro Tyr Met Ala
1               5                   10                  15

```
Tyr Leu Met Ile Trp Asp Gln Met Ser Leu Lys Arg Cys Gly Gly Phe
             20                  25                  30
Leu Ile Arg Glu Asp Phe Val Leu Thr Ala Ala His Cys Trp Gly Ser
         35                  40                  45
Ser Ile Asn Val Thr Leu Gly Ala His Asn Ile Lys Glu Gln Glu Arg
 50                  55                  60
Thr Gln Gln Ile Ile Pro Val Lys Arg Ala Ile Pro His Pro Ala Tyr
 65                  70                  75                  80
Asn Pro Glu Asn Phe Ser Asn Asp Ile Met Leu Leu Gln Leu Glu Arg
                 85                  90                  95
Lys Ala Lys Arg Thr Thr Ala Val Gln Pro Leu Arg Leu Pro Arg Asn
             100                 105                 110
Lys Ala Gln Val Lys Pro Gly Gln Ala Cys Asp Val Ala Gly Trp Gly
             115                 120                 125
Gln Thr Thr Pro Asp Gly Lys Tyr Ser His Thr Leu Gln Glu Val Lys
130                 135                 140
Leu Thr Val Glu Glu Asp Gln Thr Cys Lys Ser Arg Leu Gly His Tyr
145                 150                 155                 160
Tyr Asp Ser Thr Val Glu Leu Cys Val Gly Asp Pro Glu Ile Gln Lys
                165                 170                 175
Ala Ser Phe Lys Gly Asp Ser Gly Gly Pro Leu Val Cys Asn Lys Val
             180                 185                 190
Ala Gln Gly Ile Val Ser Tyr Gly Gln Arg Asn Gly Lys Pro Pro Arg
             195                 200                 205
Val Cys Thr Lys Val Ser Ser Phe Val Arg Trp Ile Lys Lys Thr Met
             210                 215                 220
Lys Arg His
225

<210> SEQ ID NO 6
<211> LENGTH: 227
<212> TYPE: PRT
<213> ORGANISM: Macaca mulatta

<400> SEQUENCE: 6

Ile Ile Gly Gly His Glu Ala Lys Pro His Ser Arg Pro Tyr Met Ala
 1               5                  10                  15
Tyr Leu Met Ile Trp Asp Gln Met Ser Leu Lys Arg Cys Gly Gly Phe
             20                  25                  30
Leu Ile Arg Glu Asp Phe Val Leu Thr Ala Ala His Cys Trp Gly Ser
         35                  40                  45
Ser Ile Asn Val Thr Leu Gly Ala His Asn Ile Lys Glu Gln Glu Arg
 50                  55                  60
Thr Gln Gln Ile Ile Pro Val Lys Arg Ala Ile Pro His Pro Ala Tyr
 65                  70                  75                  80
Asn Pro Lys Asn Phe Ser Asn Asp Ile Met Leu Leu Gln Leu Glu Arg
                 85                  90                  95
Lys Ala Lys Arg Thr Thr Ala Val Lys Pro Leu Arg Leu Pro Arg Asn
             100                 105                 110
Lys Ala Gln Val Lys Pro Gly Gln Ala Cys Asp Val Ala Gly Trp Gly
             115                 120                 125
Gln Thr Thr Pro Asp Gly Lys Tyr Ser His Thr Leu Gln Glu Val Lys
130                 135                 140
Leu Thr Val Glu Glu Asp Gln Thr Cys Lys Ser Arg Leu Gly Arg Tyr
```

```
                145                 150                 155                 160
Tyr Asp Ser Thr Val Glu Leu Cys Val Gly Asp Pro Glu Ile Gln Lys
                    165                 170                 175
Ala Ser Phe Lys Gly Asp Ser Gly Pro Leu Val Cys Asn Lys Val
                180                 185                 190
Ala Gln Gly Ile Val Ser Tyr Gly Gln Arg Asn Gly Lys Pro Pro Arg
                195                 200                 205
Val Cys Thr Lys Val Ser Ser Phe Val Arg Trp Ile Lys Lys Thr Met
        210                 215                 220
Lys Arg His
225

<210> SEQ ID NO 7
<211> LENGTH: 227
<212> TYPE: PRT
<213> ORGANISM: Macaca fascicularis

<400> SEQUENCE: 7

Ile Ile Gly Gly His Glu Ala Lys Pro His Ser Arg Pro Tyr Met Ala
1               5                   10                  15
Tyr Leu Met Ile Trp Asp Gln Met Ser Leu Lys Arg Cys Gly Gly Phe
                20                  25                  30
Leu Ile Arg Glu Asp Phe Val Leu Thr Ala Ala His Cys Trp Gly Ser
            35                  40                  45
Ser Ile Asn Val Thr Leu Gly Ala His Asn Ile Lys Glu Gln Glu Arg
        50                  55                  60
Thr Gln Gln Ile Ile Pro Val Lys Arg Ala Ile Pro His Pro Ala Tyr
65                  70                  75                  80
Asn Pro Lys Asn Phe Ser Asn Asp Ile Met Leu Leu Gln Leu Glu Arg
                85                  90                  95
Lys Ala Lys Arg Thr Thr Ala Val Lys Pro Leu Arg Leu Pro Arg Asn
                100                 105                 110
Lys Ala Gln Val Lys Pro Gly Gln Ala Cys Asp Val Ala Gly Trp Gly
            115                 120                 125
Gln Thr Thr Pro Asp Gly Lys Tyr Ala His Thr Leu Gln Glu Val Lys
        130                 135                 140
Leu Thr Val Glu Glu Asp Gln Thr Cys Lys Ser Arg Leu Gly Arg Tyr
145                 150                 155                 160
Tyr Asp Ser Thr Val Glu Leu Cys Val Gly Asp Pro Glu Ile Gln Lys
                    165                 170                 175
Ala Ser Phe Lys Gly Asp Ser Gly Pro Leu Val Cys Asn Lys Val
                180                 185                 190
Ala Gln Gly Ile Val Ser Tyr Gly Gln Arg Asn Gly Lys Pro Pro Arg
                195                 200                 205
Val Cys Thr Lys Val Ser Ser Phe Val Arg Trp Ile Lys Lys Thr Met
        210                 215                 220
Lys Arg His
225

<210> SEQ ID NO 8
<211> LENGTH: 226
<212> TYPE: PRT
<213> ORGANISM: Sus scrofa

<400> SEQUENCE: 8

Ile Ile Gly Gly His Glu Ala Lys Pro His Ser Arg Pro Tyr Met Ala
```

```
1               5                   10                  15
Tyr Leu Gln Ile Gln Asp Gln Asp Asn Arg Ser Arg Cys Gly Gly Phe
                20                  25                  30

Leu Ile Arg Glu Asp Phe Val Leu Thr Ala Ala His Cys Trp Gly Ser
                35                  40                  45

Ser Ile Asn Val Thr Leu Gly Ala His Asn Ile Lys Lys Gln Glu Glu
            50                  55                  60

Thr Gln Gln Val Ile Pro Val Arg Lys Ala Ile Arg His Pro Asp Tyr
65                  70                  75                  80

Asn Glu Lys Arg Ile Ser Asn Asp Ile Met Leu Leu Gln Leu Glu Arg
                85                  90                  95

Lys Ala Lys Leu Thr Lys Ala Val Lys Thr Leu Gly Leu Pro Gly Ala
                100                 105                 110

Lys Ala Arg Val Lys Pro Gly Gln Val Cys Ser Val Ala Gly Trp Gly
                115                 120                 125

Gln Val Glu Arg Gly Ile Tyr Thr Asp Thr Leu Gln Glu Val Lys Leu
130                 135                 140

Thr Leu Gln Lys Asp Gln Glu Cys Asp Ser Tyr Leu Pro Asn Tyr Tyr
145                 150                 155                 160

Asn Gly Asn Thr Gln Leu Cys Val Gly Asp Pro Lys Lys Lys Gln Ala
                165                 170                 175

Thr Phe Lys Gly Asp Ser Gly Gly Pro Leu Val Cys Asn Asn Val Ala
                180                 185                 190

Gln Gly Ile Val Ser Tyr Gly Lys Lys Asp Gly Thr Pro Pro Arg Ala
                195                 200                 205

Cys Thr Lys Val Ser Ser Phe Leu Pro Trp Ile Lys Lys Ile Met Lys
210                 215                 220

Ser Leu
225

<210> SEQ ID NO 9
<211> LENGTH: 226
<212> TYPE: PRT
<213> ORGANISM: Bos taurus

<400> SEQUENCE: 9

Ile Ile Gly Gly His Glu Ala Lys Pro His Ser Arg Pro Tyr Met Ala
1               5                   10                  15

Tyr Leu Gln Tyr Trp Asn Gln Asp Val Gln Ser Arg Cys Gly Gly Phe
                20                  25                  30

Leu Val Arg Gln Asp Phe Val Leu Thr Ala Ala His Cys Asn Gly Ser
                35                  40                  45

Ser Ile Lys Val Thr Leu Gly Ala His Asn Ile Lys Gln Gln Glu Arg
            50                  55                  60

Thr Gln Gln Val Ile Arg Val Arg Arg Ala Ile Ser His Pro Asp Tyr
65                  70                  75                  80

Asn Pro Lys Asn Phe Ser Asn Asp Ile Met Leu Leu Lys Leu Glu Arg
                85                  90                  95

Lys Ala Lys Gln Thr Ser Ala Val Lys Pro Leu Ser Leu Pro Arg Ala
                100                 105                 110

Lys Ala Arg Val Lys Pro Gly Gln Thr Cys Ser Val Ala Gly Trp Gly
                115                 120                 125

Arg Asp Ser Thr Asp Thr Tyr Ala Asp Thr Leu Gln Glu Val Lys Leu
130                 135                 140
```

```
Ile Val Gln Glu Asp Gln Lys Cys Glu Ala Tyr Leu Arg Asn Phe Tyr
145                 150                 155                 160

Asn Arg Ala Ile Gln Leu Cys Val Gly Asp Pro Lys Thr Lys Lys Ala
            165                 170                 175

Ser Phe Gln Gly Asp Ser Gly Gly Pro Leu Val Cys Asp Asn Val Ala
        180                 185                 190

Gln Gly Ile Val Ser Tyr Gly Lys Arg Asp Gly Ser Thr Pro Arg Ala
    195                 200                 205

Phe Thr Lys Val Ser Ser Phe Leu Pro Trp Ile Lys Lys Thr Met Lys
    210                 215                 220

Ser Leu
225

<210> SEQ ID NO 10
<211> LENGTH: 228
<212> TYPE: PRT
<213> ORGANISM: Rattus norvegicus

<400> SEQUENCE: 10

Ile Ile Gly Gly His Glu Ala Lys Pro His Ser Arg Pro Tyr Met Ala
1               5                   10                  15

Tyr Leu Gln Ile Met Asp Glu Tyr Ser Gly Ser Lys Lys Cys Gly Gly
            20                  25                  30

Phe Leu Ile Arg Glu Asp Phe Val Leu Thr Ala Ala His Cys Ser Gly
        35                  40                  45

Ser Lys Ile Asn Val Thr Leu Gly Ala His Asn Ile Lys Glu Gln Glu
    50                  55                  60

Lys Met Gln Gln Ile Ile Pro Val Val Lys Ile Ile Pro His Pro Ala
65                  70                  75                  80

Tyr Asn Ser Lys Thr Ile Ser Asn Asp Ile Met Leu Leu Lys Leu Lys
                85                  90                  95

Ser Lys Ala Lys Arg Ser Ser Ala Val Lys Pro Leu Asn Leu Pro Arg
            100                 105                 110

Arg Asn Val Lys Val Lys Pro Gly Asp Val Cys Tyr Val Ala Gly Trp
        115                 120                 125

Gly Lys Leu Gly Pro Met Gly Lys Tyr Ser Asp Thr Leu Gln Glu Val
    130                 135                 140

Glu Leu Thr Val Gln Glu Asp Gln Lys Cys Glu Ser Tyr Leu Lys Asn
145                 150                 155                 160

Tyr Phe Asp Lys Ala Asn Glu Ile Cys Ala Gly Asp Pro Lys Ile Lys
                165                 170                 175

Arg Ala Ser Phe Arg Gly Asp Ser Gly Gly Pro Leu Val Cys Lys Lys
            180                 185                 190

Val Ala Ala Gly Ile Val Ser Tyr Gly Gln Asn Asp Gly Ser Thr Pro
        195                 200                 205

Arg Ala Phe Thr Lys Val Ser Thr Phe Leu Ser Trp Ile Lys Lys Thr
    210                 215                 220

Met Lys Lys Ser
225

<210> SEQ ID NO 11
<211> LENGTH: 227
<212> TYPE: PRT
<213> ORGANISM: Mus musculus

<400> SEQUENCE: 11
```

```
Ile Ile Gly Gly His Glu Val Lys Pro His Ser Arg Pro Tyr Met Ala
1               5                   10                  15

Leu Leu Ser Ile Lys Asp Gln Gln Pro Glu Ala Ile Cys Gly Gly Phe
            20                  25                  30

Leu Ile Arg Glu Asp Phe Val Leu Thr Ala Ala His Cys Glu Gly Ser
        35                  40                  45

Ile Ile Asn Val Thr Leu Gly Ala His Asn Ile Lys Glu Gln Glu Lys
    50                  55                  60

Thr Gln Gln Val Ile Pro Met Val Lys Cys Ile Pro His Pro Asp Tyr
65                  70                  75                  80

Asn Pro Lys Thr Phe Ser Asn Asp Ile Met Leu Leu Lys Leu Lys Ser
                85                  90                  95

Lys Ala Lys Arg Thr Arg Ala Val Arg Pro Leu Asn Leu Pro Arg Arg
            100                 105                 110

Asn Val Asn Val Lys Pro Gly Asp Val Cys Tyr Val Ala Gly Trp Gly
            115                 120                 125

Arg Met Ala Pro Met Gly Lys Tyr Ser Asn Thr Leu Gln Glu Val Glu
130                 135                 140

Leu Thr Val Gln Lys Asp Arg Glu Cys Glu Ser Tyr Phe Lys Asn Arg
145                 150                 155                 160

Tyr Asn Lys Thr Asn Gln Ile Cys Val Gly Asp Pro Lys Thr Lys Arg
                165                 170                 175

Ala Ser Phe Arg Gly Asp Ser Gly Gly Pro Leu Val Cys Lys Lys Val
            180                 185                 190

Ala Ala Gly Ile Val Ser Tyr Gly Tyr Lys Asp Gly Ser Pro Pro Arg
            195                 200                 205

Ala Phe Thr Lys Val Ser Ser Phe Leu Ser Trp Ile Lys Lys Thr Met
    210                 215                 220

Lys Ser Ser
225

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ser Ser Cys Ser Gly Ser Ala
1               5

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Gly Ser Thr Ser Gly Ser Gly Lys Pro Gly Ser Gly Glu Gly Ser Thr
1               5                   10                  15

Lys Gly

<210> SEQ ID NO 14
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 14

Glu Ala Ala Ala Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Gly Gly Gly Gly Ser
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 26
<212> TYPE: PRT
<213> ORGANISM: Artificial Sequence
<220> FEATURE:
<223> OTHER INFORMATION: Synthetic peptide

<400> SEQUENCE: 17

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Gly Arg Lys Lys Arg Arg Gln Arg Arg Arg Pro Pro Gln
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Thr Lys Ile Glu Ser Leu Lys Glu His Gly
1               5                   10

<210> SEQ ID NO 20
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 20

Thr Gln Ile Glu Asn Leu Lys Glu Lys Gly
1               5                   10

<210> SEQ ID NO 21
<211> LENGTH: 25
<212> TYPE: PRT
<213> ORGANISM: Artificial Sequence
<220> FEATURE:
<223> OTHER INFORMATION: Synthetic peptide

<400> SEQUENCE: 21

Gly Leu Phe Glu Ala Ile Glu Gly Phe Ile Glu Asn Gly Trp Glu Gly
1               5                   10                  15

Met Ile Glu Gly Trp Tyr Gly Cys Gly
            20                  25

<210> SEQ ID NO 22
<211> LENGTH: 26
<212> TYPE: PRT
<213> ORGANISM: Artificial Sequence
<220> FEATURE:
<223> OTHER INFORMATION: Synthetic peptide

<400> SEQUENCE: 22

Ala Ala Leu Glu Ala Leu Ala Glu Ala Leu Glu Ala Leu Ala Glu Ala
1               5                   10                  15

Leu Glu Ala Leu Ala Glu Ala Ala Ala Ala
            20                  25

<210> SEQ ID NO 23
<211> LENGTH: 244
<212> TYPE: PRT
<213> ORGANISM: Artificial Sequence
<220> FEATURE:
<223> OTHER INFORMATION: Synthetic polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Gly Gly
            100                 105                 110

Gly Ser Gly Gly Gly Gly Ser Gly Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Thr Tyr Ile His Trp
```

```
              145                 150                 155                 160
Val Arg Gln Ala Pro Gly Lys Gly Leu Glu Trp Val Ala Arg Ile Tyr
                    165                 170                 175
Pro Thr Asn Gly Tyr Thr Arg Tyr Ala Asp Ser Val Lys Gly Arg Phe
                180                     185                 190
Thr Ile Ser Ala Asp Thr Ser Lys Asn Thr Ala Tyr Leu Gln Met Asn
            195                 200                 205
Ser Leu Arg Ala Glu Asp Thr Ala Val Tyr Tyr Cys Ser Arg Trp Gly
        210                 215                 220
Gly Asp Gly Phe Tyr Ala Met Asp Tyr Trp Gly Gln Gly Thr Leu Val
    225                 230                 235                 240
Thr Val Ser Ser

<210> SEQ ID NO 24
<211> LENGTH: 546
<212> TYPE: PRT
<213> ORGANISM: Artificial Sequence
<220> FEATURE:
<223> OTHER INFORMATION: Synthetic polypeptide

<400> SEQUENCE: 24

Ile Ile Gly Gly His Glu Ala Lys Pro His Ser Arg Pro Tyr Met Ala
1               5                   10                  15
Tyr Leu Met Ile Trp Asp Gln Lys Ser Leu Lys Arg Cys Gly Gly Phe
                20                  25                  30
Leu Ile Gln Asp Asp Phe Val Leu Thr Ala Ala His Cys Trp Gly Ser
            35                  40                  45
Ser Ile Asn Val Thr Leu Gly Ala His Asn Ile Lys Glu Gln Glu Pro
    50                  55                  60
Thr Gln Gln Phe Ile Pro Val Lys Arg Pro Ile Pro His Pro Ala Tyr
65                  70                  75                  80
Asn Pro Lys Asn Phe Ser Asn Asp Ile Met Leu Leu Gln Leu Glu Arg
                85                  90                  95
Lys Ala Lys Arg Thr Arg Ala Val Gln Pro Leu Arg Leu Pro Ser Asn
                100                 105                 110
Lys Ala Gln Val Lys Pro Gly Gln Thr Cys Ser Val Ala Gly Trp Gly
            115                 120                 125
Gln Thr Ala Pro Leu Gly Lys His Ser His Thr Leu Gln Glu Val Lys
    130                 135                 140
Met Thr Val Gln Glu Asp Arg Lys Cys Glu Ser Asp Leu Arg His Tyr
145                 150                 155                 160
Tyr Asp Ser Thr Ile Glu Leu Cys Val Gly Asp Pro Glu Ile Lys Lys
                165                 170                 175
Thr Ser Phe Lys Gly Asp Ser Gly Gly Pro Leu Val Cys Asn Lys Val
            180                 185                 190
Ala Gln Gly Ile Val Ser Tyr Gly Arg Asn Asn Gly Met Pro Pro Arg
        195                 200                 205
Ala Cys Thr Lys Val Ser Ser Phe Val His Trp Ile Lys Lys Thr Met
    210                 215                 220
Lys Arg Tyr Ala Ala Ala Gly Gly Gly Ser Gly Ser Thr Ser Gly
225                 230                 235                 240
Ser Gly Lys Pro Gly Ser Gly Glu Gly Ser Thr Lys Gly Gly Ser Gly
                245                 250                 255
Ser Gly Asp Ile Gln Met Thr Gln Ser Pro Ser Ser Leu Ser Ala Ser
            260                 265                 270
```

```
Val Gly Asp Arg Val Thr Ile Thr Cys Arg Ala Ser Gln Asp Val Asn
        275                 280                 285

Thr Ala Val Ala Trp Tyr Gln Gln Lys Pro Gly Lys Ala Pro Lys Leu
    290                 295                 300

Leu Ile Tyr Ser Ala Ser Phe Leu Tyr Ser Gly Val Pro Ser Arg Phe
305                 310                 315                 320

Ser Gly Ser Arg Ser Gly Thr Asp Phe Thr Leu Thr Ile Ser Ser Leu
            325                 330                 335

Gln Pro Glu Asp Phe Ala Thr Tyr Tyr Cys Gln Gln His Tyr Thr Thr
            340                 345                 350

Pro Pro Thr Phe Gly Gln Gly Thr Lys Val Glu Ile Lys Arg Thr Gly
        355                 360                 365

Gly Gly Gly Ser Gly Gly Gly Gly Ser Gly Gly Gly Ser Glu Val
    370                 375                 380

Gln Leu Val Glu Ser Gly Gly Gly Leu Val Gln Pro Gly Gly Ser Leu
385                 390                 395                 400

Arg Leu Ser Cys Ala Ala Ser Gly Phe Asn Ile Lys Asp Thr Tyr Ile
            405                 410                 415

His Trp Val Arg Gln Ala Pro Gly Lys Gly Leu Glu Trp Val Ala Arg
            420                 425                 430

Ile Tyr Pro Thr Asn Gly Tyr Thr Arg Tyr Ala Asp Ser Val Lys Gly
        435                 440                 445

Arg Phe Thr Ile Ser Ala Asp Thr Ser Lys Asn Thr Ala Tyr Leu Gln
    450                 455                 460

Met Asn Ser Leu Arg Ala Glu Asp Thr Ala Val Tyr Tyr Cys Ser Arg
465                 470                 475                 480

Trp Gly Gly Asp Gly Phe Tyr Ala Met Asp Tyr Trp Gly Gln Gly Thr
                485                 490                 495

Leu Val Thr Val Ser Ser Gly Ser Thr Ser Gly Ser Gly Lys Pro Gly
            500                 505                 510

Ser Gly Glu Gly Ser Thr Lys Gly Ala Ala Leu Glu Ala Leu Ala Glu
        515                 520                 525

Ala Leu Glu Ala Leu Ala Glu Ala Leu Glu Ala Leu Ala Glu Ala Ala
    530                 535                 540

Ala Ala
545

<210> SEQ ID NO 25
<211> LENGTH: 6
<212> TYPE: PRT
<213> ORGANISM: Homo sapiens

<400> SEQUENCE: 25

Tyr Val Asp Glu Val Asp
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide

<400> SEQUENCE: 26

Tyr Val Asp Glu Val Asp Ile Ile Gly Gly His Glu Ala Lys
1               5                   10
```

```
<210> SEQ ID NO 27
<211> LENGTH: 8
<212> TYPE: PRT
<213> ORGANISM: Homo sapiens

<400> SEQUENCE: 27

Ile Ile Gly Gly His Glu Ala Lys
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X is I or A
<220> FEATURE:
<221> NAME/KEY: VARIANT
<222> LOCATION: (2)..(2)
<223> OTHER INFORMATION: X is E or D

<400> SEQUENCE: 28

Xaa Xaa Gly Arg
1

<210> SEQ ID NO 29
<211> LENGTH: 12
<212> TYPE: PRT
<213> ORGANISM: Artificial Sequence
<220> FEATURE:
<223> OTHER INFORMATION: Synthetic peptide

<400> SEQUENCE: 29

Arg Val Arg Arg Ile Ile Gly Gly His Glu Ala Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide

<400> SEQUENCE: 30

Arg Val Arg Arg Ile Ile Gly Gly His Glu Ala Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: X is I or A
<220> FEATURE:
<221> NAME/KEY: VARIANT
<222> LOCATION: (2)..(2)
<223> OTHER INFORMATION: X is E or D

<400> SEQUENCE: 31

Xaa Xaa Gly Arg Ile Ile Gly Gly His Glu Ala Lys
1               5                   10
```

```
<210> SEQ ID NO 32
<211> LENGTH: 12
<212> TYPE: PRT
<213> ORGANISM: Artificial Sequence
<220> FEATURE:
<223> OTHER INFORMATION: Synthetic peptide

<400> SEQUENCE: 32

Tyr Glu Val Asp Ile Ile Gly Gly His Glu Ala Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33

Trp Glu His Asp Ile Ile Gly Gly His Glu Ala Lys
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide

<400> SEQUENCE: 34

Asp Val Ala Asp Ile Ile Gly Gly His Glu Ala Lys
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Asp Glu His Asp Ile Ile Gly Gly His Glu Ala Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide

<400> SEQUENCE: 36

Asp Glu Val Asp Ile Ile Gly Gly His Glu Ala Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic peptide

<400> SEQUENCE: 37

Asp Met Gln Asp Ile Ile Gly Gly His Glu Ala Lys
1               5                   10
```

```
<210> SEQ ID NO 38
<211> LENGTH: 12
<212> TYPE: PRT
<213> ORGANISM: Artificial Sequence
<220> FEATURE:
<223> OTHER INFORMATION: Synthetic peptide

<400> SEQUENCE: 38

Leu Glu Val Asp Ile Ile Gly Gly His Glu Ala Lys
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic peptide

<400> SEQUENCE: 39

Leu Glu His Asp Ile Ile Gly Gly His Glu Ala Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic peptide

<400> SEQUENCE: 40

Val Glu Ile Asp Ile Ile Gly Gly His Glu Ala Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic peptide

<400> SEQUENCE: 41

Val Glu His Asp Ile Ile Gly Gly His Glu Ala Lys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide

<400> SEQUENCE: 42

Ile Glu Thr Asp Ile Ile Gly Gly His Glu Ala Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide

<400> SEQUENCE: 43

Leu Glu Thr Asp Ile Ile Gly Gly His Glu Ala Lys
1               5                   10

<210> SEQ ID NO 44
```

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 44

Ile Glu Ala Asp Ile Ile Gly Gly His Glu Ala Lys
1               5                   10

<210> SEQ ID NO 45
<211> LENGTH: 723
<212> TYPE: PRT
<213> ORGANISM: Artificial Sequence
<220> FEATURE:
<223> OTHER INFORMATION: Synthetic polypeptide

<400> SEQUENCE: 45

Ile Ile Gly Gly His Glu Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Gln Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr Ala Ala Ala Gly Gly Gly Ser Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
```

-continued

```
            305                 310                 315                 320
        Arg Val Val Ser Val Leu Thr Val Leu His Gln Asp Trp Leu Asn Gly
                            325                 330                 335
        Lys Glu Tyr Lys Cys Lys Val Ser Asn Lys Ala Leu Pro Ala Pro Ile
                            340                 345                 350
        Glu Lys Thr Ile Ser Lys Ala Lys Gly Gln Pro Arg Glu Pro Gln Val
                            355                 360                 365
        Tyr Thr Leu Pro Pro Ser Arg Asp Glu Leu Thr Lys Asn Gln Val Ser
                    370                 375                 380
        Leu Thr Cys Leu Val Lys Gly Phe Tyr Pro Ser Asp Ile Ala Val Glu
        385                 390                 395                 400
        Trp Glu Ser Asn Gly Gln Pro Glu Asn Asn Tyr Lys Thr Thr Pro Pro
                            405                 410                 415
        Val Leu Asp Ser Asp Gly Ser Phe Phe Leu Tyr Ser Lys Leu Thr Val
                            420                 425                 430
        Asp Lys Ser Arg Trp Gln Gln Gly Asn Val Phe Ser Cys Ser Val Met
                            435                 440                 445
        His Glu Ala Leu His Asn His Tyr Thr Gln Lys Ser Leu Pro Leu Ser
                    450                 455                 460
        Pro Gly Lys Gly Gly Gly Gly Ser Gln Val Gln Leu Val Gln Ser Gly
        465                 470                 475                 480
        Ala Glu Val Lys Lys Pro Gly Ala Ser Val Lys Val Ser Cys Lys Ala
                            485                 490                 495
        Ser Gly Tyr Thr Phe Thr Asp Phe Ile Ile Ala Trp Val Lys Gln Ala
                            500                 505                 510
        Pro Gly Gln Gly Leu Glu Trp Ile Gly Glu Ile Tyr Pro Gly Thr Gly
                    515                 520                 525
        Arg Thr Tyr Tyr Ser Glu Lys Phe Arg Gly Lys Ala Thr Leu Thr Ala
                    530                 535                 540
        Asp Thr Ser Thr Ser Thr Ala Tyr Met Glu Leu Ser Ser Leu Arg Ser
        545                 550                 555                 560
        Glu Asp Thr Ala Val Tyr Phe Cys Ala Arg Arg Thr Ile Tyr Tyr Asp
                            565                 570                 575
        Tyr Asp Gly Asp Tyr Trp Gly Gln Gly Thr Leu Val Thr Val Ser Ser
                    580                 585                 590
        Gly Ser Thr Ser Gly Ser Gly Lys Pro Gly Ser Gly Glu Gly Ser Thr
                    595                 600                 605
        Lys Gly Asp Ile Val Met Thr Gln Ser Pro Leu Ser Leu Pro Val Thr
                    610                 615                 620
        Pro Gly Glu Pro Ala Ser Ile Ser Cys Arg Ser Ser Lys Ser Leu Leu
        625                 630                 635                 640
        His Ser Asn Gly Ile Thr Tyr Leu Tyr Trp Tyr Leu Gln Lys Pro Gly
                            645                 650                 655
        Gln Ser Pro Gln Leu Leu Ile Tyr Gln Met Ser Asn Leu Ala Ser Gly
                            660                 665                 670
        Val Pro Asp Arg Phe Ser Gly Ser Gly Ser Gly Thr Asp Phe Thr Leu
                            675                 680                 685
        Lys Ile Ser Arg Val Glu Ala Glu Asp Val Gly Val Tyr Tyr Cys Ala
                    690                 695                 700
        His Asn Leu Glu Leu Pro Trp Thr Phe Gly Gln Gly Thr Lys Val Glu
        705                 710                 715                 720
        Ile Lys Arg
```

<210> SEQ ID NO 46
<211> LENGTH: 234
<212> TYPE: PRT
<213> ORGANISM: Homo sapiens

<400> SEQUENCE: 46

```
Ile Ile Gly Gly Asn Glu Val Thr Pro His Ser Arg Pro Tyr Met Val
1               5                   10                  15

Leu Leu Ser Leu Asp Arg Lys Thr Ile Cys Ala Gly Ala Leu Ile Ala
            20                  25                  30

Lys Asp Trp Val Leu Thr Ala Ala His Cys Asn Leu Asn Lys Arg Ser
        35                  40                  45

Gln Val Ile Leu Gly Ala His Ser Ile Thr Arg Glu Glu Pro Thr Lys
50                  55                  60

Gln Ile Met Leu Val Lys Lys Glu Phe Pro Tyr Pro Cys Tyr Asp Pro
65                  70                  75                  80

Ala Thr Arg Glu Gly Asp Leu Lys Leu Leu Gln Leu Met Glu Lys Ala
                85                  90                  95

Lys Ile Asn Lys Tyr Val Thr Ile Leu His Leu Pro Lys Lys Gly Asp
            100                 105                 110

Asp Val Lys Pro Gly Thr Met Cys Gln Val Ala Gly Trp Gly Arg Thr
        115                 120                 125

His Asn Ser Ala Ser Trp Ser Asp Thr Leu Arg Glu Val Asn Ile Thr
130                 135                 140

Ile Ile Asp Arg Lys Val Cys Asn Asp Arg Asn His Tyr Asn Phe Asn
145                 150                 155                 160

Pro Val Ile Gly Met Asn Met Val Cys Ala Gly Ser Leu Arg Gly Gly
                165                 170                 175

Arg Asp Ser Cys Asn Gly Asp Ser Gly Ser Pro Leu Leu Cys Glu Gly
            180                 185                 190

Val Phe Arg Gly Val Thr Ser Phe Gly Leu Glu Asn Lys Cys Gly Asp
        195                 200                 205

Pro Arg Gly Pro Gly Val Tyr Ile Leu Leu Ser Lys Lys His Leu Asn
210                 215                 220

Trp Ile Ile Met Thr Ile Lys Gly Ala Val
225                 230
```

<210> SEQ ID NO 47
<211> LENGTH: 226
<212> TYPE: PRT
<213> ORGANISM: Homo sapiens

<400> SEQUENCE: 47

```
Ile Ile Gly Gly His Glu Ala Lys Pro His Ser Arg Pro Tyr Met Ala
1               5                   10                  15

Phe Val Gln Phe Leu Gln Glu Lys Ser Arg Lys Arg Cys Gly Gly Ile
            20                  25                  30

Leu Val Arg Lys Asp Phe Val Leu Thr Ala Ala His Cys Gln Gly Ser
        35                  40                  45

Ser Ile Asn Val Thr Leu Gly Ala His Asn Ile Lys Glu Gln Glu Arg
50                  55                  60

Thr Gln Gln Phe Ile Pro Val Lys Arg Pro Ile Pro His Pro Ala Tyr
65                  70                  75                  80

Asn Pro Lys Asn Phe Ser Asn Asp Ile Met Leu Leu Gln Leu Glu Arg
                85                  90                  95
```

Lys Ala Lys Trp Thr Thr Ala Val Arg Pro Leu Arg Leu Pro Ser Ser
            100                 105                 110

Lys Ala Gln Val Lys Pro Gly Gln Leu Cys Ser Val Ala Gly Trp Gly
            115                 120                 125

Tyr Val Ser Met Ser Thr Leu Ala Thr Thr Leu Gln Glu Val Leu Leu
        130                 135                 140

Thr Val Gln Lys Asp Cys Gln Cys Glu Arg Leu Phe His Gly Asn Tyr
145                 150                 155                 160

Ser Arg Ala Thr Glu Ile Cys Val Gly Asp Pro Lys Lys Thr Gln Thr
                165                 170                 175

Gly Phe Lys Gly Asp Ser Gly Gly Pro Leu Val Cys Lys Asp Val Ala
            180                 185                 190

Gln Gly Ile Leu Ser Tyr Gly Asn Lys Lys Gly Thr Pro Pro Gly Val
        195                 200                 205

Tyr Ile Lys Val Ser His Phe Leu Pro Trp Ile Lys Arg Thr Met Lys
210                 215                 220

Arg Leu
225

<210> SEQ ID NO 48
<211> LENGTH: 238
<212> TYPE: PRT
<213> ORGANISM: Homo sapiens

<400> SEQUENCE: 48

Ile Ile Gly Gly Lys Glu Val Ser Pro His Ser Arg Pro Phe Met Ala
1               5                   10                  15

Ser Ile Gln Tyr Gly Gly His His Val Cys Gly Gly Val Leu Ile Asp
            20                  25                  30

Pro Gln Trp Val Leu Thr Ala Ala His Cys Gln Tyr Arg Phe Thr Lys
        35                  40                  45

Gly Gln Ser Pro Thr Val Val Leu Gly Ala His Ser Leu Ser Lys Asn
    50                  55                  60

Glu Ala Ser Lys Gln Thr Leu Glu Ile Lys Lys Phe Ile Pro Phe Ser
65                  70                  75                  80

Arg Val Thr Ser Asp Pro Gln Ser Asn Asp Ile Met Leu Val Lys Leu
                85                  90                  95

Gln Thr Ala Ala Lys Leu Asn Lys His Val Lys Met Leu His Ile Arg
            100                 105                 110

Ser Lys Thr Ser Leu Arg Ser Gly Thr Lys Cys Lys Val Thr Gly Trp
        115                 120                 125

Gly Ala Thr Asp Pro Asp Ser Leu Arg Pro Ser Asp Thr Leu Arg Glu
    130                 135                 140

Val Thr Val Thr Val Leu Ser Arg Lys Leu Cys Asn Ser Gln Ser Tyr
145                 150                 155                 160

Tyr Asn Gly Asp Pro Phe Ile Thr Lys Asp Met Val Cys Ala Gly Asp
                165                 170                 175

Ala Lys Gly Gln Lys Asp Ser Cys Lys Gly Asp Ser Gly Gly Pro Leu
            180                 185                 190

Ile Cys Lys Gly Val Phe His Ala Ile Val Ser Gly Gly His Glu Cys
        195                 200                 205

Gly Val Ala Thr Lys Pro Gly Ile Tyr Thr Leu Leu Thr Lys Lys Tyr
    210                 215                 220

Gln Thr Trp Ile Lys Ser Asn Leu Val Pro Pro His Thr Asn
225                 230                 235

<210> SEQ ID NO 49
<211> LENGTH: 232
<212> TYPE: PRT
<213> ORGANISM: Homo sapiens

<400> SEQUENCE: 49

```
Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
                20                  25                  30

Pro Lys Trp Val Leu Thr Ala Ala His Cys Leu Ala Gln Arg Met Ala
            35                  40                  45

Gln Leu Arg Leu Val Leu Gly Leu His Thr Leu Asp Ser Pro Gly Leu
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
    115                 120                 125

His Gln Gly Gly Arg Leu Ser Arg Val Leu Arg Glu Leu Asp Leu Gln
130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
            180                 185                 190

Val Leu Ala Arg Val Leu Ser Phe Ser Ser Arg Val Cys Thr Asp Ile
    195                 200                 205

Phe Lys Pro Pro Val Ala Thr Ala Val Ala Pro Tyr Val Ser Trp Ile
    210                 215                 220

Arg Lys Val Thr Gly Arg Ser Ala
225                 230
```

<210> SEQ ID NO 50
<211> LENGTH: 235
<212> TYPE: PRT
<213> ORGANISM: Homo sapiens

<400> SEQUENCE: 50

```
Ile Ile Gly Gly Arg Glu Ser Arg Pro His Ser Arg Pro Tyr Met Ala
1               5                   10                  15

Tyr Leu Gln Ile Gln Ser Pro Ala Gly Gln Ser Arg Cys Gly Gly Phe
                20                  25                  30

Leu Val Arg Glu Asp Phe Val Leu Thr Ala Ala His Cys Trp Gly Ser
            35                  40                  45

Asn Ile Asn Val Thr Leu Gly Ala His Asn Ile Gln Arg Arg Glu Asn
    50                  55                  60

Thr Gln Gln His Ile Thr Ala Arg Arg Ala Ile Arg His Pro Gln Tyr
65                  70                  75                  80

Asn Gln Arg Thr Ile Gln Asn Asp Ile Met Leu Leu Gln Leu Ser Arg
                85                  90                  95
```

```
Arg Val Arg Arg Asn Arg Asn Val Asn Pro Val Ala Leu Pro Arg Ala
            100                 105                 110

Gln Glu Gly Leu Arg Pro Gly Thr Leu Cys Thr Val Ala Gly Trp Gly
            115                 120                 125

Arg Val Ser Met Arg Arg Gly Thr Asp Thr Leu Arg Glu Val Gln Leu
            130                 135                 140

Arg Val Gln Arg Asp Arg Gln Cys Leu Arg Ile Phe Gly Ser Tyr Asp
145                 150                 155                 160

Pro Arg Arg Gln Ile Cys Val Gly Asp Arg Arg Glu Arg Lys Ala Ala
                165                 170                 175

Phe Lys Gly Asp Ser Gly Gly Pro Leu Leu Cys Asn Asn Val Ala His
            180                 185                 190

Gly Ile Val Ser Tyr Gly Lys Ser Ser Gly Val Pro Pro Glu Val Phe
            195                 200                 205

Thr Arg Val Ser Ser Phe Leu Pro Trp Ile Arg Thr Thr Met Arg Ser
            210                 215                 220

Phe Lys Leu Leu Asp Gln Met Glu Thr Pro Leu
225                 230                 235

<210> SEQ ID NO 51
<211> LENGTH: 226
<212> TYPE: PRT
<213> ORGANISM: Homo sapiens

<400> SEQUENCE: 51

Ile Ile Gly Gly Thr Glu Cys Lys Pro His Ser Arg Pro Tyr Met Ala
1               5                   10                  15

Tyr Leu Glu Ile Val Thr Ser Asn Gly Pro Ser Lys Phe Cys Gly Gly
            20                  25                  30

Phe Leu Ile Arg Arg Asn Phe Val Leu Thr Ala Ala His Cys Ala Gly
            35                  40                  45

Arg Ser Ile Thr Val Thr Leu Gly Ala His Asn Ile Thr Glu Glu Glu
        50                  55                  60

Asp Thr Trp Gln Lys Leu Glu Val Ile Lys Gln Phe Arg His Pro Lys
65                  70                  75                  80

Tyr Asn Thr Ser Thr Leu His His Asp Ile Met Leu Leu Lys Leu Lys
                85                  90                  95

Glu Lys Ala Ser Leu Thr Leu Ala Val Gly Thr Leu Pro Phe Pro Ser
            100                 105                 110

Gln Phe Asn Phe Val Pro Pro Gly Arg Met Cys Arg Val Ala Gly Trp
            115                 120                 125

Gly Arg Thr Gly Val Leu Lys Pro Gly Ser Asp Thr Leu Gln Glu Val
        130                 135                 140

Lys Leu Arg Leu Met Asp Pro Gln Ala Cys Ser His Phe Arg Asp Phe
145                 150                 155                 160

Asp His Asn Leu Gln Leu Cys Val Gly Asn Pro Arg Lys Thr Lys Ser
                165                 170                 175

Ala Phe Lys Gly Asp Ser Gly Gly Pro Leu Leu Cys Ala Gly Val Ala
            180                 185                 190

Gln Gly Ile Val Ser Tyr Gly Arg Ser Asp Ala Lys Pro Pro Ala Val
            195                 200                 205

Phe Thr Arg Ile Ser His Tyr Arg Pro Trp Ile Asn Gln Ile Leu Gln
        210                 215                 220

Ala Asn
```

```
<210> SEQ ID NO 52
<211> LENGTH: 229
<212> TYPE: PRT
<213> ORGANISM: Homo sapiens

<400> SEQUENCE: 52

Ile Val Gly Gly His Glu Ala Gln Pro His Ser Arg Pro Tyr Met Ala
1               5                   10                  15

Ser Leu Gln Met Arg Gly Asn Pro Gly Ser His Phe Cys Gly Gly Thr
                20                  25                  30

Leu Ile His Pro Ser Phe Val Leu Thr Ala Ala His Cys Leu Arg Asp
            35                  40                  45

Ile Pro Gln Arg Leu Val Asn Val Val Leu Gly Ala His Asn Val Arg
        50                  55                  60

Thr Gln Glu Pro Thr Gln Gln His Phe Ser Val Ala Gln Val Phe Leu
65                  70                  75                  80

Asn Asn Tyr Asp Ala Glu Asn Lys Leu Asn Asp Val Leu Leu Ile Gln
                85                  90                  95

Leu Ser Ser Pro Ala Asn Leu Ser Ala Ser Val Ala Thr Val Gln Leu
            100                 105                 110

Pro Gln Gln Asp Gln Pro Val Pro His Gly Thr Gln Cys Leu Ala Met
        115                 120                 125

Gly Trp Gly Arg Val Gly Ala His Asp Pro Pro Ala Gln Val Leu Gln
130                 135                 140

Glu Leu Asn Val Thr Val Thr Phe Phe Cys Arg Pro His Asn Ile
145                 150                 155                 160

Cys Thr Phe Val Pro Arg Arg Lys Ala Gly Ile Cys Phe Gly Asp Ser
                165                 170                 175

Gly Gly Pro Leu Ile Cys Asp Gly Ile Ile Gln Gly Ile Asp Ser Phe
            180                 185                 190

Val Ile Trp Gly Cys Ala Thr Arg Leu Phe Pro Asp Phe Phe Thr Arg
        195                 200                 205

Val Ala Leu Tyr Val Asp Trp Ile Arg Ser Thr Leu Arg Arg Val Glu
    210                 215                 220

Ala Lys Gly Arg Pro
225

<210> SEQ ID NO 53
<211> LENGTH: 227
<212> TYPE: PRT
<213> ORGANISM: Homo sapiens

<400> SEQUENCE: 53

Ile Ile Gly Gly His Thr Cys Thr Arg Ser Ser Gln Pro Trp Gln Ala
1               5                   10                  15

Ala Leu Leu Ala Gly Pro Arg Arg Phe Leu Cys Gly Gly Ala Leu
                20                  25                  30

Leu Ser Gly Gln Trp Val Ile Thr Ala Ala His Cys Gly Arg Pro Ile
            35                  40                  45

Leu Gln Val Ala Leu Gly Lys His Asn Leu Arg Arg Trp Glu Ala Thr
        50                  55                  60

Gln Gln Val Leu Arg Val Val Arg Gln Val Thr His Pro Asn Tyr Asn
65                  70                  75                  80

Ser Arg Thr His Asp Asn Asp Leu Met Leu Leu Gln Leu Gln Gln Pro
```

```
                     85                  90                  95
Ala Arg Ile Gly Arg Ala Val Arg Pro Ile Glu Val Thr Gln Ala Cys
                100                 105                 110

Ala Ser Pro Gly Thr Ser Cys Arg Val Ser Gly Trp Gly Thr Ile Ser
            115                 120                 125

Ser Pro Ile Ala Arg Tyr Pro Ala Ser Leu Gln Cys Val Asn Ile Asn
        130                 135                 140

Ile Ser Pro Asp Glu Val Cys Gln Lys Ala Tyr Pro Arg Thr Ile Thr
145                 150                 155                 160

Pro Gly Met Val Cys Ala Gly Val Pro Gln Gly Gly Lys Asp Ser Cys
                165                 170                 175

Gln Gly Asp Ser Gly Gly Pro Leu Val Cys Arg Gly Gln Leu Gln Gly
            180                 185                 190

Leu Val Ser Trp Gly Met Glu Arg Cys Ala Leu Pro Gly Tyr Pro Gly
        195                 200                 205

Val Tyr Thr Asn Leu Cys Lys Tyr Arg Ser Trp Ile Glu Glu Thr Met
210                 215                 220

Arg Asp Lys
225

<210> SEQ ID NO 54
<211> LENGTH: 228
<212> TYPE: PRT
<213> ORGANISM: Homo sapiens

<400> SEQUENCE: 54

Ile Leu Gly Gly Arg Glu Ala Glu Ala His Ala Arg Pro Tyr Met Ala
1               5                   10                  15

Ser Val Gln Leu Asn Gly Ala His Leu Cys Gly Gly Val Leu Val Ala
            20                  25                  30

Glu Gln Trp Val Leu Ser Ala Ala His Cys Leu Glu Asp Ala Ala Asp
        35                  40                  45

Gly Lys Val Gln Val Leu Leu Gly Ala His Ser Leu Ser Gln Pro Glu
    50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Gln Leu Ser
                85                  90                  95

Glu Lys Ala Thr Leu Gly Pro Ala Val Arg Pro Leu Pro Trp Gln Arg
                100                 105                 110

Val Asp Arg Asp Val Ala Pro Gly Thr Leu Cys Asp Val Ala Gly Trp
            115                 120                 125

Gly Ile Val Asn His Ala Gly Arg Arg Pro Asp Ser Leu Gln His Val
        130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
        195                 200                 205

Lys Pro Gly Ile Tyr Thr Arg Val Ala Ser Tyr Ala Ala Trp Ile Asp
    210                 215                 220
```

Ser Val Leu Ala
225

<210> SEQ ID NO 55
<211> LENGTH: 224
<212> TYPE: PRT
<213> ORGANISM: Homo sapiens

<400> SEQUENCE: 55

```
Ile Val Gly Gly Tyr Thr Cys Glu Glu Asn Ser Leu Pro Tyr Gln Val
1               5                   10                  15

Ser Leu Asn Ser Gly Ser His Phe Cys Gly Gly Ser Leu Ile Ser Glu
            20                  25                  30

Gln Trp Val Val Ser Ala Ala His Cys Tyr Lys Thr Arg Ile Gln Val
        35                  40                  45

Arg Leu Gly Glu His Asn Ile Lys Val Leu Glu Gly Asn Glu Gln Phe
    50                  55                  60

Ile Asn Ala Ala Lys Ile Ile Arg His Pro Gln Tyr Asp Arg Lys Thr
65                  70                  75                  80

Leu Asn Asn Asp Ile Met Leu Ile Lys Leu Ser Ser Arg Ala Val Ile
                85                  90                  95

Asn Ala Arg Val Ser Thr Ile Ser Leu Pro Thr Ala Pro Pro Ala Thr
            100                 105                 110

Gly Thr Lys Cys Leu Ile Ser Gly Trp Gly Asn Thr Ala Ser Ser Gly
        115                 120                 125

Ala Asp Tyr Pro Asp Glu Leu Gln Cys Leu Asp Ala Pro Val Leu Ser
    130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Val Val Ser
            180                 185                 190

Trp Gly Asp Gly Cys Ala Gln Lys Asn Lys Pro Gly Val Tyr Thr Lys
        195                 200                 205

Val Tyr Asn Tyr Val Lys Trp Ile Lys Asn Thr Ile Ala Ala Asn Ser
    210                 215                 220
```

<210> SEQ ID NO 56
<211> LENGTH: 224
<212> TYPE: PRT
<213> ORGANISM: Homo sapiens

<400> SEQUENCE: 56

```
Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Gln Tyr Asp Arg Lys Thr
65                  70                  75                  80

Leu Asn Asn Asp Ile Met Leu Ile Lys Leu Ser Ser Arg Ala Val Ile
                85                  90                  95
```

```
Asn Ala Arg Val Ser Thr Ile Ser Leu Pro Thr Ala Pro Ala Thr
                100                 105                 110

Gly Thr Lys Cys Leu Ile Ser Gly Trp Gly Asn Thr Ala Ser Ser Gly
            115                 120                 125

Ala Asp Tyr Pro Asp Glu Leu Gln Cys Leu Asp Ala Pro Val Leu Ser
        130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Val Val Ser
            180                 185                 190

Trp Gly Asp Gly Cys Ala Gln Lys Asn Lys Pro Gly Val Tyr Thr Lys
        195                 200                 205

Val Tyr Asn Tyr Val Lys Trp Ile Lys Asn Thr Ile Ala Ala Asn Ser
210                 215                 220

<210> SEQ ID NO 57
<211> LENGTH: 250
<212> TYPE: PRT
<213> ORGANISM: Homo sapiens

<400> SEQUENCE: 57

Ile Ile Gly Gly His Glu Val Thr Pro His Ser Arg Pro Tyr Met Ala
1               5                   10                  15

Ser Val Arg Phe Gly Gly Gln His His Cys Gly Gly Phe Leu Leu Arg
            20                  25                  30

Ala Arg Trp Val Val Ser Ala Ala His Cys Phe Ser His Arg Asp Leu
        35                  40                  45

Arg Thr Gly Leu Val Val Leu Gly Ala His Val Leu Ser Thr Ala Glu
    50                  55                  60

Pro Thr Gln Gln Val Phe Gly Ile Asp Ala Leu Thr Thr His Pro Asp
65                  70                  75                  80

Tyr His Pro Met Thr His Ala Asn Asp Ile Cys Leu Leu Arg Leu Asn
                85                  90                  95

Gly Ser Ala Val Leu Gly Pro Ala Val Gly Leu Leu Arg Pro Pro Gly
            100                 105                 110

Arg Arg Ala Arg Pro Pro Thr Ala Gly Thr Arg Cys Arg Val Ala Gly
        115                 120                 125

Trp Gly Phe Val Ser Asp Phe Glu Leu Pro Pro Gly Leu Met Glu
        130                 135                 140

Ala Lys Val Arg Val Leu Asp Pro Asp Val Cys Asn Ser Ser Trp Lys
145                 150                 155                 160

Gly His Leu Thr Leu Thr Met Leu Cys Thr Arg Ser Gly Asp Ser His
                165                 170                 175

Arg Arg Gly Phe Cys Ser Ala Asp Ser Gly Gly Pro Leu Val Cys Arg
            180                 185                 190

Asn Arg Ala His Gly Leu Val Ser Phe Ser Gly Leu Trp Cys Gly Asp
        195                 200                 205

Pro Lys Thr Pro Asp Val Tyr Thr Gln Val Ser Ala Phe Val Ala Trp
    210                 215                 220

Ile Trp Asp Val Val Arg Arg Ser Ser Pro Gln Pro Gly Pro Leu Pro
225                 230                 235                 240

Gly Thr Thr Arg Pro Pro Gly Glu Ala Ala
                245                 250
```

```
<210> SEQ ID NO 58
<211> LENGTH: 250
<212> TYPE: PRT
<213> ORGANISM: Homo sapiens

<400> SEQUENCE: 58

Ile Ile Gly Gly His Glu Val Thr Pro His Ser Arg Pro Tyr Met Ala
1               5                   10                  15

Ser Val Arg Phe Gly Gly Gln His His Cys Gly Gly Phe Leu Leu Arg
            20                  25                  30

Ala Arg Trp Val Val Ser Ala Ala His Cys Phe Ser His Arg Asp Leu
        35                  40                  45

Arg Thr Gly Leu Val Val Leu Gly Ala His Val Leu Ser Thr Ala Glu
    50                  55                  60

Pro Thr Gln Gln Val Phe Gly Ile Asp Ala Leu Thr Thr His Pro Asp
65                  70                  75                  80

Tyr His Pro Met Thr His Ala Asn Asp Ile Cys Leu Leu Arg Leu Asn
                85                  90                  95

Gly Ser Ala Val Leu Gly Pro Ala Val Gly Leu Leu Arg Leu Pro Gly
            100                 105                 110

Arg Arg Ala Arg Pro Pro Thr Ala Gly Thr Arg Cys Arg Val Ala Gly
        115                 120                 125

Trp Gly Phe Val Ser Asp Phe Glu Glu Leu Pro Pro Gly Leu Met Glu
    130                 135                 140

Ala Lys Val Arg Val Leu Asp Pro Asp Val Phe Asn Ser Ser Trp Lys
145                 150                 155                 160

Gly His Leu Thr Leu Thr Met Leu Cys Thr Arg Ser Gly Asp Ser His
                165                 170                 175

Arg Arg Gly Phe Cys Ser Ala Asp Ser Gly Gly Pro Leu Val Cys Arg
            180                 185                 190

Asn Arg Ala His Gly Leu Val Ser Phe Ser Gly Leu Trp Cys Gly Asp
        195                 200                 205

Pro Lys Thr Pro Asp Val Tyr Thr Gln Val Ser Ala Phe Val Ala Trp
    210                 215                 220

Ile Trp Asp Val Val Arg Arg Ser Ser Pro Gln Pro Gly Pro Leu Pro
225                 230                 235                 240

Gly Thr Thr Arg Pro Pro Gly Glu Ala Ala
            245                 250
```

SERINE PROTEASE MOLECULES AND THERAPIES

This application is a divisional of U.S. application Ser. No. 14/322,485, filed Jul. 2, 2014, which is a divisional of U.S. application Ser. No. 14/046,211, filed Oct. 4, 2013, now U.S. Pat. No. 9,096,840, which claims the benefit of U.S. Provisional Application Nos. 61/709,763, filed Oct. 4, 2012; 61/762,173, filed Feb. 7, 2013; and 61/762,216, filed Feb. 7, 2013, each of which is incorporated herein by reference in its entirety.

INCORPORATION OF SEQUENCE LISTING

The sequence listing that is contained in the file named "CLFRP0395USD3.txt", which is 68 KB (as measured in Microsoft Windows®) and was created on Mar. 8, 2018, is filed herewith by electronic submission and is incorporated by reference herein.

BACKGROUND OF THE INVENTION

1. Field of the Invention

The present invention relates generally to the field of molecular biology and recombinant protein production. More particularly, it concerns modified serine protease polypeptides, such as granzymes, and cell-targeting constructs comprising such polypeptides.

2. Description of Related Art

The successful development of targeted therapeutics (e.g., for cancer applications) depends on the identification of ligands and antigens specific for target cells, generation of molecules capable of targeting those components specifically and, finally, use of highly toxic molecules for killing of target cells. Immunoconjugates composed of antibodies and small, toxic drugs or radioisotopes have been successfully tested in vitro, in animal models and have demonstrated activity in the clinical setting. In addition to the use of small molecules for the toxin component, a number of highly cytotoxic protein components, such as diphtheria toxin, ricin A-chain, *Pseudomonas* exotoxin, and gelonin (rGel), have been used for targeted therapies. However, problems such as capillary leak syndrome, immunogenicity and inadvertent toxicity (to non-targeted cells) continue to limit implementation of successful therapy, especially for long-term or chronic applications. Thus, there remains a need for highly specific and highly active toxin molecules and cell-targeting constructs comprising such molecules.

SUMMARY OF THE INVENTION

Certain embodiments of the invention concern truncated serine protease polypeptides and fusion proteins comprising such serine proteases. As used herein, a truncated serine protease polypeptide refers to an engineered serine protease that is truncated such that the leader sequence, positioned N-terminally relative to a IIGG, IVGG or ILGG sequence has been removed or replaced with a heterologous sequence. Examples of such truncated serine protease polypeptides are shown in FIG. 1. In some aspects, a truncated serine protease polypeptide is conjugated to, or fused with, a cell targeting moiety to provide a cell-targeted cytotoxic construct. Such constructs can be used, for example, in the treatment of cell proliferative diseases, such as cancer.

Thus, certain embodiments there is provided a recombinant polypeptide comprising a cleavage site that is susceptible to cleavage by a selected protease fused to a truncated serine protease having an IIGG, IVGG or ILGG at its N-terminus, such that, upon cleavage of the polypeptide by the selected protease, the truncated serine protease having an N-terminal isoleucine will be released from the polypeptide. In some aspects, the protease cleavage site is a caspase, furin, granzyme B or factor Xa cleavage sequence. In some aspects, the protease cleavage site is for an intracellular or extracellular protease. For instance, the cleavage site can be a caspase 1-10 cleavage site (e.g., YEVD, WEHD, DVAD, DEHD, DEVD, DMQD, LEVD, LEHD, VEID, VEHD, IETD, LETD or IEAD), a furin cleavage site (RVRR), a granzyme B cleavage site (IEPD) or a factor Xa cleavage site ((I/A)(E/D)GR; SEQ ID NO: 28). Furthermore, in preferred aspects, the recombinant polypeptide further comprises a cell-binding moiety, positioned N-terminally relative to the cleavage site. For example, the cell-binding moiety can be an antibody or a ligand (e.g., VEGF or BLyS), such as a moiety that binds to GP240, 5T4, HER1, HER2, CD-33, CD-38, VEGFR-1, VEGFR-2, CEA, FGFR3, IGFBP2, Fn14 or IGF-1R.

In some specific aspects a truncated serine protease for use according to the embodiments comprises a sequence at least about 80%, 85%, 90%, 91%, 92%, 93%, 94%, 95%, 96%, 97%, 98%, 99% or more identical to granzyme B (SEQ ID NO: 1), granzyme A (SEQ ID NO: 46), granzyme H (SEQ ID NO: 47), granzyme K (SEQ ID NO: 48), granzyme M (SEQ ID NO: 49), Cathepsin G (SEQ ID NO: 50), Chymase (SEQ ID NO: 51), Myeloblastin (SEQ ID NO: 52), Kallikrein-14 (SEQ ID NO: 53), Complement factor D (SEQ ID NO: 54), PRSS3 protein (SEQ ID NO: 55), Trypsin-1 (SEQ ID NO: 56), Serine protease 57 (SEQ ID NO: 57) or PRSSL1 protein (SEQ ID NO: 58). In certain aspects, the truncated serine protease is at least about 80%, 85%, 90%, 91%, 92%, 93%, 94%, 95%, 96%, 97%, 98%, 99% or more identical to a human granzyme, such as granzyme B (GrB).

In yet further aspects of the embodiments a serine protease (e.g., GrB polypeptide) or targeting agent of the embodiments further comprises an amino acid sequence comprising a Cys, wherein the amino acid sequence is positioned C-terminally relative to the serine protease coding sequence. For example, the polypeptide can comprise the sequence SSCSGSA (SEQ ID NO: 12) positioned C-terminally relative to the serine protease coding sequence. In some aspects, the Cys (positioned C-terminally to serine protease) can be used to conjugate the protease to a further moiety (e.g., a cell-targeting moiety), such as by forming a disulfide bridge.

In further embodiments the invention provides a recombinant Granzyme B (GrB) polypeptide having enhanced stability and/or activity. In some aspects, such GrB polypeptides can be conjugated or fused to a cell-targeting moiety thereby providing a highly specific targeted cytotoxic construct. For example, the cell-targeting moiety can be a cancer-cell targeting polypeptide (e.g., an antibody that binds to a cancer cell-specific antigen). In such aspects, a method of targeted cancer therapy is provided that allows for specific killing of cancer cells that express a given antigen while other cells are left intact. In preferred aspects, the GrB polypeptide and/or the targeting moiety are comprised of a substantially human amino acid sequence. Thus, in some aspects, a polypeptide of the embodiments does not elicit a robust immune response when administered to a human subject.

In certain specific aspects, a granzyme for use according to the embodiments is a GrB coding sequence comprising one or more amino acid deletions and/or substitutions relative to a human GrB sequence such as SEQ ID NO: 1 (see also NCBI accession numbers nos. AAA75490.1 and EAW66003.1, incorporated herein by reference). For example, the recombinant GrB can be at least 80% identical to SEQ ID NO: 1 (e.g., at least about or about 85%, 90%, 91%, 92%, 93%, 94%, 95%, 96%, 97%, 98% or 99% identical to SEQ ID NO: 1). In certain aspects, a GrB polypeptide comprises one or more amino acid substitution to a corresponding amino acid from a GrB of a different species. For instance, a substantially human GrB polypeptide can comprise 1, 2, 3, 4, 5, or more substitutions at amino acid positions for a corresponding amino acid from one of the GrB polypeptides provided in FIG. 1 (e.g., a primate, porcine, bovine or murine GrB). In some aspects, the recombinant GrB comprises one or more of the following features: (a) an amino acid substitution or deletion at the position corresponding to Asp 37; (b) an amino acid substitution or deletion at the position corresponding to Asp 150; (c) an amino acid substitution or deletion at the position corresponding to Asn 51; (d) an amino acid substitution or deletion at the position corresponding to Asn 84; and/or (e) an amino acid substitution or deletion at the position corresponding to Cys 210. In further aspects, a GrB polypeptide comprises two, three, four or five of the features (a)-(e). In certain aspects, a recombinant GrB is defined as a substantially un-glycosylated GrB polypeptide.

In a further embodiment a recombinant GrB polypeptide of the embodiments comprises one or more of the following features: (a) an amino acid substitution or deletion at the position corresponding to Asp 37; (b) an amino acid substitution or deletion at the position corresponding to Asn 51; (c) an amino acid substitution or deletion at the position corresponding to Asn 84; (d) an amino acid substitution or deletion at the position corresponding to Arg 96; (e) an amino acid substitution or deletion at the position corresponding to Arg 100; (f) an amino acid substitution or deletion at the position corresponding to Arg 102; (g) an amino acid substitution or deletion at the position corresponding to Asp 150; (h) an amino acid substitution or deletion at the position corresponding to Arg 201; (i) an amino acid substitution or deletion at the position corresponding to Cys 210; (j) an amino acid substitution or deletion at the position corresponding to Lys 221; (k) an amino acid substitution or deletion at the position corresponding to Lys 222; (l) an amino acid substitution or deletion at the position corresponding to Lys 225; and/or (m) an amino acid substitution or deletion at the position corresponding to Arg 226. Thus, in some aspects, a recombinant polypeptide of the embodiments comprises 1, 2, 3, 4, 5, 6, 7, 8, 9, 10, 11, 12, or all 13 of the features (a)-(m).

In certain aspects, a recombinant GrB polypeptide lacks glycosylation at an amino acid position corresponding to human amino acid position Asn 51 and/or Asn 84. In some aspects, a GrB polypeptide of the embodiments comprises an amino acid substitution or deletion at a position corresponding to human amino acid position Asn 51 and/or Asn 84. In further aspects, a GrB polypeptide comprises a Arg, His, Lys, Asp, Glu, Ser, Thr, Gln, Cys, Gly, Pro, Ala, Val, Ile, Leu, Met, Phe, Tyr or Trp substitution at human amino acid position Asn 51 and/or Asn 84. For example, in one aspect, a recombinant GrB comprises an Ala, Ser, Thr, Lys or Gln substitution at a position corresponding to human amino acid position Asn 51. Alternatively or additionally, a recombinant GrB comprises an Ala, Ser, Thr, Arg or Gln substitution at a position corresponding to human amino acid position Asn 84.

In some aspects, a recombinant GrB polypeptide comprises an amino acid substitution or deletion at the positions corresponding to Lys 27 and/or Arg 28. For example, a recombinant GrB may comprise a substitution at both the positions corresponding to Lys 27 and Arg 28. In some cases, the substitution is selected from K27E or K27L and R28A. In still further aspects, a recombinant GrB coding sequence one, two or three amino acid substitutions or deletions at the positions corresponding to $^{82}$PKN$^{84}$. For example, in some specific aspects, a GrB coding sequence comprises the sequence PVPN substituted at the positions corresponding to $^{82}$PKN$^{84}$.

In further aspects, a recombinant GrB polypeptide of the embodiments comprises an amino acid deletion or substitution (e.g., a substitution of an amino acid having a polar side chain) at an amino acid position corresponding to human amino acid position Asp 37 and/or Asp 150. Thus, in some aspects a recombinant GrB polypeptide comprises a Arg, His, Lys, Glu, Ser, Thr, Asn, Gln, Cys, Gly, Pro, Ala, Val, Ile, Leu, Met, Phe, Tyr or Trp substitution at to human amino acid position Asp 37 and/or Asp 150. For example, a recombinant GrB can comprise a Ser, Thr, Gln, Glu or Asn substitution at a position corresponding to human amino acid position Asp 37. Alternatively or additionally, a recombinant GrB comprises a Ser, Thr, Gln, Glu or Asn substitution at a position corresponding to human amino acid position Asp 150.

In some aspects, a recombinant GrB polypeptide of the embodiments comprises an amino acid substitution or deletion at a position corresponding to human amino acid position Arg 96, Arg 100, Arg 102, Arg 201, and/or Arg 226. In further aspects, a GrB polypeptide comprises a Asn, His, Lys, Asp, Glu, Ser, Thr, Gln, Cys, Gly, Pro, Ala, Val, Ile, Leu, Met, Phe, Tyr or Trp substitution at human amino acid position Arg 96, Arg 100, Arg 102, Arg 201, and/or Arg 226. In certain aspects, a recombinant GrB comprises a substitution at a position corresponding to Arg 96, Arg 100, Arg 102, Arg 201, and/or Arg 226 for an amino acid residue having a polar or positively charged side chain. For example, a recombinant GrB can comprise an Ala, Asn, Ser, Thr, Lys, His or Gln substitution at a position corresponding to human amino acid position Arg 96, Arg 100, Arg 102, Arg 201, and/or Arg 226. In still further aspects, a recombinant polypeptide comprises a deletion or substitution at 2, 3, 4 or 5 of said Arg positions.

In certain aspects, a recombinant GrB polypeptide of the embodiments comprises an amino acid substitution or deletion at a position corresponding to human amino acid position Lys 221, Lys 222 and/or Lys 225. In further aspects, a GrB polypeptide comprises a Asn, His, Arg, Asp, Glu, Ser, Thr, Gln, Cys, Gly, Pro, Ala, Val, Ile, Leu, Met, Phe, Tyr or Trp substitution at human amino acid position Lys 221, Lys 222 and/or Lys 225. In certain aspects, a recombinant GrB comprises a substitution at a position corresponding to Lys 221, Lys 222 and/or Lys 225 for an amino acid residue having a polar or positively charged side chain. For example, a recombinant GrB can comprise an Ala, Asn, Ser, Thr, Arg, His or Gln substitution at a position corresponding to human amino acid position Lys 221, Lys 222 and/or Lys 225. In still further aspects, a recombinant polypeptide comprises a deletion or substitution at 2 or 3 of said Lys positions.

In still further aspects, a recombinant GrB polypeptide of the embodiments comprises an amino acid deletion or substitution at the position corresponding to Cys 210. In some aspects, recombinant GrB comprises a Arg, His, Lys, Asp, Glu, Ser, Thr, Asn, Gln, Gly, Pro, Ala, Val, Ile, Leu, Met, Phe, Tyr or Trp amino acid substitution at the position corresponding to Cys 210. For example, the recombinant GrB polypeptide can comprise an Ala, Val, Ile, Leu, Met, Ser, Thr, Asn, Phe, Tyr or Gln substitution at the position corresponding to Cys 210.

In yet further embodiments there is provided a composition comprising a plurality of recombinant GrB polypeptides (or fusion proteins or conjugates thereof) wherein at least about 90%, 95%, 98%, 99% or 99.5% of the GrB polypeptides have active enzymatic activity. In yet a further embodiment there is provided a composition comprising a plurality of recombinant GrB polypeptides (or fusion proteins or conjugates thereof) wherein at least about 90%, 95%, 98%, 99% or 99.5% of the GrB polypeptides comprise an intact GrB coding sequence (i.e., a GrB polypeptide sequence that has not been proteolytically cleaved). In still yet a further embodiment there is provided a plurality of recombinant GrB polypeptides (or fusion proteins or conjugates thereof) wherein at least about 90%, 95%, 98%, 99% or 99.5% of the GrB polypeptides are present as monomers (i.e., a single GrB polypeptide per molecule) in the composition. For example, any of the foregoing compositions can be defined a pharmaceutical composition, such as an aqueous solution comprising the recombinant GrB polypeptides. In some aspects, a composition of the embodiments comprises a plurality of recombinant GrB polypeptides wherein at least about 90%, 95%, 98%, 99% or 99.5% of the polypeptides have (1) active enzymatic activity; (2) comprise an intact GrB amino acid sequence; and/or (3) are present in the composition as a monomer relative to the GrB polypeptide.

In still a further embodiment there is provided a targeting agent comprising (a) a truncated serine protease of the embodiments; (b) a targeting polypeptide; and (c) a cell penetrating peptide (CPP). In certain aspects, the targeting polypeptide is a cancer cell-targeting polypeptide, such as a polypeptide that binds to Her2/neu. For example the targeting peptide can comprise the scFv 4D5 sequence (SEQ ID NO: 23). A CPP for use in a targeting agent of the embodiments may be any of the CPP sequences detailed herein. In a preferred aspect, the CPP is the "26" CPP, having the sequence of SEQ ID NO: 22. Thus, in some specific aspects, a targeting agent comprises from N-terminus to C-terminus (a) a truncated serine protease coding sequence (e.g., a granzyme); (i) a first linker peptide; (b) a targeting polypeptide; (ii) a second linker peptide; and (c) a cell penetrating peptide (CPP) (e.g., having the sequence of SEQ ID NO: 22). A variety of linker peptides may be used in accordance with the embodiments, for example, the first and/or second linker peptide can comprise the sequence of SEQ ID NO: 13. In still more specific aspects, a targeting agent comprises from N-terminus to C-terminus (a) a recombinant GrB coding sequence (e.g., a wild type mammalian GrB coding sequence or a modified coding sequence of the embodiments) (i) a first linker peptide; (b) a targeting polypeptide; (ii) a second linker peptide; and (c) a cell penetrating peptide (CPP), having the sequence of SEQ ID NO: 22. Accordingly, in some aspects, a targeting agent comprises a polypeptide sequence at least about 90%, 91%, 92%, 93%, 94%, 95%, 96%, 97%, 98% or 99% identical to SEQ ID NO: 24 (e.g., a targeting agent comprising the sequence of SEQ ID NO: 24).

In yet a further embodiment there is provided a method of treating a lapatinib or trastuzumab-resistant cancer (e.g., a breast cancer) in a subject comprising (a) identifying a subject having a lapatinib or trastuzumab-resistant cancer; and (b) administering a Her2/neu-targeted therapeutic to the subject, wherein the Her2/neu-targeted therapeutic is linked to a truncated serine protease of the embodiments (e.g., a GrB polypeptide). For example, in some aspects, the subject has been, or is currently being treated with lapatinib or trastuzumab. In some preferred aspects, the Her2/neu-targeted therapeutic comprises a CPP sequence, such as the one of the targeting agents described supra. Thus, in some aspects, a composition is provided for use in treating a subject having a lapatinib or trastuzumab-resistant cancer, the composition comprising of a Her2/neu-targeted therapeutic comprising a truncated serine protease of the embodiments.

In still a further embodiment a recombinant polypeptide is provided comprising, from N-terminus to C-terminus, (a) a peptide comprising a protease cleavage site; and (b) a truncated serine protease (e.g., a recombinant GrB polypeptide). In some aspects, a protease cleavage site is positioned such that, upon cleavage by the protease, a serine protease is produced having an isoleucine residue at its amino terminus (e.g., IIGG, IVGG or ILGG). Thus, in the case of GrB, upon protease cleavage free GrB is released having an amino terminal sequence of IIGGHEAK; SEQ ID NO: 27. In certain aspects, the protease cleavage site is a site cleaved by a mammalian intracellular protease (e.g., a protease that cleaves at the C-terminus of its recognition sequence). Examples of protease cleavage sites for use according to the embodiments include, without limitation, a caspase 1-10 cleavage site (e.g., YEVD, WEHD, DVAD, DEHD, DEVD, DMQD, LEVD, LEHD, VEID, VEHD, IETD, LETD or IEAD), a furin cleavage site (RVRR), a granzyme B cleavage site (IEPD) or a factor Xa cleavage site ((I/A)(E/D)GR; SEQ ID NO: 28). In certain specific aspects, a caspase-3 cleavage site is used and a recombinant polypeptide of the embodiments comprises the caspase-3 cleavage sequence of SEQ ID NO: 25. In still further aspects, a recombinant polypeptide of the embodiments is a GrB polypeptide and comprises the sequence YVDEVDIIGGHEAK (SEQ ID NO: 26); RVRRIIGGHEAK (SEQ ID NO: 29); RVRRIIG-GHEAK (SEQ ID NO: 30); (I/A)(E/D)GRIIGGHEAK (SEQ ID NO: 31); YEVDIIGGHEAK (SEQ ID NO: 32); WEHDIIGGHEAK (SEQ ID NO: 33); DVADIIGGHEAK (SEQ ID NO: 34); DEHDIIGGHEAK (SEQ ID NO: 35); DEVDIIGGHEAK (SEQ ID NO: 36); DMQDIIGGHEAK (SEQ ID NO: 37); LEVDIIGGHEAK (SEQ ID NO: 38); LEHDIIGGHEAK (SEQ ID NO: 39); VEIDIIGGHEAK (SEQ ID NO: 40); VEHDIIGGHEAK (SEQ ID NO: 41); IETDIIGGHEAK (SEQ ID NO: 42); LETDIIGGHEAK (SEQ ID NO: 43) or IEADIIGGHEAK (SEQ ID NO: 44). As detailed supra, in some aspects, a recombinant polypeptide may further comprise a cell penetrating peptide (CPP) and/or a cell-binding moiety, such as a cell binding moiety positioned N-terminally relative to the protease cleavage sequence. In certain preferred aspects, the cell binding moiety is an antibody or an antigen-binding antibody fragment. Polynucleotide molecules encoding recombinant polypeptides of the embodiments are likewise provided.

In a specific embodiment there is provided a cell-targeting construct comprising (a) a cell-binding moiety (e.g., an antibody or antigen-binding domain thereof); (b) a cleavage site that is susceptible to cleavage by a selected protease; and (c) a GrB coding sequence (such as one of the recombinant polypeptides provided herein) having an IIGG at its N-terminus, such that, upon cleavage of the polypeptide by the selected protease, the GrB having an N-terminal isoleucine will be released from the cell-targeting construct. As demonstrated herein such cell-targeting construct are surprisingly stable even upon extended exposure to serum and thereby provide ideal therapeutic agents. Accordingly, in some aspects, a method of providing a serum-stable cell-targeting construct is provided comprising obtaining a cell-targeting construct comprising a GrB coding sequence positioned C-terminal relative to a heterologous protease cleavage site (e.g., a cleavage site recognized by an intracellular protease).

In yet a further embodiment there is a provided a polynucleotide molecule comprising a sequence that encodes a serine protease polypeptide or constructs of the embodiments. In some aspects, the polynucleotide molecule is comprised in an expression cassette operably linked to expression control sequences (e.g., a promoter, enhancer, intron, polyadenylation signal sequence or transcription terminator sequence). In still further aspects, the polynucleotide molecule encodes a serine protease fusion protein such as cell-targeting construct of the embodiments.

In still a further embodiment a host cell is provided comprising an expressible polynucleotide sequence encoding a truncated serine protease (or a cell-targeting construct) of the embodiments. In some aspects, the host cell further comprises a truncated serine protease polypeptide of the embodiments. For example, a host cell of the embodiments can be a mammalian cell (e.g., a cultured human cell), a yeast cell, a bacterial cell, a ciliate cell or an insect cell. Thus, in a further embodiment there is provided a method of manufacturing a polypeptide comprising: (a) expressing a polynucleotide molecule encoding a truncated serine protease of the embodiments in a cell under conditions to produce the encoded polypeptide; and (b) purifying the polypeptide from the cell.

In a further embodiment there is provided a truncated serine protease polypeptide of the embodiments, wherein the serine protease is conjugated to or fused with a cell-targeting moiety. For example, the serine protease polypeptide can be conjugated to a cell-targeting moiety by a thioester linkage (e.g., using a Cys residue comprised in the serine protease polypeptide or positioned C-terminally relative to the serine protease coding sequence). In some aspects, the cell-binding moiety is fused to a serine protease polypeptide to form a fusion protein. In this aspect, a skilled artisan will recognize that the cell-targeting moiety should be positioned C-terminally relative to the truncated serine protease coding sequence, thereby maintaining protease enzymatic activity. For example, in certain aspects, a cell-targeting moiety can bind to a protein, carbohydrate or lipid expressed on a cell (e.g., specifically or preferentially expressed on a cancer cell). Examples of cell-targeting moieties are further detailed and exemplified below and include, without limitation, moieties that bind to GP240, 5T4, HER1, HER2, CD-33, CD-38, VEGFR-1, VEGFR-2, CEA, FGFR3, IGFBP2, IGF-1R, BAFF-R, TACI, APRIL, Fn14 or HER3.

In yet further aspects, a truncated serine protease or a cell-targeting construct is further conjugated to an imaging agent. For example, the imaging agent can be a radionuclide, a Mill contrast agent or an ultrasound contrast agent. Thus, in some aspects, a method is provided for imaging target cells in a subject comprising administering a cell-targeting construct conjugated to an imaging agent to the subject and imaging the target cells in the subject.

It will be understood that in certain cases, a fusion protein may comprise additional amino acids positioned between the truncated serine protease and the cell targeting polypeptide. In general these sequences are interchangeably termed "linker sequences" or "linker regions." One of skill in the art will recognize that linker regions may be one or more amino acids in length and often comprise one or more glycine residue(s) which confer flexibility to the linker. In some specific examples, linkers for use in the current embodiments include, without limitation, the 218 (GSTSGSGK-PGSGEGSTKG; SEQ ID NO: 13), the HL (EAAAK; SEQ ID NO: 14) SSG and the $G_4S$ (GGGGS; SEQ ID NO: 15) linkers. Such linker sequences can be repeated 1, 2, 3, 4, 5, 6, or more times or combined with one or more different linkers to form an array of linker sequences. For instance, in some applications, a linker region may comprise a protease cleavage site, such as the cleavage site recognized by an endogenous intracellular protease. In this case when the cell targeting construct is internalized into a target cell proteolytic cleavage can separate the serine protease from a cell targeting moiety and/or other polypeptide domains. As such, cell targeting constructs according to this embodiment may have the advantage of enhanced intracellular activity of the targeted serine protease since potential interference from the cell targeting polypeptide will be reduced.

Cell targeting constructs according to the embodiments may comprise additional amino acids attached to the serine protease, the cell targeting moiety, or both. For example, additional amino acids may be included to aid production or purification of a cell targeting construct. Some specific examples of amino acid sequences that may be attached to cell targeting moiety include, but are not limited to, purification tags (e.g., a T7, MBP. GST, HA, or polyHis tag), proteolytic cleavage sites, such as a thrombin or furin cleavage site, intracellular localization signals or secretion signals. Accordingly, in certain aspects, a cell-targeting construct of the embodiments comprises a protease cleavage site (e.g., a furin cleavage site) positioned between a serine protease, such as GrB, and the cell-targeting moiety.

In still further aspects, a cell-targeting construct of the embodiments further comprises a cell-penetrating peptide (CPP). As used herein the terms CPP and membrane translocation peptide (MTP) as used interchangeably to refer to peptide sequences that enhance the ability of a protein to be internalized by a cell. Examples for CPPs for use according to the embodiments include, without limitation, peptide segments derived from HIV Tat, herpes virus VP22, the *Drosophila* Antennapedia homeobox gene product, protegrin I, as well as the T1 (SEQ ID NO: 19), T2 (SEQ ID NO: 20), INF7 (SEQ ID NO: 21) and 26 (SEQ ID NO: 22) peptides exemplified herein. In certain aspects, a cell-targeting construct of the embodiments comprises CPP positioned between the serine protease and the cell-targeting moiety or positioned C-terminally relative to the cell-targeting moiety. In certain aspects a CPP is separated from a serine protease and/or a cell-targeting moiety by a linker sequence.

A cell targeting construct (e.g., comprising a cell-targeting moiety and a serine protease) according to the embodiments will desirably have two properties; (1) binding affinity for a specific population of cells and (2) the ability to be internalized into cells. It is envisioned, however, that even cell targeting constructs that are poorly internalized may be used in methods according to the embodiments. Methods well known to those in the art may be used to determine whether a particular cell targeting construct is internalized by target cells, for example by immunohistochemical staining or immunoblot of intracellular extracts. It is also envisioned that, in certain cases, cell targeting moieties that cannot, by themselves, be internalized, may be internalized in the context of the cell targeting constructs according to the embodiments. Cell targeting moieties for use in the embodiments include but are not limited to antibodies, growth factors, hormones, peptides, aptamers, avimers (see for example U.S. Patent Publns. 20060234299 and 20060223114, incorporated herein by reference) and cytokines. As discussed above, cell targeting moieties may be conjugated to a serine protease via a covalent or non-covalent linkage, and in certain cases the targeting construct may be a fusion protein.

In certain preferred aspects, cell targeting moieties for use in the embodiments are antibodies or fragments thereof. In general the term antibody includes, but is not limited to, polyclonal antibodies, monoclonal antibodies, single chain antibodies, humanized antibodies, a deimmunized antibodies, minibodies, dibodies, tribodies as well as antibody fragments, such as Fab', Fab, F(ab')$_2$, single domain antibody, Fv, or single chain Fv (scFv) antibody single domain antibodies, and antibody mimetics, such as anticalins, and any mixture thereof. In some cases the cell targeting moiety is a single chain antibody (scFv). In a related aspect, the cell targeting domain may be an avimer polypeptide. Therefore, in certain cases, the cell targeting constructs of the embodiments are fusion proteins comprising a GrB polypeptide and a scFv or an avimer. For example, in some very specific aspects, the GrB polypeptide is conjugated or fused to a 15A8, scFvMEL, ZME-018, scFv23, cetuximab or trastuzumab antibody. Likewise, a GrB polypeptide may be fused or conjugated to and anti-CD-33 or anti-CD-38 antibody.

Thus, in some embodiments, the invention provides a cell targeting moiety comprising a human antibody heavy chain and light chain, wherein the antibody light chain, heavy chain or both comprise a truncated serine protease of the embodiments positioned C-terminally relative to the antibody light chain and/or heavy chain. For example, the antibody can be a human IgG, such as an IgG1.

In still a further embodiment there is provided a cell-targeting construct comprising (a) a cell-targeting scFv antibody domain; (b) an antibody heavy chain constant (Fc) domain; and (c) a truncated serine protease of the embodiments. For example, the cell-targeting construct can comprise, from N- to C-terminus, (c) a truncated serine protease; (b) a Fc domain; and (a) a scFv domain. Alternatively, the cell-targeting construct can comprise, from N- to C-terminus, (a) a scFv domain; (b) a Fc domain; (d) a peptide comprising a protease cleavage site (e.g., cleavable by an intracellular protease) and (c) a truncated serine protease of the embodiments. In some aspects, the cell-targeting construct can comprise additional elements, such a linkers or CPPs, fused the N-terminus, c-terminus or between any of the elements (a), (b) and/or (c). In certain specific aspects, the scFv of the cell-targeting construct binds to Fn14 and the serine protease is GrB, such as a cell-targeting construct comprising the sequence of SEQ ID NO: 45 (or sequence at least about 85%, 90% or 95% identical to SEQ ID NO: 45).

In further aspects, a cell targeting moiety of the embodiments can be a growth factor. For example, transforming growth factor, epidermal growth factor, insulin-like growth factor, fibroblast growth factor, B lymphocyte stimulator (BLyS), heregulin, platelet-derived growth factor, vascular endothelial growth factor (VEGF), or hypoxia inducible factor may be used as a cell targeting moiety according to the embodiments. These growth factors enable the targeting of constructs to cells that express the cognate growth factor receptors. For example, VEGF can be used to target cells that express VEGFR-2 and/or VEGFR-1. In still further aspects, the cell targeting moiety may be a polypeptide BLyS (see U.S. Patent Publn. 20060171919, incorporated herein by reference).

In yet further aspects, a cell targeting moiety may be a hormone. Some examples of hormones for use in the embodiments include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin or angiotensinogen. As discussed above targeting constructs that comprise a hormone can be used in methods of targeting cell populations that comprise extracellular receptors for the indicated hormone.

In yet still further aspects of the embodiments, cell targeting moieties may be cytokines. For example, IL1, IL2, IL3, IL4, IL5, IL6, IL7, IL8, IL9, IL10, IL11, IL12, IL13, IL14, IL15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-γ, IFN-α, IFN-β, LT-β, CD40 ligand, Fas ligand, CD27 ligand, CD30 ligand, 4-1BBL, TGF-β, IL 1α, IL-1β, IL-1RA, MIF, TNF-like weak inducer of apoptosis (TWEAK) and IGIF may all be used as targeting moieties according to the embodiments.

From the foregoing description it will be clear to one of skill in the art that cell targeting constructs according to the embodiments may target particular populations of cells depending on the cell targeting moiety that is employed. For instance, the cell targeting moiety may be an infected cell targeting moiety. In this case, the cell targeting moiety may bind to a cellular protein that is primarily expressed on the surface of cells that are infected by a pathogen, such as bacteria, a protozoan or a virus. In certain other aspects, the cell targeting moiety may bind to a factor encoded by the pathogen, such as a bacterial, protozoal or viral protein. In this aspect, it is envisioned that cell targeting constructs may be indirectly targeted to cells by binding to a pathogen before or as it enters a target cell. Thus, the transit of a pathogen into a cell may, in some instances, mediate internalization of the targeting construct. In additional aspects, cell targeting moieties may bind to polypeptides encoded by the pathogen that are expressed on the surface of infected cells. For example, in the case of a cell infected with human immunodeficiency virus (HIV), a cell targeting moiety may bind to, for example, gp120. It is envisioned that any of the foregoing methods may be used to limit the spread of infection. For example, delivery of a serine protease (e.g., GrB) to the infected cell may induce apoptosis or sensitize a cell to undergo apoptosis.

In some aspects of the embodiments a cell-targeting moiety can be defined as an immune cell targeting moiety. In this case, the cell targeting moiety may bind to and/or be internalized by a cell surface molecule that is expressed on a specific populations of immune cells. Thus, targeting a serine protease to certain types of immune cells may be used, for example, to treat autoimmune diseases or lymphomas.

In still further aspects of the embodiments a cell targeting moiety can be a cancer cell targeting moiety. It is well known that certain types of cancer cells aberrantly express surface molecules that are unique as compared to surrounding tissue. Thus, cell targeting moieties that bind to these surface molecules enable the targeted delivery of serine proteases specifically to the cancers cells. For example, a cell-targeting moiety may bind to and be internalized by a lung, breast, brain, prostate, spleen, pancreatic, cervical, ovarian, head and neck, esophageal, liver, skin, kidney, leukemia, bone, testicular, colon or bladder cancer cell. Thus, the effectiveness of a cancer cell-targeted serine protease may, in some cases, be contingent upon the expression or expression level of a particular cancer marker on the cancer cell. In certain aspects, there is provided a method for treating a cancer patient with targeted serine protease comprising identifying whether (or to what extent) cancer cells of the patient expresses a particular cell surface marker and administering a targeted serine protease therapy (optionally, in conjunction with a further anticancer therapy) to a patient identified to have a cancer expressing the particular cell surface marker. In further aspects, the dose of a targeted serine protease therapy can be adjusted depending on the expression level of a cell surface marker on the cancer cells.

Accordingly, in certain embodiments, there is provided a method for treating a cell proliferative disease comprising administering a cell-targeting construct according to the embodiments. As used herein the phrase "cell proliferative condition" includes but is not limited to autoimmune diseases, cancers and precancerous conditions. For example, methods of the embodiments may be used for the treatment of cancers such as lung, breast, brain, prostate, spleen, pancreatic, cervical, ovarian, head and neck, esophageal, liver, skin, kidney, leukemia, bone, testicular, colon, or bladder cancers. For example, there is provided a method for treating a skin cancer, such as a melanoma, by administration of a serine protease targeted to skin cancer cells. Likewise, there is provided a method for treating a gp240 positive skin cancer comprising administering a serine protease of the embodiments that comprises a scFvMEL targeting moiety.

In some cases, cell-targeting constructs of the embodiments can used in conjunction with a further (e.g., a second) anticancer therapy. Thus, in certain instances, there is provided a method sensitizing cells to an anticancer therapy (e.g., a chemotherapy) by administering a cell targeting construct comprising a serine protease conjugated to a cell targeting moiety. In this case the cell targeting construct may be administered prior to, concurrently with, or after administration of the anticancer therapy. For example, the anticancer therapy can be a surgical therapy, chemotherapy, radiation therapy, gene therapy or immunotherapy. In some aspects, if the anticancer therapy is a chemotherapy, in may be preferred that the chemotherapy comprise one or more apoptosis inducing agents.

In yet further aspects of the embodiments there is provided a method for treating an autoimmune disease or an inflammatory disease comprising administering a cell targeting construct according the embodiments. For example, cell targeted-serine protease may be used in the treatment of rheumatoid arthritis, psoriasis, osteoarthritis, inflammatory bowel disease, type 1 diabetes, tissue or organ rejection or multiple sclerosis. In these aspects, cell targeting constructs may be used in combination with other treatment regimens, such as steroids.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-C: Graphic alignments of various mammalian granzyme polypeptides and serine proteases having high homology to granzymes. In each case the polypeptide sequences provided are for the mature active polypeptide (i.e., lacking the N-terminal leader sequence). (A) Figure shows an alignment of sequences for GrB from *Homo sapiens* (SEQ ID NO: 1; 100%); *Pan troglodytes* (SEQ ID NO: 2; 98%); *Pan paniscus* (SEQ ID NO: 3; 98%); *Pongo abelii* (SEQ ID NO: 4; 93%); *Macaca nemestrina* (SEQ ID NO: 5; 87%); *Macaca mulatta* (SEQ ID NO: 6; 87%); *Macaca fascicularis* (SEQ ID NO: 7; 86%); *Sus scrofa* (SEQ ID NO: 8; 72%); *Bos taurus* (SEQ ID NO: 9; 72%); *Rattus norvegicus* (SEQ ID NO: 10; 70%); and *Mus musculus* (SEQ ID NO: 11; 71%). Percent values in parenthesis indicate the percent identity to mature *H. sapiens* GrB. The amino acid positions corresponding to human GrB Asp 37, Asn 51, Asn84, Asp150, and Cys210 are each indicated in bold and shaded. * next to *H. sapiens* indicates that certain sequence reads for GrB indicate a "Q" at position 35 rather than the "R" depicted, see e.g., NCBI accession nos. AAA75490.1 versus EAW66003.1. (B) Figure shows an alignment of sequences for various mature Granzyme polypeptides from *Homo sapiens*. Sequences are shown for granzyme B "Gzm B" (SEQ ID NO: 1), granzyme A "Gzm A" (SEQ ID NO: 46), granzyme H "Gzm H" (SEQ ID NO: 47), granzyme K "Gzm K" (SEQ ID NO: 49) and granzyme M "Gzm M" (SEQ ID NO: 49). (C) Figure shows an alignment of sequences for serine protease polypeptides from *Homo sapiens* with high homology to granzyme polypeptides. Sequences are shown for mature granzyme B (SEQ ID NO: 1), Cathepsin G (SEQ ID NO: 50, NCBI accession no. P08311), Chymase (SEQ ID NO: 51, NCBI accession no. P23946), Myeloblastin (SEQ ID NO: 52, NCBI accession no. P24158), Kallikrein-14 (SEQ ID NO: 53, NCBI accession no. Q9P0G3), Complement factor D (SEQ ID NO: 54, NCBI accession no. K7ERG9), PRSS3 protein (SEQ ID NO: 55, NCBI accession no. A1A508), Trypsin-1 (SEQ ID NO: 56, NCBI accession no. P07477), Serine protease 57 (SEQ ID NO: 57, NCBI accession no. Q6UWY2) and PRSSL1 protein (SEQ ID NO: 58, NCBI accession no. B7ZMF6). In the alignments "*" indicated identical amino acid positions, ":" and "." indicate highly similar or similar amino acid positions respectively.

FIG. 2A-E: GrB polypeptides and constructs of the embodiments. A, Schematic showing general designs for GrB fusion constructs. The positions of membrane translocation peptides (MTP), endosomal cleavage peptides (ECP), cytosolic cleavage peptides (CCP), and cell penetrating peptides (CPP) are indicated. B, Schematic showing example GrB polypeptides that can be used for chemical conjugation. Substitutions in GrB are indicated in each case (A, C210A; N1, D150N; d1; N51S; and d2 N84A). For construct "CM": "R to A" indicates substitutions R96A, R100A, and R102A; "R to K" indicates substitution R201K; and "K to A" indicates substitutions K221A, K222A, K225A, and R226A. C-E, Schematics showing the designs of 50 GrB targeting constructs.

FIG. 7A-C: Effects of immunoGrB on apoptotic pathways of BT474 M1 parental, Herceptin resistant (HR), and Lapatinib resistant (LR) cells. A, Detection of apoptosis of GrB/4D5/26 by Annexin V/PI staining assay. Me180 cells served as a Her2/neu-negative control group. B, Western blot analysis of cleavage and activation of caspases-3 and -9 as well as PARP by GrB-based fusion constructs. C, Western blot investigation of apoptosis kinetics and specificity of GrB/4D5/26. Cells were treated with GrB/4D5/26 for up to 24 h with or without 100 µM zVAD-fmk for 24 h in parental or HR cells and for up to 48 h in LR cells.

FIG. 8A-B: Effects of immunoGrB on the mitochondrial pathway in BT474 M1 parental, HR, and LR cells. A, Effects of GrB-based fusion proteins on the upstream components Bcl-2 and BID in the mitochondrial pathway. B, Effects of immunoGrB on cytochrome c release and Bax translocation.

FIG. 10A-C: Tumor apoptotic activity of GrB/4D5/26 in BT474 M1 tumor xenografts. A, Mice with BT474 M1 flank tumors were intravenously injected with saline or 44 mg/kg GrB/4D5/26 at the indicated times (arrows). Mean tumor volume was calculated as WxLxH as measured with digital calipers. B, Immunofluorescence staining of tumor samples after i.v. injection of saline and GrB/4D5/26. Twenty four hours after injection, animals were sacrificed and frozen tumor sections were prepared and detected by anti-GrB antibody (green) and anti-mouse CD31 antibody (red). Hoechst 33342 (blue) was used for DNA staining. C, Apoptosis detection in tumor tissue by TUNEL assay.

DESCRIPTION OF ILLUSTRATIVE EMBODIMENTS

I. The Present Invention

Figure 2A:
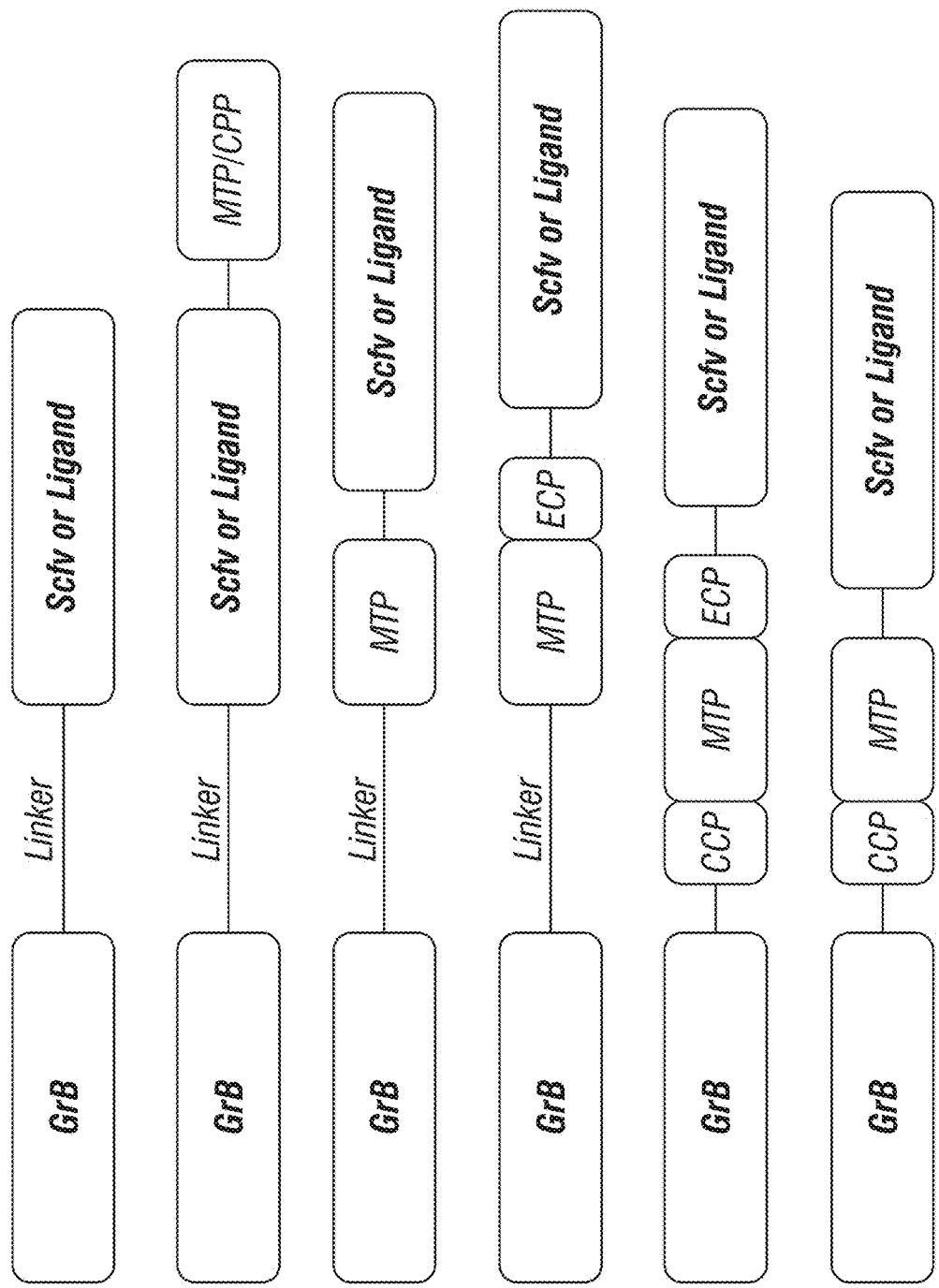
Figure 2B:
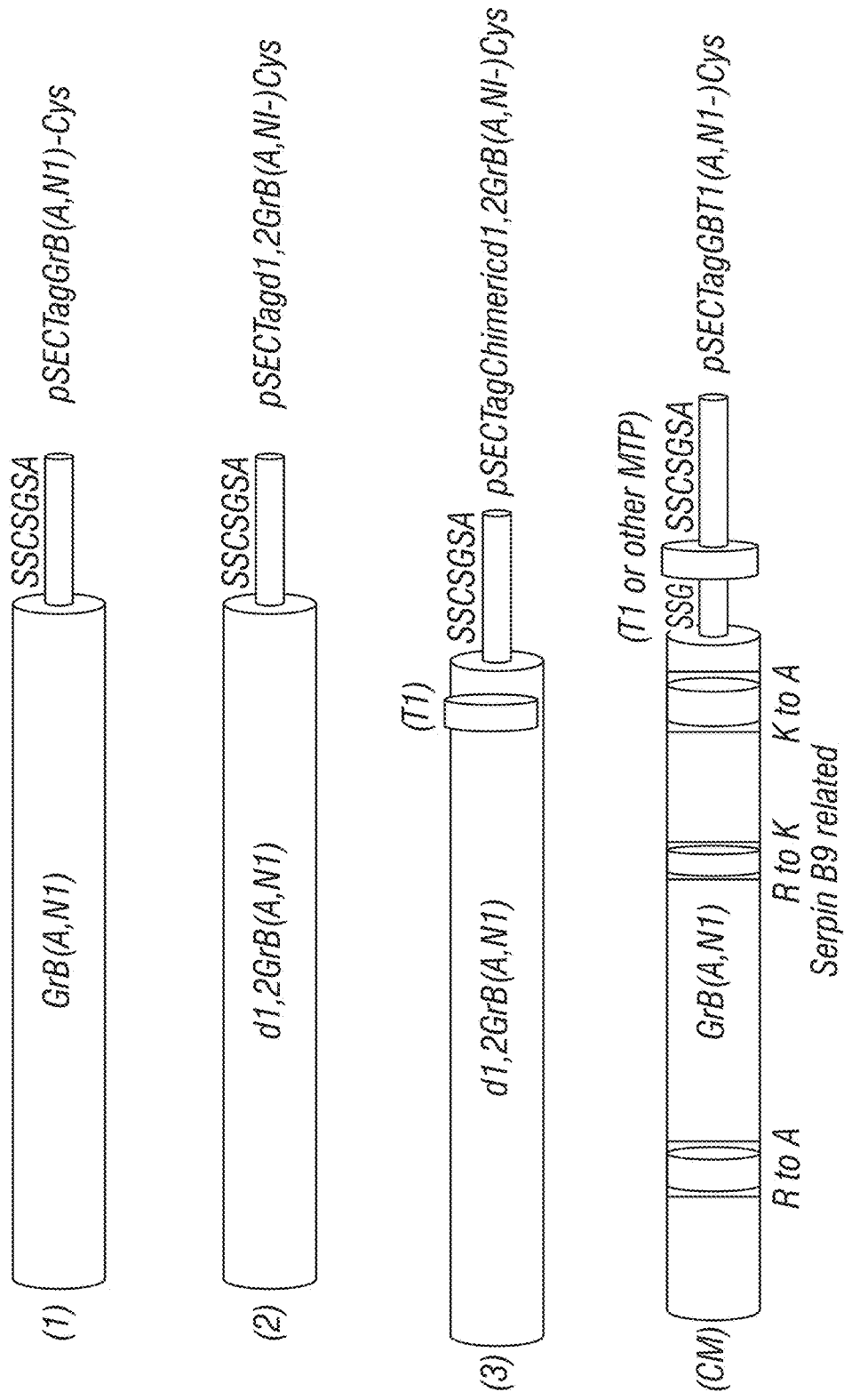
Figure 2C:
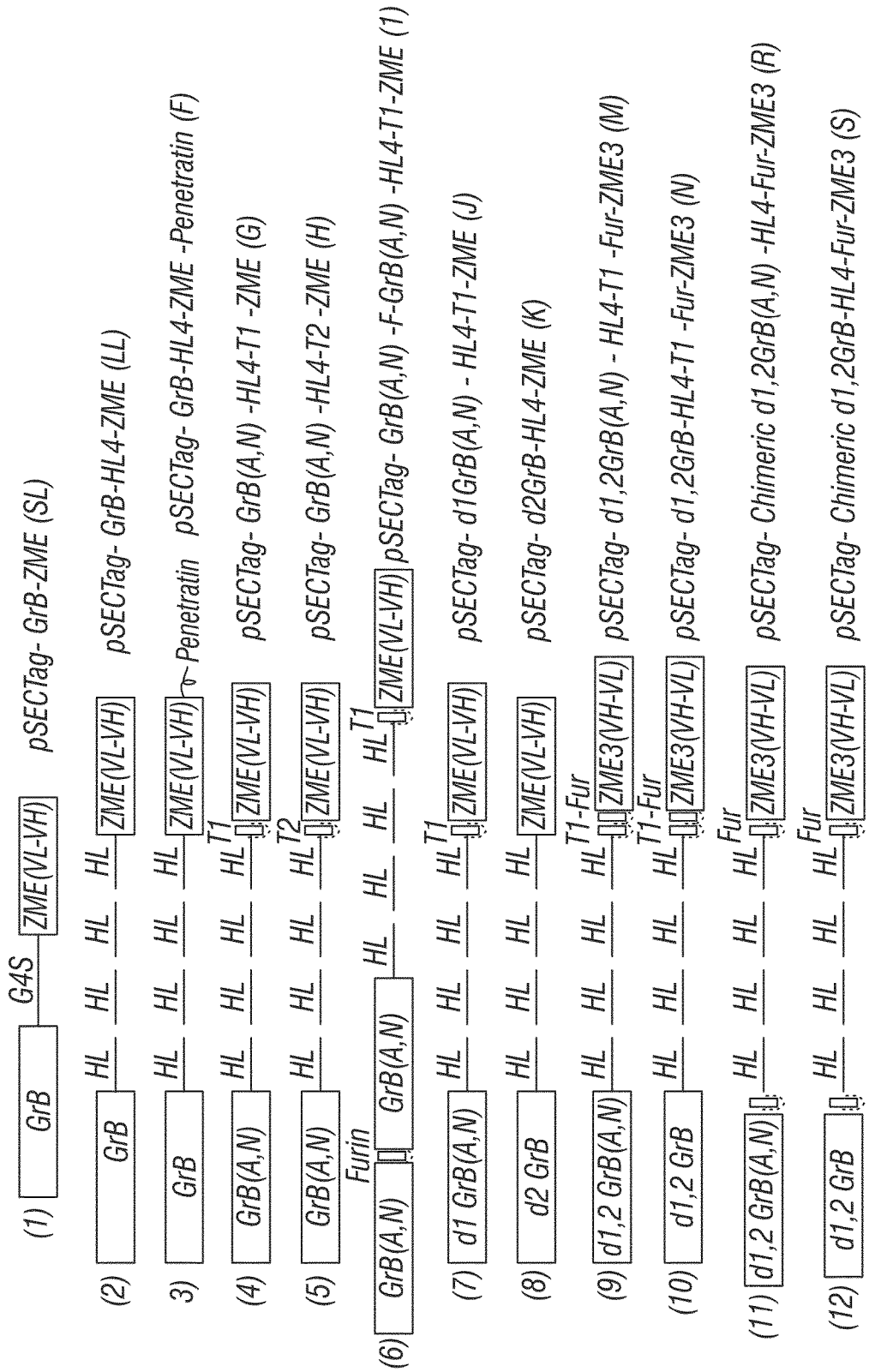
Figure 2C:
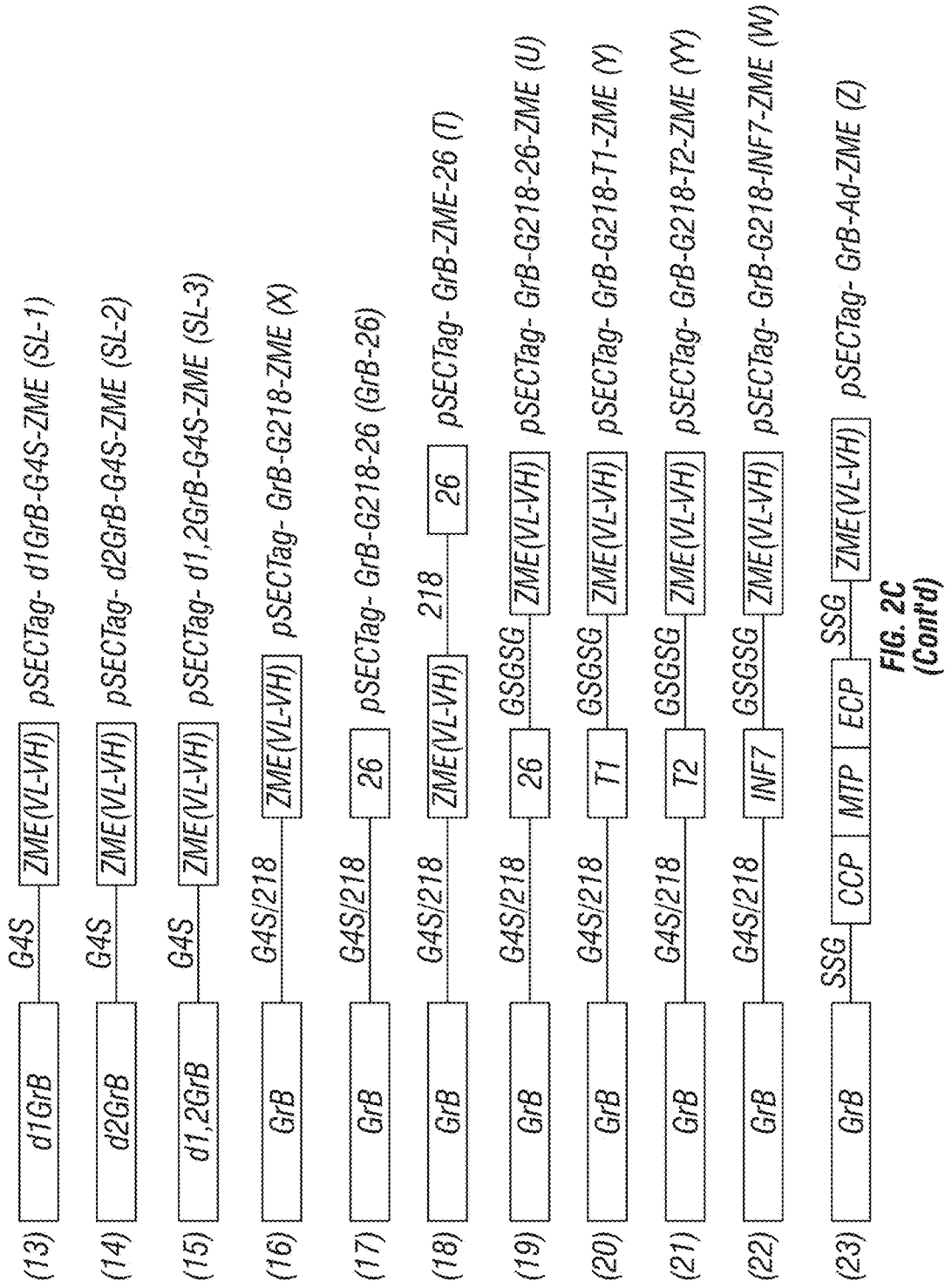
Figure 2D:
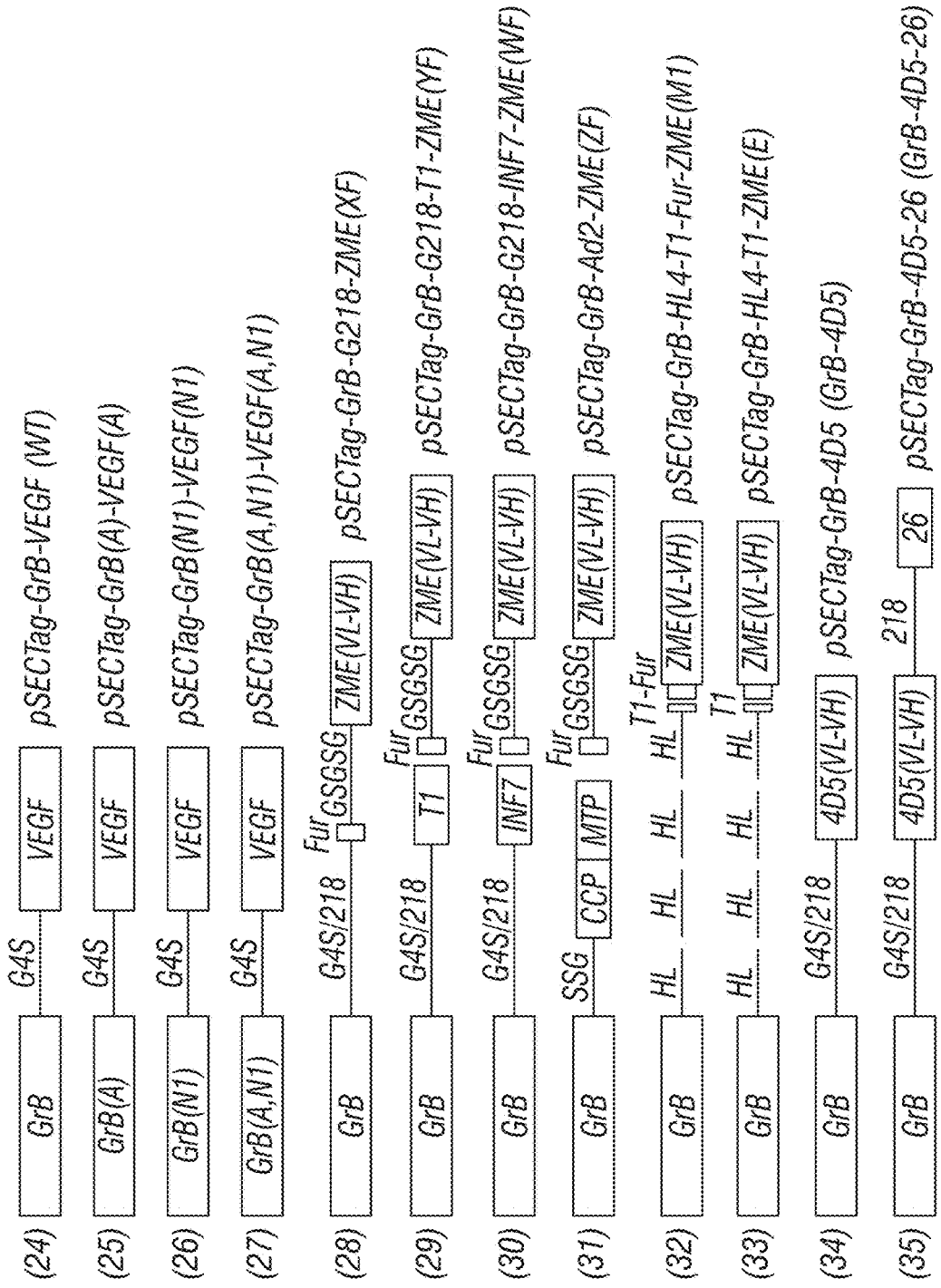

Recently, targeted cancer therapies have been developed for treating various malignancies. By virtue of their cell targeting specificity these agents can be both more effective and result in fewer side effects as compared to conventional therapy, such as chemotherapy. However, even such targeted therapies often do not have a sufficiently high specific activity to effectively kill a substantial proportion of the targeted cancer cells in patient. Likewise, even targeted therapies are often not sufficiently specific so as to avoid side effects that may result from killing of non-targeted cells in a patient. New therapeutics and methods provided herein address both of these deficiencies by providing cell-targeting constructs that are both highly toxic and highly specific to targeted cell populations.

As demonstrated herein the GrB "payload" polypeptides that are provided herein have both improved stability and activity. Each of the attributes results in an increased toxicity of the GrB payload to targeted cells. Moreover because of the enhanced specific activity of the GrB molecules, lower dosages may be effective for therapy thereby reducing possible toxic side effects of targeted therapies. In particular, recombinant GrB polypeptides of the embodiments comprise one or more of the following features: (a) an amino acid substitution or deletion at the position corresponding to Asp 37; (b) an amino acid substitution or deletion at the position corresponding to Asp 150; (c) an amino acid substitution or deletion at the position corresponding to Asn 51; (d) an amino acid substitution or deletion at the position corresponding to Asn 84; and/or (e) an amino acid substitution or deletion at the position corresponding to Cys 210.

Thus, in some embodiments a recombinant Granzyme B (GrB) polypeptide having enhanced stability and activity is provided. In some aspects, such GrB polypeptides can be conjugated or fused to a cell-targeting moiety, such as the 4D5 or ZME antibodies, thereby providing a highly specific targeted cytotoxic construct. In such aspects, a method of targeted cancer therapy is provided that allows for specific targeted killing of cancer cells that express a given antigen while other cells are left intact. In preferred aspects, the GrB polypeptide and/or the targeting moiety are comprised of substantially human amino acid sequence, which does not produce a robust immune response when administered to a human subject. For example, a cell-targeting construct of the embodiments can comprise from N-terminus to C-terminus a recombinant GrB polypeptide; optionally a linker; a CPP (such as T1 or INF7); and a cell-targeting moiety (such as ZME). Such a cell-targeting construct is exemplified in Examples 4, 5, and 7. In each case, the constructs are shown to have highly specific and highly toxic activity relative to target cells.

In a further aspect, a cell-targeting construct of the embodiments comprises from N-terminus to C-terminus a serine protease polypeptide; optionally a linker; a cell-targeting moiety (such as 4D5); optionally a second linker; and a CPP (such as CPP 26). Such constructs are exemplified herein in Example 8 and 11 and demonstrate highly selective toxicity to Her2-expressing cells. Interestingly, when these constructs included a CPP domain, not only was their cytotoxicity relative to Her2-expressing cells greatly increased, but they remained highly effective even against cells that had acquired resistance to anti-Her2 therapies (see, e.g., the results shown in Table 12). Accordingly, the targeting agents provided here are even effective against classes of tumors that have acquired resistance to other therapeutics that target the Her2 receptor. These new constructs can therefore be used to treat Her-2 positive cancers that have acquired resistance to therapy or to prevent resistance from being acquired in the first place by replacing current therapeutics.

II. Serine Protease Polypeptides

Figure 1A:
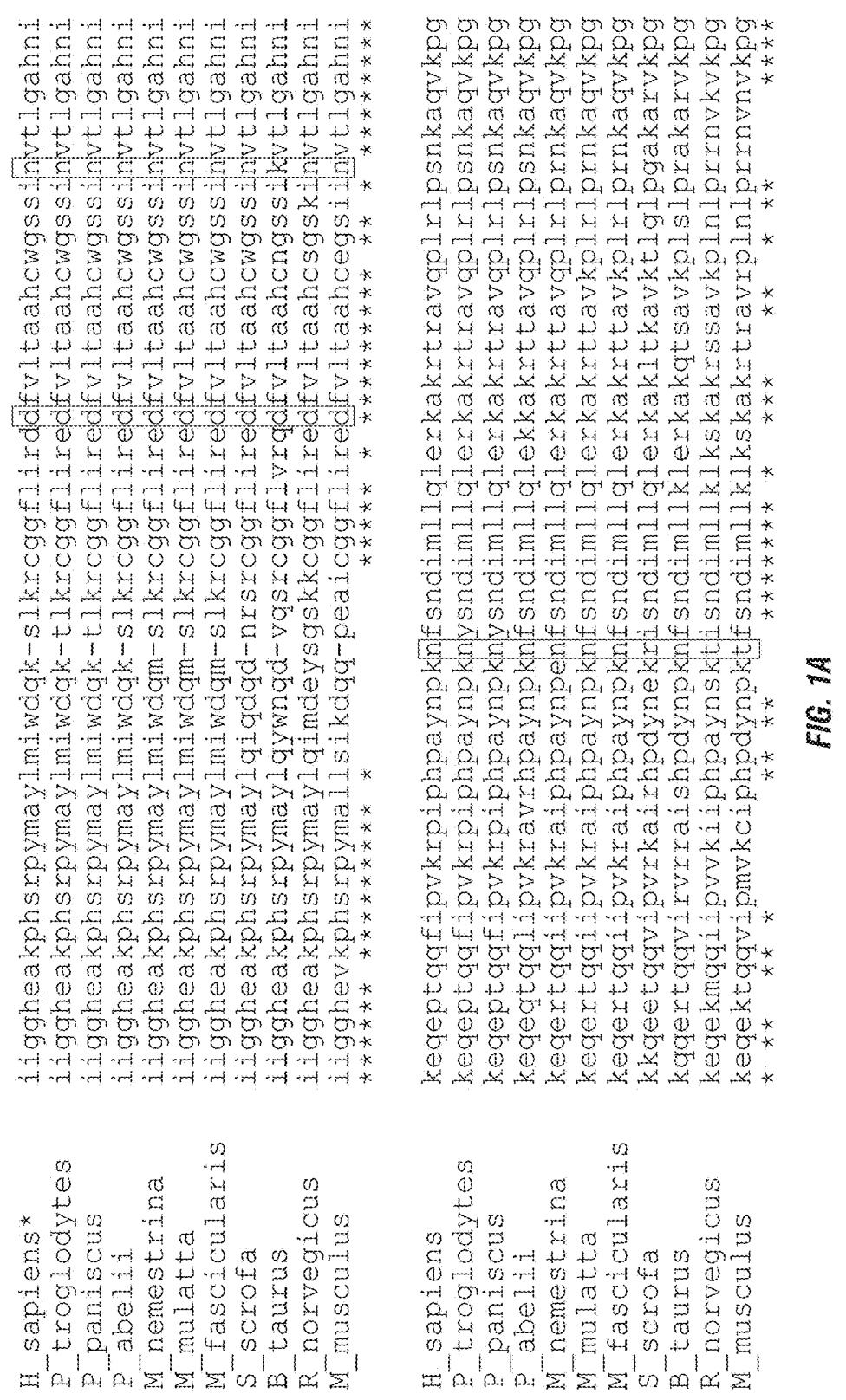

As described in the foregoing summary, certain aspects of the embodiments concern a cell targeting constructs that comprises a truncated serine protease, such as one of the polypeptides shown in FIG. 1. In preferred aspects, a serine protease for use according to the embodiments is a human or substantially human polypeptide. For example, the truncated serine protease can be a granzyme selected from granzyme B (SEQ ID NO: 1), granzyme A (SEQ ID NO: 46), granzyme H (SEQ ID NO: 47), granzyme K (SEQ ID NO: 49) or granzyme M (SEQ ID NO: 49), or a polypeptide at least about 80%, 85%, 90% or 95% identical to one these granzyme polypeptides. In still further aspects, the serine protease is a protease from *Homo sapiens* having a N-terminal amino acid sequence of IIGG, IVGG or ILGG (when in its mature, active form). For example, the serine protease can be Cathepsin G (SEQ ID NO: 50, NCBI accession no. P08311), Chymase (SEQ ID NO: 51, NCBI accession no. P23946), Myeloblastin (SEQ ID NO: 52, NCBI accession no. P24158), Kallikrein-14 (SEQ ID NO: 53, NCBI accession no. Q9POG3), Complement factor D (SEQ ID NO: 54, NCBI accession no. K7ERG9), PRSS3 protein (SEQ ID NO: 55, NCBI accession no. A1A508), Trypsin-1 (SEQ ID NO: 56, NCBI accession no. P07477), Serine protease 57 (SEQ ID NO: 57, NCBI accession no. Q6UWY2) or PRSSL1 protein (SEQ ID NO: 58, NCBI accession no.

B7ZMF6) or a polypeptide at least about 80%, 85%, 90% or 95% identical to one these protease polypeptides.

In certain very specific aspects, a serine protease for use according to the embodiments is a GrB polypeptide. Thus, one or more of the molecules for use in the current embodiments include, but are not limited to, human GrB (SEQ ID NO: 1) comprising one or more of the following features: (a) an amino acid substitution or deletion at the position corresponding to Asp 37; (b) an amino acid substitution or deletion at the position corresponding to Asp 150; (c) an amino acid substitution or deletion at the position corresponding to Asn 51; (d) an amino acid substitution or deletion at the position corresponding to Asn 84; and/or (e) an amino acid substitution or deletion at the position corresponding to Cys 210. For instance a GrB sequence for use according to the current embodiments may comprise a GrB polypeptide that at least 70%, 80%, 90%, 95%, 98% or more identical to human GrB. In certain aspects a recombinant GrB sequence is provided wherein one or more amino acid has been substituted for an amino acid at a corresponding position of GrB from another species (other than human).

In certain cases, serine protease polypeptides or portions thereof may be from a non-human source or may be from a homologous human polypeptide. For example, in the case of GrB, a polypeptide may comprise one or more amino acid substitutions to an amino acid at a corresponding position in a *Pan troglodytes* (SEQ ID NO: 2); *Pan paniscus* (SEQ ID NO: 3); *Pongo abelii* (SEQ ID NO: 4); *Macaca nemestrina* (SEQ ID NO: 5); *Macaca mulatta* (SEQ ID NO: 6); *Macaca fascicularis* (SEQ ID NO: 7); *Sus scrofa* (SEQ ID NO: 8); *Bos taurus* (SEQ ID NO: 9); *Rattus norvegicus* (SEQ ID NO: 10); or *Mus musculus* (SEQ ID NO: 11) GrB (see, FIG. 1A). Likewise, a granzyme polypeptide of the embodiments may comprise one or more amino acid substitutions to an amino acid at a corresponding position in a different granzyme coding sequence (see, e.g., FIG. 1B). In yet further aspects, a truncated serine protease of the embodiments may comprise one or more amino acid substitutions to an amino acid at a corresponding position in a different, homologous, serine protease coding sequence (see, e.g., FIG. 1C). Because of the high homology shared between these polypeptides, such substitutions for corresponding amino acid positions discussed above would be expected to result in a coding sequences that, when expressed, maintains protease activity.

In additional aspects, serine protease polypeptides may be further modified by one or more other amino substitutions while maintaining their enzymatic activity. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in GrB and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the GrB polypeptides described herein may be modified by the substitution of an amino acid, for different, but homologous amino acid with a similar hydrophilicity value. Amino acids with hydrophilicities within +/−1.0, or +/−0.5 points are considered homologous. Furthermore, it is envisioned that serine protease sequences may be modified by amino acid deletions, substitutions, additions or insertions while retaining its enzymatic activity.

III. Cell Targeting Moieties

As discussed above cell targeting moieties according to the embodiments may be, for example, an antibody, a growth factor, a hormone, a peptide, an aptamer or a cytokine. For instance, a cell targeting moiety according the embodiments may bind to a skin cancer cell such as a melanoma cell. It has been demonstrated that the gp240 antigen is expressed in a variety of melanomas but not in normal tissues. Thus, in certain aspects of the embodiments, there is provided a cell targeting construct comprising an GrB and a cell targeting moiety that binds to gp240. In some instances, the gp240 binding molecule may be an antibody, such as the ZME-018 (225.28S) antibody or the 9.2.27 antibody. In an even more preferred embodiment, the gp240 binding molecule may be a single chain antibody such as the scFvMEL antibody. Therefore, in a very specific embodiment of the invention, there is provided a cell targeting construct comprising human GrB conjugated to scFvMEL.

In yet further specific embodiments of the invention, cell targeting constructs may be directed to breast cancer cells. For example cell targeting moieties that bind to Her-2/neu, such as anti-Her-2/neu antibodies may conjugated to GrB. One example of such a cell targeting construct is a fusion protein comprising the single chain anti-Her-2/neu antibody scFv23 and GrB. Other scFv antibodies such as scFv(FRP5) that bind to Her-2/neu may also be used in the compositions and methods of the current embodiments (von Minckwitz et al., 2005).

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example are the cell targeting agents described in U.S. patent application no. 2004005647 and in Winthrop et al., 2003 that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy.

Since a large number of cell surface receptors have been identified in hematopoietic cells of various lineages, ligands or antibodies specific for these receptors may be used as cell-specific targeting moieties. IL2 may also be used as a cell-specific targeting moiety in a chimeric protein to target IL2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL4 receptor and may be targeted by moieties that bind these receptors, such as CD40 ligand, IL4, IL5, IL6 and CD28. The elimination of immune cells such as T cells and B cells is particularly useful in the treatment of autoimmunity, hypersensitivity, transplantation rejection responses and in the treatment of lymphoid tumors. Examples of autoimmune diseases are multiple sclerosis, rheumatoid arthritis, insulin-dependent diabetes mellitus, systemic lupus erythemotisis, scleroderma, and uviatis. More specifically, since myelin basic protein is known to be the major target of immune cell attack in multiple sclerosis, this protein may be used as a cell-specific targeting moiety for the treatment of multiple sclerosis (WO 97/19179; Becker et al., 1997).

Other cytokines that may be used to target specific cell subsets include the interleukins (IL 1 through IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that bind to the Fn14 receptor, such as TWEAK (see, e.g., Winkles 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Over the past few years, several monoclonal antibodies have been approved for therapeutic use and have achieved significant clinical and commercial success. Much of the clinical utility of monoclonal antibodies results from the affinity and specificity with which they bind to their targets, as well as long circulating life due to their relatively large size. Monoclonal antibodies, however, are not well suited for use in indications where a short half-life is advantageous or where their large size inhibits them physically from reaching the area of potential therapeutic activity.

Thus, in highly preferred embodiments, cell targeting moieties are antibodies or avimers. Antibodies and avimers can be generated to virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Applns. 20060234299 and 20060223114, each incorporated herein by reference.

Antibodies and Antibody-Like Targeting Moieties

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, deimmunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. In some aspects, the antibody can be a VHH (i.e., an antigen-specific VHH) antibody that comprises only a heavy chain. For example, such antibody molecules can be derived from a llama or other camelid antibody (e.g., a camelid IgG2 or IgG3, or a CDR-displaying frame from such camelid Ig) or from a shark antibody. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting.

As used herein, an "antibody fragment" includes a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

"Mini-antibodies" or "minibodies" are also contemplated for use with the present embodiments. Minibodies are sFv polypeptide chains which include oligomerization domains at their C-termini, separated from the sFv by a hinge region (Pack et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

In some cases antibody-like molecules are protein scaffolds that can be used to display antibody CDR domains. The origin of such protein scaffolds can be, but is not limited to, the structures selected among: fibronectin (see, e.g., U.S. Patent Publn. No. 20090253899, incorporated herein by reference) and preferentially fibronectin type III domain 10, protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat." The techniques for preparing and using various antibody-based constructs and fragments are well known in the art. Additional antibody-like molecules, such as anti-calins are described in detail in US Patent Publication Nos. 20100285564, 20060058510, 20060088908, 20050106660, PCT Publication No. WO2006/056464 and (Skerra, 2001), incorporated herein by reference.

Antibody-like binding peptidomimetics are also contemplated in the present embodiments. Liu et al. (2003) describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using such peptides are provided in U.S. Patent Publn. 20100317547, incorporated herein by reference.

Monoclonal antibodies (MAbs) are recognized to have certain advantages, e.g., reproducibility and large-scale production. Embodiments of the invention provide monoclonal antibodies of the human, murine, monkey, rat, hamster, rabbit and chicken origin. Due to the ease of preparation and ready availability of reagents, murine monoclonal antibodies will often be preferred.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. Methods for humanizing antibodies such as those provided here are well known in the art, see, e.g., Harvey et al., 2004, incorporated herein by reference.

IV. Fusion Proteins and Conjugates

A. Linkers

A variety of linkers can be used in truncated serine proteaseconstructs of the embodiments. In some aspects a linker can be a random string of one or more amino acids (e.g., 2, 3, 4, 5, 10, 15, 20 or more amino acids). Some specific linkers for use according the embodiments include the 218 (GSTSGSGKPGSGEGSTKG; SEQ ID NO: 13), the HL (EAAAK; SEQ ID NO: 14) and the $G_4S$ (GGGGS; SEQ ID NO: 15) linkers (e.g., Robinson et al., 1998; Arai et al., 2004 and Whitlow et al., 1993, each incorporated herein by reference).

In further aspects, a linker can serve as a way of separating different domains of a polypeptide construct, such as by proteolytic cleavage. For example, a linker region may comprise a protease cleavage site, such as the cleavage site recognized by an endogenous intracellular protease. In still further aspects, a protease cleavage site can be a site that is only cleaved in certain cell types (e.g., a site cleaved by a viral protease, such as HIV protease, which is only cleaved in infected cells). Example of protease cleavage site for use according to the embodiments include, without limitation, thrombin, furin (Goyal et al., 2000) and caspase cleavage sites.

The cell targeting constructs of the embodiments may be joined by a variety of conjugations or linkages that have been previously described in the art. In one example, a biologically-releasable bond, such as a selectively-cleavable linker or amino acid sequence may be used. For instance, peptide linkers that include a cleavage site for an enzyme preferentially located or active within a tumor environment are contemplated. For example, linkers that are cleaved by urokinase, plasmin, thrombin, Factor IXa, Factor Xa, or a metalloproteinase, such as collagenase, gelatinase, or stromelysin. In a preferred embodiment, a linker that is cleaved by an intracellular proteinase is preferred, since this will allow the targeting construct to be internalized intact into targeted cells prior to cleavage.

Amino acids such as selectively-cleavable linkers, synthetic linkers, or other amino acid sequences such as the glycine rich linkers are described above and may be used to separate proteinaceous components. In some specific examples linkers for use in the current embodiments include the 218 linker (GSTSGSGKPGSGQGSTKG) (SEQ ID NO: 13) or the $G_4S$ linker (GGGGS) (SEQ ID NO: 15). Additionally, while numerous types of disulfide-bond containing linkers are known that can successfully be employed to conjugate the GrB with a cell targeting moiety, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

B. Conjugates

Additionally, any other linking/coupling agents and/or mechanisms known to those of skill in the art can be used to combine the components of the present embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is contemplated that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Thorpe et al., 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

C. Cell Penetrating and Membrane Translocation Peptides

Furthermore, in certain aspects, library sequences can include segments of sequence that encode polypeptides having a known function, such as a cell-binding domain or cell penetrating peptide (CPP) in the ORF sequence along with sequence derived from cDNA or randomized sequence (i.e., to generate an ORF encoding a fusion protein). Thus, in certain aspects, DNA molecules of the embodiments comprise an ORF that comprises a CPP coding sequence along with a segment of library sequence (such as randomized sequence), 5' of the CPP coding sequence 3' of the CPP coding sequence or both. As used herein the terms "cell penetrating peptide" and "membrane translocation domain" are used interchangeably and refer to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ; SEQ ID NO: 18), herpes virus VP22, the *Drosophila* Antennapedia homeobox gene product, protegrin I, Penetratin (RQIKIWFQNRRMKWKK; SEQ ID NO: 16) or melittin (GIGAVLKVLTTGLPALISWIKRKRQQ; SEQ ID NO: 17). In certain aspects the CPP comprises the T1 (TKIESLKEHG; SEQ ID NO: 19), T2 (TQIENLKEKG; SEQ ID NO: 20), 26 (AALEALAEALEALAEALEALAE-AAAA; SEQ ID NO: 22) or INF7 (GLFEAIEGFIEN-GWEGMIEGWYGCG; SEQ ID NO: 21) CPP sequence.

V. Administration and Pharmaceutical Formulations

In some embodiments, an effective amount of a cell targeting construct is administered to a cell. In other embodiments, a therapeutically effective amount of the targeting construct is administered to an individual for the treatment of disease. The term "effective amount" as used herein is defined as the amount of the cell targeted truncated serine protease, such as GrB, of the present embodiments that is necessary to result in a physiological change in the cell or tissue to which it is administered either when administered alone or in combination with a cytotoxic therapy. The term "therapeutically effective amount" as used herein is defined as the amount of the targeting molecule of the present embodiments that eliminate, decrease, delay, or minimize adverse effects of a disease, such as cancer. A skilled artisan readily recognizes that, in many cases, cell targeted serine protease constructs may not provide a cure but may only provide partial benefit, such as alleviation or improvement of at least one symptom. In some embodiments, a physiological change having some benefit is also considered therapeutically beneficial. Thus, in some embodiments, an amount of cell targeted serine protease (e.g., GrB) that provides a physiological change is considered an "effective amount" or a "therapeutically effective amount." It will additionally be clear that a therapeutically effective amount may be dependent upon the inclusion of additional therapeutic regimens tat administered concurrently or sequentially. Thus it will be understood that in certain embodiments a physical change may constitute an enhanced effectiveness of a second therapeutic treatment.

The cell targeting constructs of the embodiments may be administered to a subject per se or in the form of a pharmaceutical composition for the treatment of cancer, autoimmunity, transplantation rejection, post-traumatic immune responses and infectious diseases, for example by targeting viral antigens, such as gp120 of HIV. More specifically, the chimeric polypeptides may be useful in eliminating cells involved in immune cell-mediated disorder, including lymphoma; autoimmunity, transplantation rejection, graft-versus-host disease, ischemia and stroke. Pharmaceutical compositions comprising the proteins of the embodiments may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

In preferred embodiments, cancer cells may be treated by methods and compositions of the embodiments. Cancer cells that may be treated with cell targeting constructs according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In preferred embodiments systemic formulations of the cell targeting constructs are contemplated. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. In the most preferred embodiments cell targeted serine protease is delivered by direct intravenous or intratumoral injection.

For injection, the proteins of the embodiments may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

A. Effective Dosages

The cell targeted serine protease of the embodiments will generally be used in an amount effective to achieve the intended purpose. For use to treat or prevent a disease condition, the molecules of the embodiments, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with serine protease constructs of the embodiments include, but are not limited to, steroid and non-steroid anti-inflammatory agents.

B. Toxicity

Preferably, a therapeutically effective dose of the cell targeted GrB described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

C. Pharmaceutical Preparations

Pharmaceutical compositions of the present embodiments comprise an effective amount of one or more chimeric polypeptides or chimeric polypeptides and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The cell targeted serine protease may comprise different types of carriers depending on whether it is to be administered in solid, liquid or aerosol form, and whether it need to be sterile for such routes of administration as injection. The present therapies of the embodiments can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present embodiments administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VI. Combination Therapies

In order to increase the effectiveness of a nucleic acid, polypeptide or nanoparticle complex of the present embodiments, it may be desirable to combine these compositions with other agents effective in the treatment of the disease of interest.

As a non-limiting example, the treatment of cancer may be implemented with a cell-targeted serine protease therapeutic of the present embodiments along with other anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the anti-cancer peptide or nanoparticle complex and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the anti-cancer peptide or nanoparticle complex and the other includes the second agent(s). In particular embodiments, an anti-cancer peptide can be one agent, and an anti-cancer nanoparticle complex can be the other agent.

Treatment with the anti-cancer peptide or nanoparticle-complex may precede or follow the other agent treatment by intervals ranging from minutes to weeks. In embodiments where the other agent and the anti-cancer peptide or nanoparticle complex are applied separately to the cell, one would generally ensure that a significant period of time did not expire between the time of each delivery, such that the agent and the anti-cancer peptide or nanoparticle complex would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly where several days (e.g., 2, 3, 4, 5, 6 or 7 days) to several weeks (e.g., 1, 2, 3, 4, 5, 6, 7 or 8 weeks) lapse between the respective administrations.

Various combinations may be employed, where the serine protease-based therapy is "A" and the secondary agent, such as radiotherapy, chemotherapy or anti-inflammatory agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In certain embodiments, administration of the GRB therapy of the present embodiments to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies. In some aspects a serine protease therapeutic of the embodiments is administered (or formulated) in conjunction with a chemotherapeutic agent. For example, in some aspects the chemotherapeutic agent is a protein kinase inhibitor such as a EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein tansferase inhibitors, transplatinum, and pharmaceutically acceptable salts, acids or derivatives of any of the above. In certain embodiments, the compositions provided herein may be used in combination with gefitinib. In other embodiments, the present embodiments may be practiced in combination with Gleevac (e.g., from about 400 to about 800 mg/day of Gleevac may be administered to a patient). In certain embodiments, one or more chemotherapeutic may be used in combination with the compositions provided herein.

B. Radiotherapy

Radiotherapy has been used extensively in treatments and includes what are commonly known as γ-rays, X-rays, and/or the directed delivery of radioisotopes to tumor cells. Other forms radiotherapy are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with a serine protease therapy of the present embodiments. The general approach for combined therapy is discussed below. Generally, the tumor cell must bear some marker that is amenable to targeting, i.e., is not present on the majority of other cells. Many tumor markers exist and any of these may be suitable for targeting in the context of the present embodiments. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a gene therapy in which a therapeutic polynucleotide is administered before, after, or at the same time as the therapeutic composition. Viral vectors for the expression of a gene product are well known in the art, and include such eukaryotic expression systems as adenoviruses, adeno-associated viruses, retroviruses, herpesviruses, lentiviruses, poxviruses including vaccinia viruses, and papiloma viruses, including SV40. Alternatively, the administration of expression constructs can be accomplished with lipid based vectors such as liposomes or DOTAP:cholesterol vesicles. All of these method are well known in the art (see, e.g. Sambrook et al., 1989; Ausubel et al., 1998; Ausubel, 1996).

Delivery of a vector encoding one of the following gene products will have a combined anti-hyperproliferative effect on target tissues. A variety of proteins are encompassed within the present embodiments and are well known in the art.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatments provided herein, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present embodiments may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

VII. Examples

The following examples are included to demonstrate preferred embodiments of the embodiments. It should be appreciated by those of skill in the art that the techniques disclosed in the examples which follow represent techniques discovered by the inventor to function well in the practice of the embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Testing of GrB-VEGF Fusion Constructs

Figure 3:
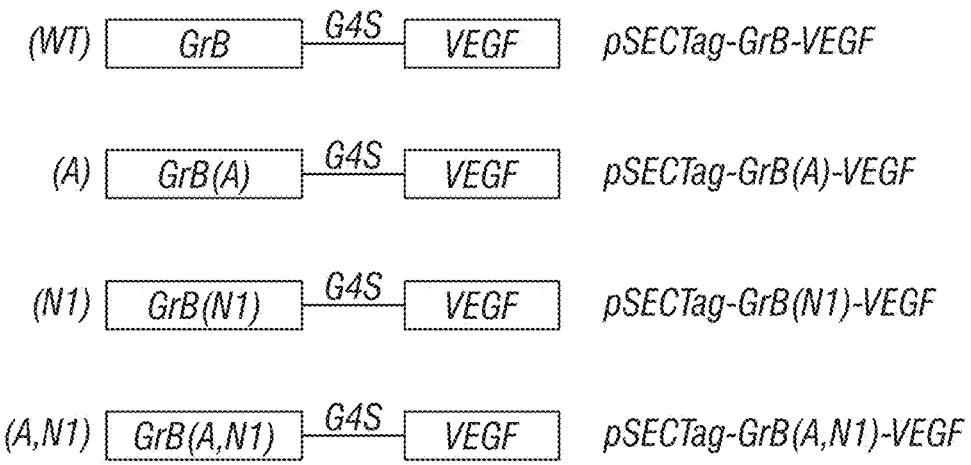
FIG. 3: Construction and testing of various fusion proteins comprising $VEGF_{121}$ and GrB. Upper panel shows a schematic of four different GrB-VEGF fusion proteins. GrB polypeptides are wild-type human sequence (WT), and in each case, GrB polypeptides are fused to $VEGF_{121}$ via a $G_4S$ linker sequence. The lower panel is a graph showing the GrB enzymatic activity of each of the fusion proteins.
Figure 3:
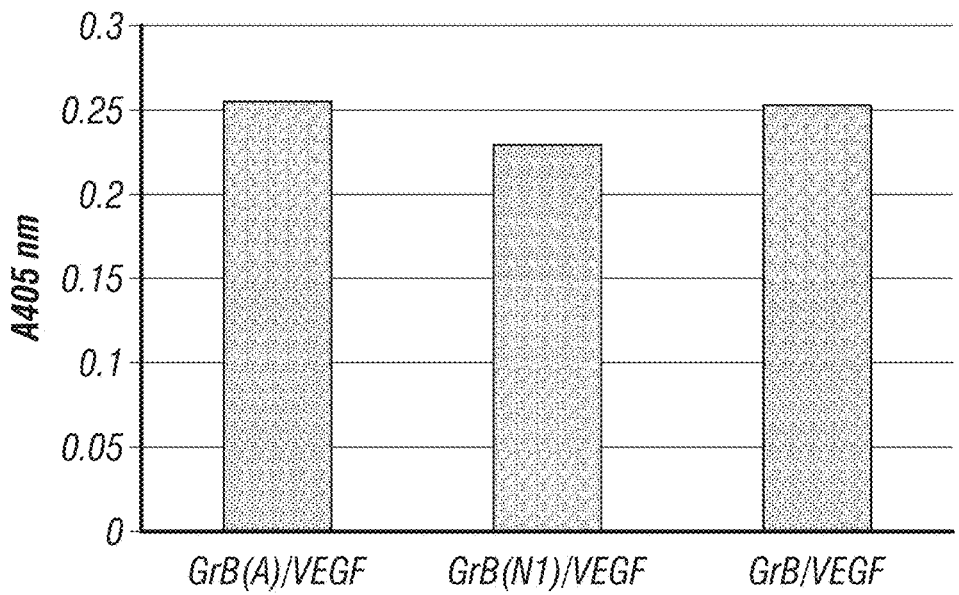

Four different fusion constructs were generated using wild-type (native) human GrB (WT), a mutant with the potential self-cleavage domain deleted (A), a mutant with one glycosylation domain mutated (N1) and a version combining the two mutations (A, N1). The constructs were generated by PCR, the mutations were confirmed by DNA sequencing and the proteins were transfected into mammalian expression cells. The proteins were expressed and purified. In vitro assays with the expressed polypeptides show similar levels for enzymatic activity (FIG. 3). The fusion proteins were then used to treat transfected endothelial cells expressing the VEGFR-2 receptor (PAE/VEGFR-2) or a control (PAE/VEGFR-1) cell line. Results of the studies are shown in Table 1. Values shown are the $IC_{50}$ values in nM.

TABLE 1

Cytotoxic effects of GrB/VEGF$_{121}$ fusion construct variants on transfected endothelial cells.

| Target cell | WT | A | N1 | A, N1 |
|---|---|---|---|---|
| PAE/VEGFR-2 (+) | 15.3 | 12.2 | 11.6 | 19.6 |
| PAE/VEGFR-1 (−) | >1000 | >1000 | >1000 | >1000 | values indicate $IC_{50}$ nM.

These studies showed that the above modifications had no effect on overall expression/yield of Granzyme B fusion proteins. The enzymatic and cytotoxic activity of the Granzyme B C210A mutation was similar to native Granzyme B. Thus, this mutant is a better candidate for Granzyme B chemical conjugation studies than native Granzyme B.

Example 2—Investigation of Linker Effects on GrB Activity

GrB-ZME(VL-VH) fusion proteins were constructed as indicated above using different linkers between the GrB and ZME sequences. The construct SL used the $G_4S$ linker; LL was four repeats of the HL (EAAAK) linker and X was a $G_4S$+218 linker. All linkers showed specific cytotoxic effects against target cells. The construct containing the shortest flexible linker demonstrated the best cytotoxicity (lowest $IC_{50}$) against target cells as shown in Table 2. Thus, the studies indicate that short linkers may produce more effective therapeutics.

TABLE 2

Cytotoxic effects of GrB/ZME fusion constructs relative to target cells. AAB-527 and A375-M were specifically targeted by ZME, whereas SKOV3 was a non-specific control.

| Target cell | SL | LL | X | GrB alone |
|---|---|---|---|---|
| AAB-527 | 544 | 817 | 1148 | >2000 |
| A375-M | 722 | 1124 | 2228 | >2000 |
| SKOV3 | 795 | 1667 | 2363 | >2000 | values indicate $IC_{50}$ (nM)

Example 3—Effect of GrB Glycosylation on Targeting Construct Activity

Figure 4:
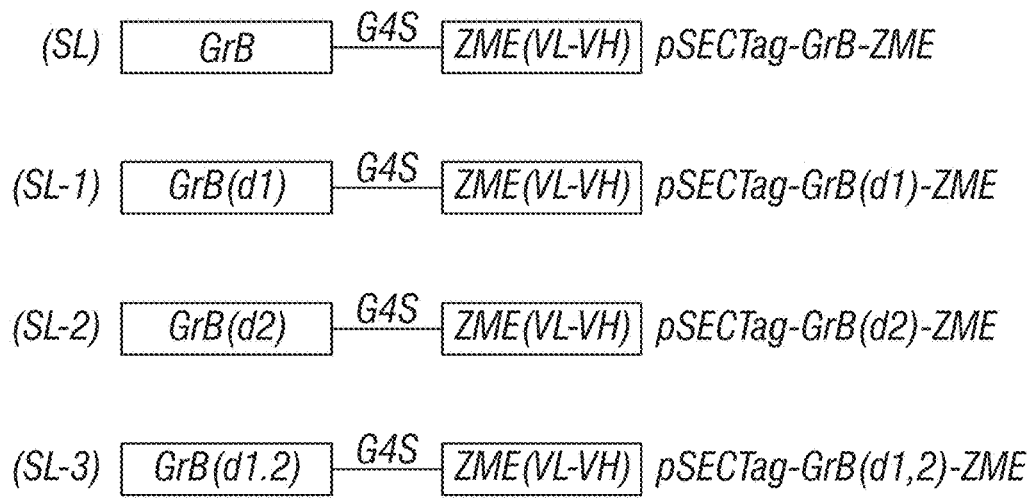
FIG. 4: Construction and testing of various fusion proteins comprising GrB and ZME(VL-VH). Upper panel shows a schematic of four different GrB-ZME fusion proteins. GrB polypeptides are wild-type human sequence (SL) or sequence with a substitution at N51S (d1/SL-1); N84A (d2/SL-2); or at both positions (d1,2/SL-3). In each case, GrB polypeptides are fused to ZME via a $G_4S$ linker sequence. The lower panel is a graph showing the GrB enzymatic activity of each of the fusion proteins that was expressed.
Figure 4:
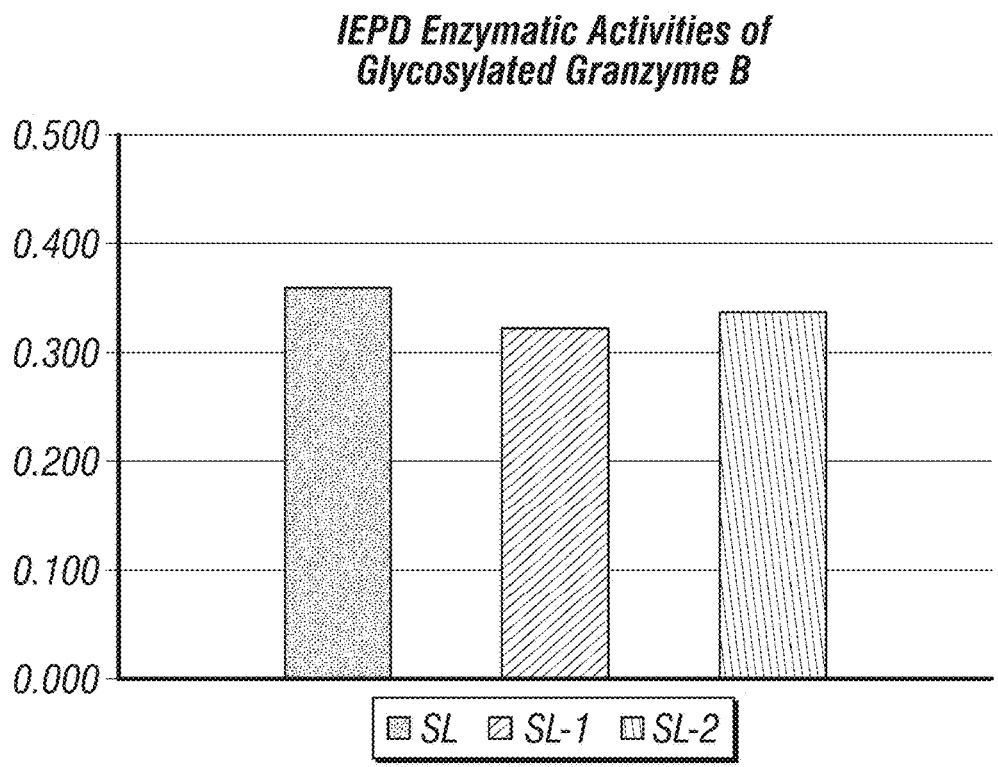

Two glycosylation sites were identified within the GrB molecule (d1 and d2) and modified the GrB/scFvMEL fusion construct as detailed above and as shown in FIG. 4 (d1 indicates N51S; d2 indicates N84A). Each glycosylation site was modified and then a molecule containing both modifications was generated. The individual modifications had little effect on in vitro GrB enzymatic activity (see, e.g., FIG. 4). However, as shown in Table 3, removal of each of the glycosylation sites generated a molecule with a lower $IC_{50}$ than the original wild-type-containing GrB. There was little impact on the non-specific cell line (SKOV3).

TABLE 3

Cytotoxic effects of GrB/ZME fusion constructs relative to target cells. SL is WT GrB, SL-1 includes the d1 mutation; SL-2 includes the d2 mutation; and SL-3 is d1 and d2. AAB-527 and A375-M were specifically targeted by ZME, whereas SKOV3 was a non-specific control.

| Target cell | SL | SL-1 | SL-2 | SL-3 |
|---|---|---|---|---|
| AAB-527 | 544 | 259 | 291 | * |
| A375-M | 722 | 216 | 438 | * |
| SKOV3 | 795 | 869 | 801 | * |

* values not determined due to low yield.
values indicate $IC_{50}$ (nM)

Example 4—Effect of GrB Glycosylation and T1 Translocation Domain on Targeting Construct Activity Three expression constructs were developed and tested. (LL) encoded GrB-HL-HL-HL-HL-ZME(VL-VH), plasmid designation pSECTag-GrB-HL4-ZME; (E) encoded GrB-HL-HL-HL-HL-T1-ZME(VL-VH), plasmid designation pSECTag-GrB-HL4-T1-ZME; and (J) (LL) encoded GrB (d1, A, N)-HL-HL-HL-HL-ZME(VL-VH), plasmid designation pSECTag-GrB-HL4-ZME. The constructs were expressed and tested. Results are shown in Table 4 and demonstrate that incorporation of the T1 domain increased the specific cytotoxicity of the construct against target cells but had no impact on non-specific toxicity. Incorporation of d1 modified GrB into the construct further increased the specific cytotoxicity of the construct with no impact on non-specific cytotoxicity. This result was particularly evident in the case of the constructs including the GrB (d1, A, N) polypeptide.

TABLE 4

Cytotoxic effects of various GrB/ZME fusion constructs with and without the T1 translocation domain.

| Target cell | LL | E | J |
|---|---|---|---|
| AAB-527 | 817 | 401 | 227 |
| A375-M | 1124 | 700 | 265 |
| SKOV3 | 1667 | 1765 | 1603 | values indicate $IC_{50}$ (nM).

Example 5—Effect of Linker Designs, Translocation Domains and/or Endosomal Cleavable Peptides on Targeting Construct Activity Further GrB expression constructs were developed and tested. (LL) encoded GrB-HL-HL-HL-HL-ZME(VL-VH), plasmid designation pSECTag-GrB-HL4-ZME; (E) encoded GrB-HL-HL-HL-HL-T1-ZME(VL-VH), plasmid designation pSECTag-GrB-HL4-T1-ZME; (M1) encoded GrB-HL-HL-HL-HL-T1-Fur-ZME(VL-VH), plasmid designation pSECTag-GrB-HL4-T1-Fur-ZME; (X) encoded GrB-G$_4$S/218-ZME(VL-VH), plasmid designation pSECTag-GrB-G218-ZME; (W) encoded GrB-G$_4$S/218-INF7-GSGSG-ZME(VL-VH), plasmid designation pSECTag-GrB-G218-INF7-ZME and (WF) encoded GrB-G$_4$S/218-INF7-Fur-GSGSG-ZME(VL-VH), plasmid designation pSECTag-GrB-G218-INF7-Fur-ZME.

These constructs were expressed and tested. Results shown in Table 5 demonstrate that addition of the Furin-cleavable site to the "E" molecule (M1) increased the sensitivity of both specific and non-specific cell lines. Incorporation of the INF7 peptide to improve translocation across the membrane greatly increased the sensitivity of target cells (constructs W and WF).

TABLE 5

Cytotoxic effects of various GrB/ZME fusion constructs with various linkers, translocation domains and cleavage sites.

| Target cell | LL | E | M1 | X | W | WF |
|---|---|---|---|---|---|---|
| AAB-527 | 817 | 401 | 253 | 1148 | 13 | 119 |
| A375-M | 1124 | 700 | 448 | 2228 | 134 | 279 |
| SKOV3 | 1667 | 1765 | 936 | 2363 | 102 | 663 | values indicate $IC_{50}$ (nM).

Example 6—Effect of C-Terminal Translocation Domains on Targeting Construct Activity Further GrB expression constructs were developed and tested. (LL) encoded GrB-HL-HL-HL-HL-ZME(VL-VH), plasmid designation pSECTag-GrB-HL4-ZME; (F) encoded GrB-HL-HL-HL-HL-ZME(VL-VH)-penetratin, plasmid designation pSECTag-GrB-HL4-ZME-Penetratin; and (T) encoded GrB-G$_4$S/218-ZME(VL-VH)-218-26, plasmid designation pSECTag-GrB-G218-ZME-26.

These constructs were expressed and tested. Results shown in Table 6 demonstrate that incorporation of Penetratin had no impact on the biological activity of the fusion construct. Incorporation of the "26" molecule increased the toxicity to target and non-target cells alike.

TABLE 6

Cytotoxic effects of various GrB/ZME fusion constructs with various C-terminal translocation domains.

| Target cell | LL | F | T |
|---|---|---|---|
| AAB-527 | 817 | 849 | 78 |
| A375-M | 1124 | 1159 | 24 |
| SKOV3 | 1667 | 1366 | 90 | values indicate $IC_{50}$ (nM).

Example 7—Effect of Different Membrane Translocation Peptides in the Same Relative Position on Targeting Construct Activity Further GrB expression constructs were developed and tested. (U) encoded GrB-G$_4$S/218-26-GSGSG-ZME(VL-VH), plasmid designation pSECTag-GrB-G218-26-ZME; (Y) encoded GrB-G$_4$S/218-T1-GSGSG-ZME(VL-VH), plasmid designation pSECTag-GrB-G218-T1-ZME; (YY) encoded GrB-G$_4$S/218-T2-GSGSG-ZME(VL-VH), plasmid designation pSECTag-GrB-G218-T2-ZME; and (W) encoded GrB-G$_4$S/218-INF7-GSGSG-ZME(VL-VH), plasmid designation pSECTag-GrB-G218-INF7-ZME.

These constructs were expressed and tested. Results shown in Table 7 demonstrate that constructs containing "26," T1, and T2 (U, Y and YY) were less toxic to target cells than to the non-specific cell line. Only construct W containing the INF7 membrane translocation peptide showed clear improvement in specificity.

TABLE 7

Cytotoxic effects of various GrB/ZME fusion constructs with various translocation domains.

| Target cell | U | Y | YY | W |
|---|---|---|---|---|
| AAB-527 | 131 | 486 | >2000 | 13 |
| A375-M | 29 | 364 | 240 | 134 |
| SKOV3 | 64 | 364 | 363 | 102 | values indicate $IC_{50}$ (nM).

Example 8—Specificity of Targeting Construct with and without Membrane Translocation Peptides Further GrB expression constructs were developed and tested. (GrB) encoded GrB, plasmid designation pSECTag-GrB; (GrB-26) encoded GrB-G$_4$S/218-26, plasmid designation pSECTag-GrB-G218-26; (GrB-4D5) encoded GrB-G$_4$S/218-4D5(V1-VH), plasmid designation pSECTag-GrB-4D5; and (GrB-4D5-26) encoded GrB-G$_4$S/218-4D5(VL-VH)-218-26, plasmid designation pSECTag-GrB-4D5-26.

These constructs were expressed and tested. Results shown in Table 8 demonstrate that the GrB/4D5 construct was not active on HER2 expressing target cells. Incorporation of the "26" translocation peptide restored sensitivity to HER2 positive cells but did not increase the cytotoxicity to HER2 negative cells.

TABLE 8

Cytotoxic effects of various GrB/4D5 fusion constructs with and without a translocation domain.

| Her2 Exp. | Cell line | GrB-4D5-26 | GrB-4D5 | GrB-26 | GrB |
|---|---|---|---|---|---|
| High | BT-474-M1 | 33 | >200 | >200 | >1000 |
| High | BT-474-M1(HR) | 27 | >200 | >200 | >1000 |
| High | Calu-3 | 10 | 96 | >200 | >1000 |
| High | NCI-N87 | 87 | >200 | >200 | >1000 |
| High | MDA-MB-453 | 25 | >200 | >200 | >1000 |
| High | SKBR3 | >200 | >200 | >200 | >1000 |
| High | SKOV3 | >200 | >200 | >200 | >1000 |
| none | Me-180 | >200 | >200 | >200 | >1000 | values indicate $IC_{50}$ (nM).

Example 9—Effect of an Endosomal Cleavage Peptide (ECP) on Targeting Construct Activity Further GrB expression constructs were developed and tested. (XF) encoded GrB-G$_4$S/218-Fur-GSGSG-ZME(VL-VH), plasmid designation pSECTag-GrB-G218-ZME; (UF) encoded GrB-G$_4$S/218-26-Fur-GSGSG-ZME(VL-VH), plasmid designation pSECTag-GrB-G218-26-Fur-ZME; (YF) encoded GrB-G$_4$S/218-T1-Fur-GSGSG-ZME(VL-VH), plasmid designation pSECTag-GrB-G218-T1-Fur-ZME; (WF) encoded GrB-G$_4$S/218-INF7-Fur-GSGSG-ZME(VL-VH), plasmid designation pSECTag-GrB-G218-INF7-ZME; and (ZF) encoded GrB-SSG-CCP-MTP-Fur-GSGSG-ZME(VL-VH), plasmid designation pSECTag-GrB-Ad2-ZME.

These constructs were expressed and tested. Results shown in Table 9.

TABLE 9

Cytotoxic effects of various GrB fusion constructs with furin cleavage sites.

| Target cell | XF | YF | WF | ZF | UF |
|---|---|---|---|---|---|
| AAB-527 | 166 | 95 | 119 | 88 | * |
| A375-M | 657 | 1057 | 279 | 164 | * |
| SKOV3 | 1547 | 1429 | 663 | 328 | * | values indicate $IC_{50}$ nM.
* values not determined due to low yield

Example 10—Assessment of Cytotoxic Activity of Further GrB Fusion Constructs

Further GrB expression constructs were developed and tested. (GrB) encoded GrB, plasmid designation pSECTag-GrB. (GrB-TWEAK) encoded GrB-G$_4$S-TNF-like weak inducer of apoptosis (TWEAK). These constructs were expressed and tested. Results of cytotoxicity studies are shown in Table 10.

TABLE 10

Cytotoxic effects of GrB versus GrB-TWEAK in various cell lines.

| Cell line | GrB-TWEAK | GrB |
|---|---|---|
| MDA-MB435/MDR1 | 0.4 | 447 |
| MDA-MB435 | 11 | 445 |
| AAB-527 | 4 | 1044 |
| SK-Mel-5 | 33 | 3014 |
| WM35 | 77 | >1923 |
| SB2 | 219 | >1923 |
| A375-M | 226 | >1923 |
| SK-Mel-1 | 330 | >1923 |
| SK-Mel-28 | 1720 | >1923 |
| MDA-MB231 | 15 | >1923 |
| SKBR3 | 64 | 660 |
| MCF-7 | 307 | >1923 |
| ES-2 | 67 | 1435 |
| OC-316 | 89 | >1923 |
| HeyA8 | 108 | 841 |
| HeyA8-MDR | 100 | >700 |
| A2780 | 263 | >1297 |
| HEY | 271 | 1015 |
| T-24 | 29 | 2631 |
| HT-29 | 23 | 800 |
| A172 | 55 | 1911 |
| HT-1080 | 72 | 1297 |
| BxPC-3 | 239 | >1923 |
| U87MG | 144 | 825 |
| Jurkat | >700 | >700 | values indicate $IC_{50}$ nM.

Example 11—Construction and Characterization of GrB Fusions Targeting Her2

Cell Lines and Cultures.

The cell lines BT474 M1, NCI-N87, Calu3, MDA MB435, and Me180 were all obtained from American Type Culture Collection (Manassas, Va.). The human breast cancer cell line MDA MB453 was generously supplied by Dr. Zhen Fan (The University of Texas MD Anderson Cancer Center, Houston, Tex.). The human breast cancer cell line eB-1 was kindly provided by Dr. Dihua Yu (The University of Texas MD Anderson Cancer Center, Houston, Tex.). BT474 M1 HR and LR cells were derived from BT474 M1 cells after a 12-month selection in the continuous presence of 1 μM Herceptin or 1.5 μM Lapatinib. BT474 M1 MDR-1 cells were generated by the transfection of plasmid pHaMDR1 to parental BT474 M1 cells. The HEK 293T cell line was supplied by Dr. Bryant G. Darnay (MD Anderson Cancer Center). All cell lines were maintained in Dulbecco's Modified Eagle Medium or RPMI 1640 medium supplemented with 10% heat-inactivated fetal bovine serum, 2 mM L-glutamine, and 1 mM antibiotics.

Construction, Expression, and Purification of GrB-Based Fusions.

The sequence of the humanized anti-Her2/neu scFv 4D5 was derived from the published Herceptin light- and heavy-chain variable domain sequences (Carter et al., 1992). Previous observations suggested that use of fusogenic peptides facilitates endosomal escape and delivery of large molecules into the cytosol (Plank et al., 1994; Bongartz et al., 1994). Therefore, the inventors incorporated the fusogenic peptide 26.

Figure 5A:
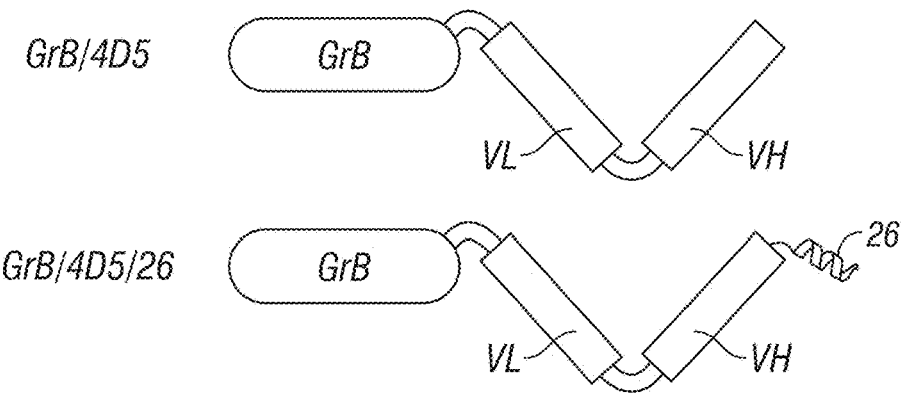
FIG. 5A-B: Construction and preparation of GrB-based fusion construct immunotoxins. A, Schematic diagram of immunoGrB constructs containing scFv 4D5 and GrB without or with fusogenic peptide 26. B, Purified immunoGrBs were analyzed by SDS-PAGE under reducing and non-reducing conditions.

The GrB/4D5/26, GrB/4D5, GrB/26, and GrB DNA constructs were generated by an overlapping polymerase chain reaction method. Illustrations of the constructs are shown in FIG. 5A. The inventors designed a universal 218 linker (GSTSGSGKPGSGEGSTKG; SEQ ID NO: 13) incorporated between the individual components of GrB, 4D5 (SEQ ID NO: 23), or peptide 26. Peptide 26 (AALEALAEALEALAEALEALAEAAAA; SEQ ID NO: 22) was generated from the 29-residue amphipathic peptide without the three C-terminal amino acids, which was responsible for dimerization (Turk et al., 2002). All construct genes were cloned into the mammalian cell expression vector pSecTag (Life Technologies, Carlsbad, Calif.).

A total of $3\times10^7$ HEK 293T cells were transfected using 50 µg of plasmid DNA and 150 µL (1 mg/mL) of polyethylenimine reagent, which were added to OPTI-MEM medium (Life Technologies) and incubated for 20 min at room temperature before the transfection mixture was added to the cells. After overnight incubation at 37° C., 100% humidity, and 5% $CO_2$, DMEM serum-free medium was added and the cells were incubated for a further 3 days. GrB-based protein samples were purified from cell culture supernatants by immobilized metal affinity chromatography, as previously reported (Cao et al., 2009). Activation of the protein was achieved by overnight incubation with recombinant enterokinase (Merck, Whitehouse Station, N.J.) according to the manufacturer's instructions. After dialysis against phosphate-buffered saline, the proteins were filter sterilized and stored at −80° C.

Figure 5B:
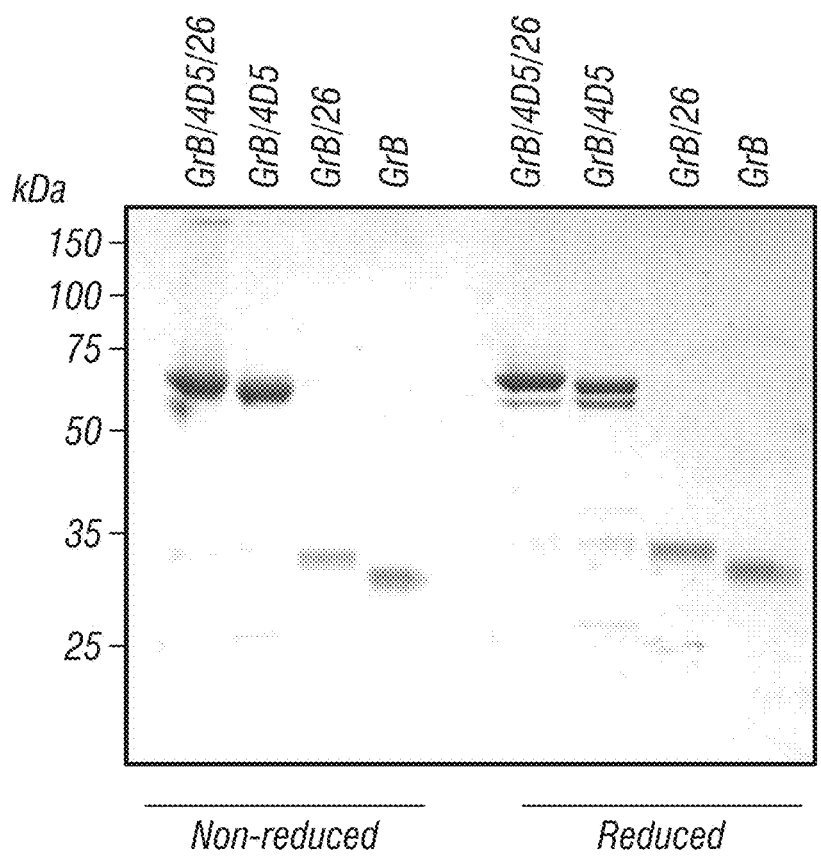

GrB-based fusions were generated by fusing GrB to 4D5 with (designated GrB/4D5/26; SEQ ID NO: 24) or without (designated GrB/4D5) the addition of pH-sensitive fusogenic peptide 26 to the C-terminal of the construct. Furthermore, GrB and GrB/26 were used as controls. All fusion proteins were expressed in human embryonic kidney cells (HEK 293T). Following purification, the final products migrated at the expected molecular weights, with a purity of >95% (FIG. 5B).

Analysis of Binding Affinity.

The $K_d$ value and specificity of GrB-based protein samples were evaluated by ELISA. Rabbit anti-c-myc antibody and horseradish peroxidase-conjugated goat anti-rabbit immunoglobulin G were used as tracers in this assay, as described previously (Cao et al., 2012).

Figure 6A:
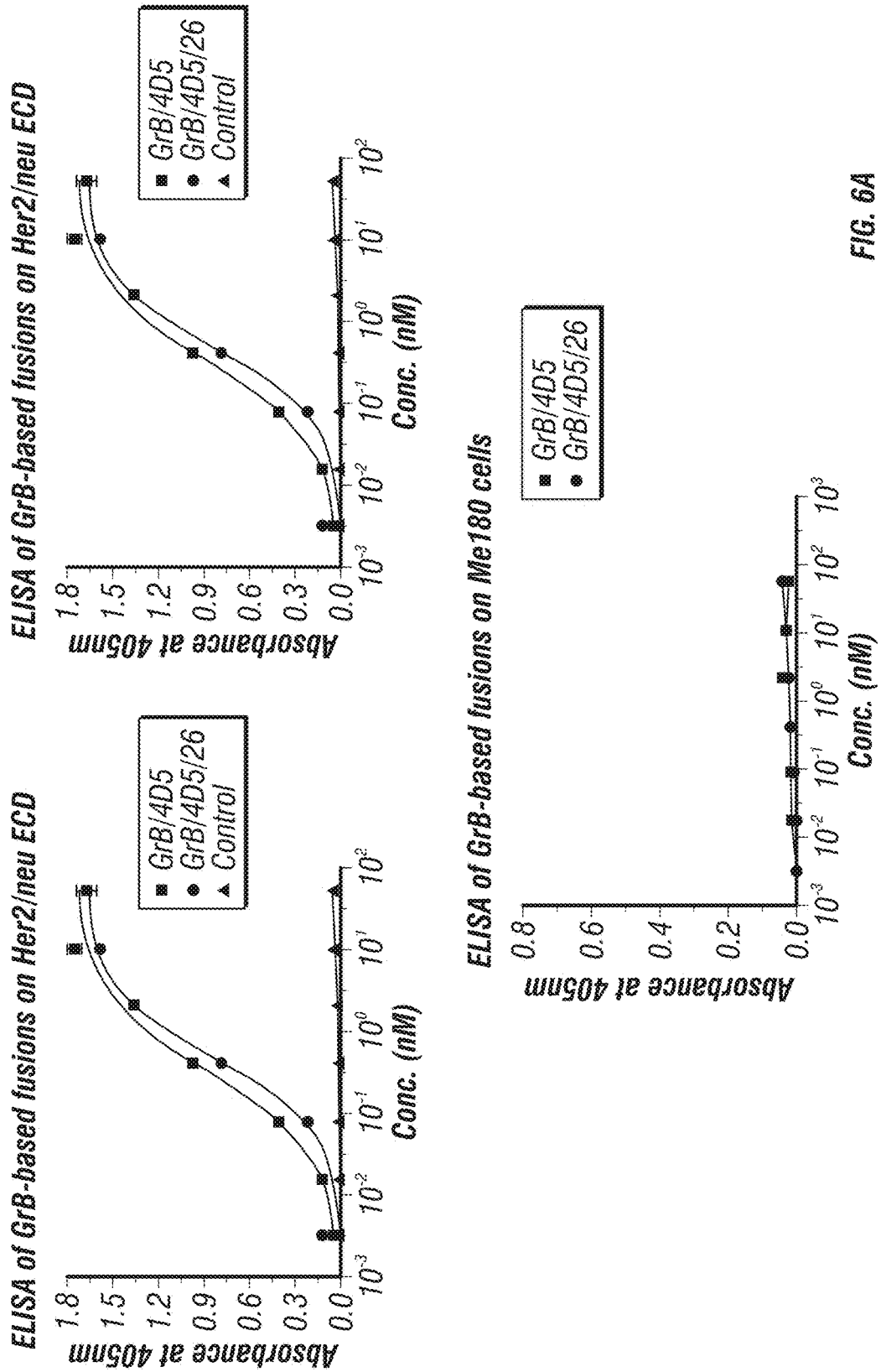
FIG. 6A-D: Characterization and comparison of GrB-based fusions. A, $K_d$ of immunoGrB constructs to Her2/neu ECD, Her2/neu-positive BT474 M1 cells, and Her2/neu-negative Me180 cells by ELISA. B, Enzymatic activity of GrB moiety of fusion proteins compared with native GrB. C, Internalization analysis of BT474 M1 cells and Me180 cells after 4 h of treatment with 25 nM immunotoxin. Cells were subjected to immunofluorescence staining with anti-GrB antibody (FITC-conjugated secondary), with PI nuclear counterstaining. D, Western blot analysis of the intracellular behavior of 25 nM immunoGrB in BT474 M1 cells.

The binding affinities ($K_d$ values) of GrB/4D5/26 and GrB/4D5 were assessed by ELISA using purified Her2/neu extracellular domain (ECD), Her2/neu-positive BT474 M1 human breast cancer cells, and Her2/neu-negative Me180 human cervical cancer cells. Both fusions specifically bound to Her2/neu ECD and BT474 M1 cells but not to Me180 cells (FIG. 6A). The apparent $K_d$ values were determined by calculating the concentration of fusion constructs that produced half-maximal specific binding. GrB/4D5 and GrB/4D5/26 demonstrated apparent $K_d$ values of 0.329 nM and 0.469 nM, respectively, to Her2/neu ECD and 0.383 nM and 0.655 nM, respectively, to BT474 M1 cells. These results are in general agreement with the published $K_d$ value for native Herceptin to the Her2/neu receptor (0.15 nM) (Carter et al., 1992).

Enzymatic Assay of GrB-Based Fusions.

The enzymatic activity of the GrB component was determined in a continuous colorimetric assay using N-α-t-butoxycarbonyl-L-alanyl-L-alanyl-L-aspartyl-thiobenzylester (BAADT) as a specific substrate (Liu et al., 2003). Assays consisted of commercial human GrB (Enzyme Systems Products, Livermore, Calif.) or GrB-based fusion proteins in BAADT at 25° C. The change in absorbance at 405 nm was measured on a Thermomax plate reader (Columbia, Md.). Increases in sample absorbance were converted to enzymatic rates by using an extinction coefficient of 13,100 $cm^{-1} M^{-1}$ at 405 nm. The specific activity of GrB-based fusion proteins was calculated using native GrB as the standard.

Figure 6B:
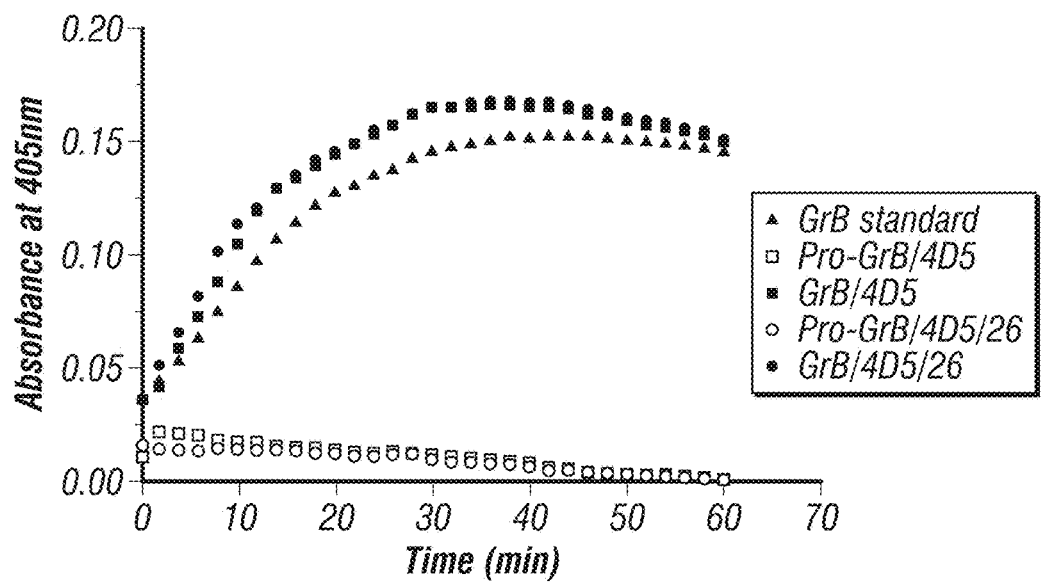

To assess the biological activity of the GrB component of the fusions, the inventors compared the ability of the constructs to cleave the substrate BAADT with that of native, authentic GrB (FIG. 6B). GrB/4D5 and GrB/4D5/26 had intact GrB enzymatic activity ($1.54\times10^5$ U/µmoL and $1.57\times10^5$ U/µmoL, respectively). These activities were comparable to that of the native GrB standard ($1.19\times10^5$ U/µmoL). Because the pro-GrB fusion constructs contain purification tags on the N-terminal end of GrB and render the molecule enzymatically inactive, these proteins were unable to cause hydrolysis of BAADT.

Cellular Uptake and GrB Delivery of Fusion Constructs.

Immunofluorescence-based internalization studies were performed using BT474 M1 and Me180 cells. Cells were treated with 25 nM GrB/4D5/26 for 4 h and subjected to immunofluorescent staining with anti-GrB antibody (fluorescein isothiocyanate [FITC]-conjugated secondary antibody). Nuclei were counterstained with PI. Visualization of immunofluorescence was performed with a Zeiss LSM510 confocal laser scanning microscope Zeiss LSM510 (Carl Zeiss, Thornwood, N.Y.).

Figure 6C:
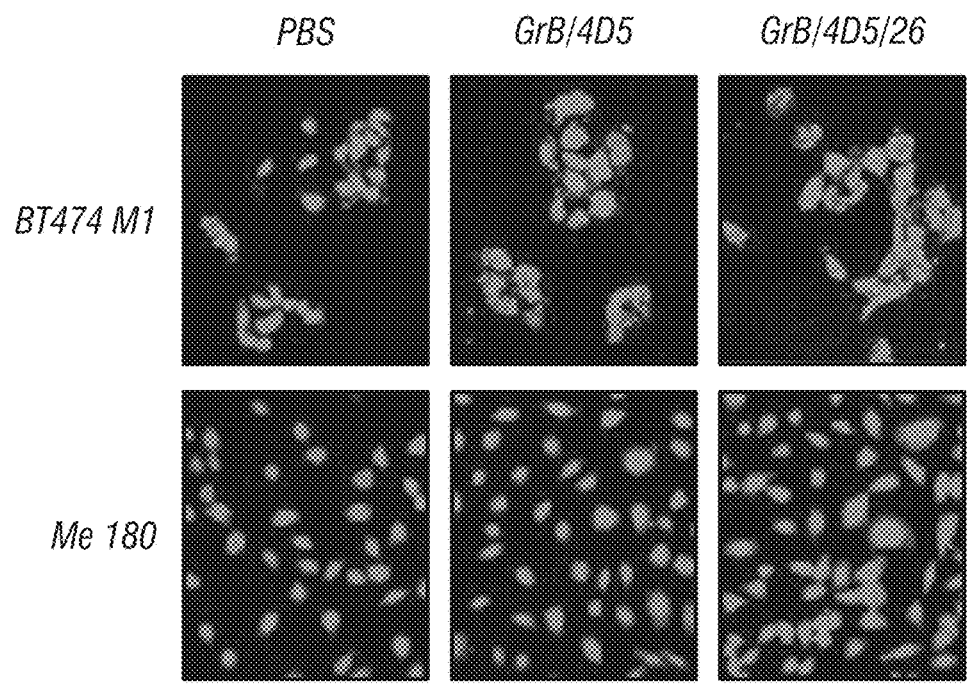
Figure 6D:
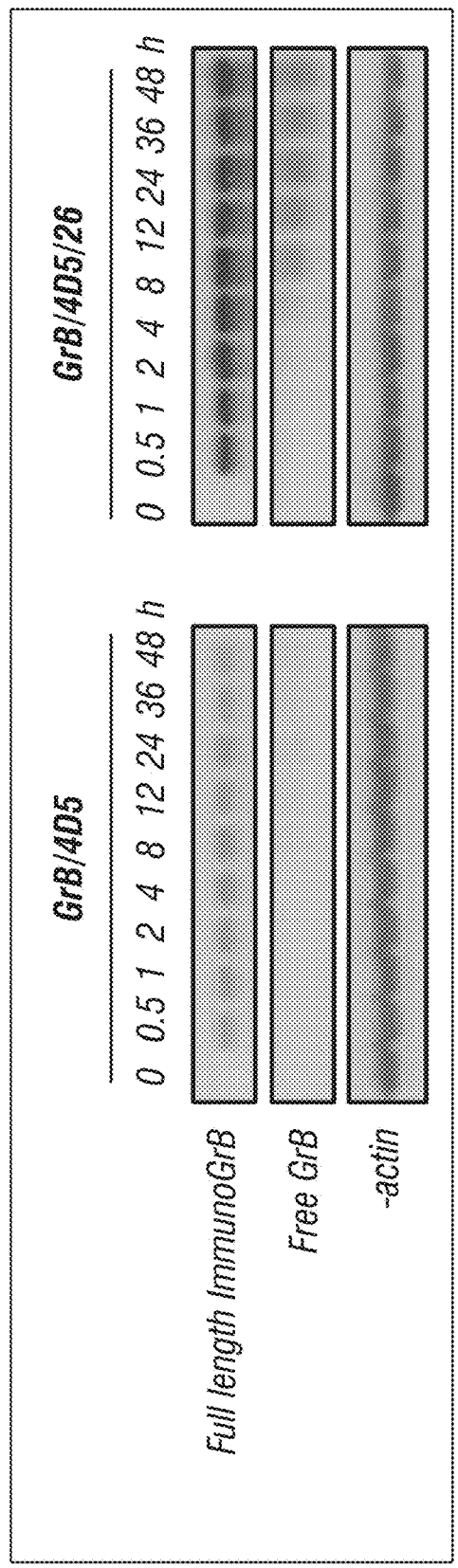

The GrB moiety of both fusions was observed primarily in the cytosol after treatment with a fusion protein in BT474 M1 cells but not in Me180 cells (FIG. 6C), demonstrating that both constructs were efficient in cell binding and internalization after exposure to Her2/neu-positive cells. The internalization efficiency of the fusions was further examined by time-dependent western blot analysis of the GrB signal (full-length GrB fusion+free GrB) (FIG. 6D). Both constructs internalized rapidly into BT474 M1 cells within 30 min. Compared with GrB/4D5, GrB/4D5/26 displayed enhanced and long-lasting cell internalization. The intracellular delivery of GrB after endocytosis of GrB/4D5 or GrB/4D5/26 also was assessed by time-dependent western blotting (free GrB). The inventors observed no GrB delivery by GrB/4D5 up to 48 h of treatment, whereas GrB delivery by GrB/4D5/26 was observed starting at approximately 4 h of treatment and presented a tremendously high level of free GrB up to 48 h (FIG. 6D).

In Vitro Cytotoxic Effects of GrB-Based Fusions.

Log-phase cells were seeded ($\sim5\times10^3$ cells per well) in 96-well plates and allowed to attach overnight. Cells were further incubated with various concentrations of GrB-based fusion proteins, GrB, or medium at 37° C. for 72 h. Cell viability was determined using the crystal violet staining method followed by solubilization of the dye in Sorenson's buffer as described previously (Cao et al., 2009).

Figure 11:
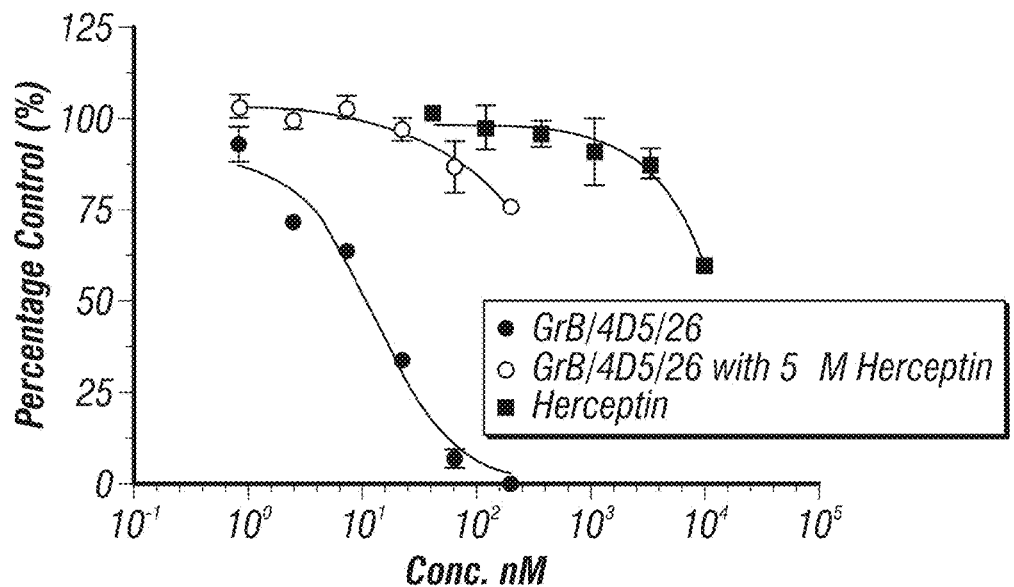
FIG. 11: Competitive cytotoxicity of GrB/4D5/26 with the addition of Herceptin against MDA MB453 cells. MDA MB453 cells were plated into 96-well plates and allowed to attach overnight. After that, the cells were treated with different concentrations of GrB/4D5/26, or pretreated with 5 µM Herceptin for 6 h and then co-treated with various concentrations of GrB/4D5/26. After 72 h, the cells were stained with crystal violet.

GrB-based fusions were tested against a number of tumor cell lines. After 72 h exposure, GrB/4D5/26 demonstrated specific cytotoxicity to Her2/neu-positive cells, with $IC_{50}$ values of less than 100 nM (Table 11), and GrB/4D5 demonstrated cytotoxic effects at somewhat higher doses (>200 nM). In addition, GrB/26 showed minimal cytotoxicity at doses >600 nM, but no significant activity of GrB itself was observed at doses up to 1.5 µM. When Her2/neu-positive MDA MB453 cells were pretreated with Herceptin (5 µM) for 6 h and then treated with GrB/4D5/26 for 72 h, the cytotoxicity of GrB/4D5/26 was reduced (FIG. 11), thereby demonstrating a requirement for antigen binding of the GrB/4D5/26 construct.

Figure 12:
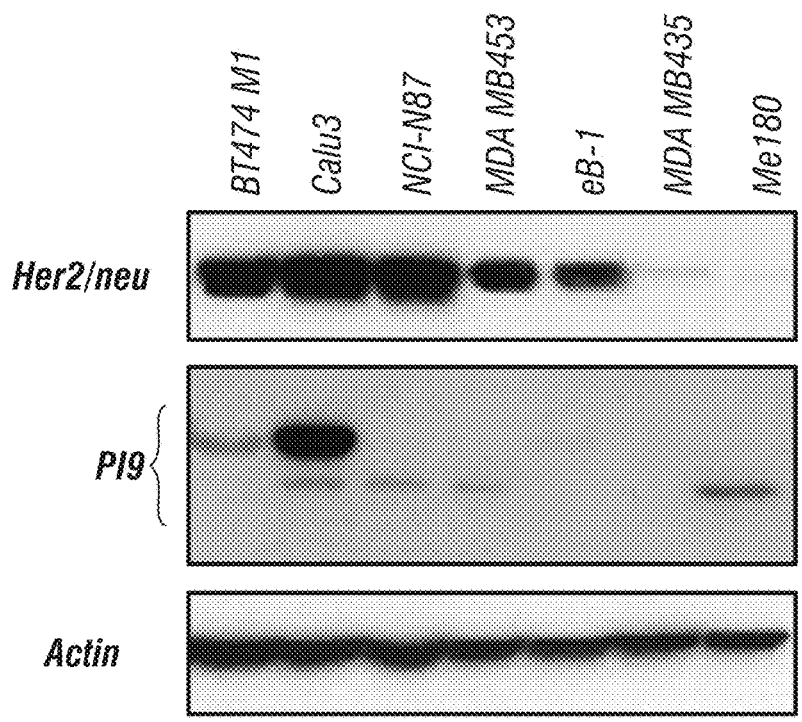
FIG. 12: Western blot analysis of the expression level of Her2/neu and PI-9 in a variety of cancer cells. Whole cell lysates (50 µg) were analyzed by SDS-PAGE and immunoblotted with anti-Her2/neu or anti-PI-9 antibodies, followed by incubation with horseradish peroxidase-labeled secondary antibodies and chemiluminescent detection. Actin was used as loading control.

The inventors further investigated the expression levels of the endogenous proteinase inhibitor 9 (PI-9) in different tumor cells (FIG. 12, Table 11). These studies failed to find an association between the response of cells to the cytotoxicity of the GrB constructs and the endogenous expression of PI-9. This may suggest that factors other than PI-9 may account for the observed differences in GrB/4D5/26 cytotoxicity to Her2/neu expressing target cells.

TABLE 11

Comparative $IC_{50}$ values of GrB-based fusion constructs against various types of tumor cell lines.

| Cell line | Type | Her2/neu level | PI-9 level | $IC_{50}$ (nM) GrB/4D5/26 | GrB/4D5 | GrB/26 | GrB |
|---|---|---|---|---|---|---|---|
| BT474 M1 | Breast | **** | * | 29.3 | 253.3 | 905.5 | >1500.0 |
| Calu3 | Breast | **** | ***** | 40.5 | 242.4 | 863.0 | >1500.0 |
| NCI-N87 | Gastric | **** | * | 90.4 | 629.0 | 1106.0 | >1500.0 |
| MDA MB453 | Lung | *** | * | 56.8 | 436.0 | 694.2 | >1500.0 |
| eB-1 | Breast | ** | — | 93.1 | 551.3 | 1134.5 | >1500.0 |
| MDA MB435 | Breast | * | — | >500.0 | >750.0 | 1031 | >1500.0 |
| Me180 | Cervical | * | * | >500.0 | >750.0 | >1500.0 | >1500.0 |

Cytotoxic Effects of GrB/4D5/26 Against Cells Resistant to Herceptin or Lapatinib.

Acquired resistance to Herceptin or Lapatinib can be mediated by concomitant upregulation of Her2/neu downstream signaling pathways or activation of signaling through the estrogen receptor (ER) pathway (Wang et al., 2011). In this study, the inventors developed a model of Herceptin-resistant (HR) and Lapatinib-resistant (LR) variants of BT474 M1 cells. Parental BT474 M1 cells were readily sensitive to both Herceptin ($IC_{50}$: 52.5 nM) and Lapatinib ($IC_{50}$: 34.7 nM) (Table 12). HR cells demonstrated resistance to Herceptin ($IC_{50}$: 10.1 µM, F.R.: 192) but remained sensitive to Lapatinib ($IC_{50}$: 32.4 nM). LR cells showed resistance to high micromolar concentrations of both Herceptin ($IC_{50}$: 74.1 µM, F.R.: 1411) and Lapatinib ($IC_{50}$: 8.2 µM, F.R.: 237). As shown in Table 12, cells resistant to Herceptin demonstrated equivalent sensitivity to the GrB/4D5/26 construct ($IC_{50}$~30 nM for both HR and parental BT474 M1 cells). For LR cells, the $IC_{50}$ was marginally increased (2-fold) compared to parental cells (66.1 nM vs. 32.9 nM, respectively).

The inventors also demonstrated that addition of epidermal growth factor (EGF) or neuregulin-1 (NRG-1) growth factor, but not β-estradiol, to BT474 M1 parental cells can circumvent the cellular cytotoxic responses to Herceptin and Lapatinib. Seventy-two hours of pretreatment of BT474 M1 cells with 20 ng/mL EGF or 50 ng/mL NRG-1 resulted in a 400~500 fold increase in resistance to Herceptin and a 16-fold increase in resistance to Lapatinib (Table 12). However, treatment of these resistant cells resulted in no cross-resistance to GrB/4D5/26 fusions compared with parental BT474 M1 cells.

Figure 13:
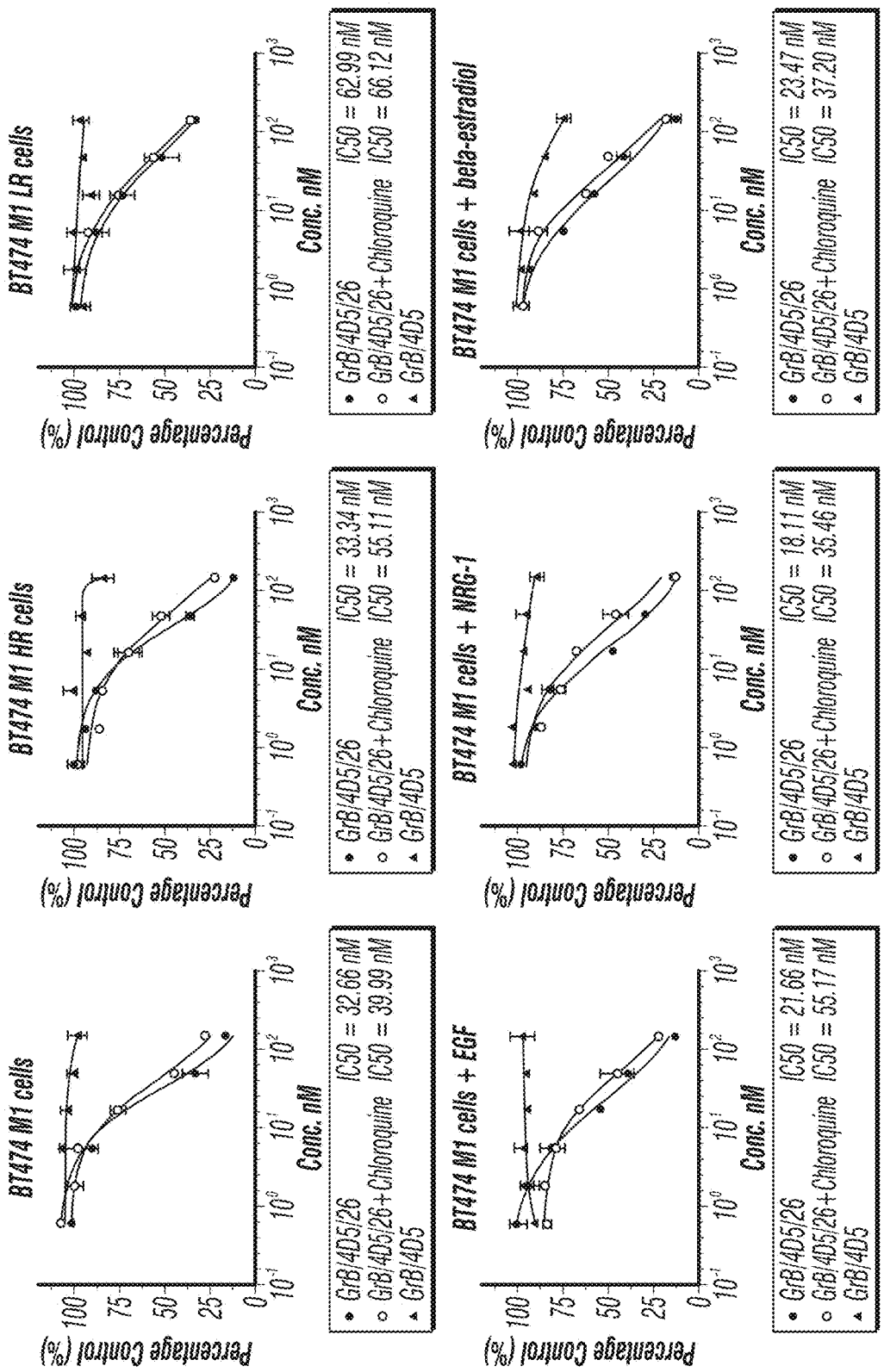
FIG. 13: The effect of the endosomolytic reagent chloroquine on the cell-killing activity of GrB/4D5/26. BT474 M1 and the derivatives were incubated with different concentrations of GrB/4D5/26 with or without 15 µM chloroquine. After 72 h, the relative number of viable cells was determined by crystal violet assay.

A significant observation was that incubation of cells with GrB/4D5/26 in the presence of chloroquine did not improve cytotoxicity toward these cells (FIG. 13). This finding demonstrated that the fusogenic peptide 26 efficiently releases GrB fusion proteins from intracellular vesicles, thereby allowing access to cytosolic GrB substrates and induction of apoptosis.

TABLE 12

Cytotoxic effects of Her2/neu-targeted therapeutic agents on $IC_{50}$ values in BT474 M1 cells and resistant variants.

| Agent | $IC_{50}$ (nM) with (Fold Resistance)* | | | | | |
|---|---|---|---|---|---|---|
| | BT474 M1 | BT474 M1 HR | BT474 M1 LR | BT474 M1 + EGF** | BT474 M1 + NRG-1*** | BT474 M1 + β-estradiol**** |
| Herceptin | 52.5 (1) | 10100.5 (192) | 74100.0 (1411) | 26305.0 (501) | 23033.0 (439) | 74.1 (1) |
| Lapatinib | 34.7 (1) | 32.4 (1) | 8225.0 (237) | 543.0 (16) | 547.1 (16) | 33.9 (1) |
| GrB/4D5/26 | 32.9 (1) | 26.8 (1) | 66.1 (2) | 21.7 (1) | 18.1 (1) | 31.3 (1) |

*Fold Resistance (F.R.) represents $IC_{50}$ of agent on BT474 M1 resistant variants/that on BT474 M1 parental cells.
Cells were pretreated with 20 ng/mL EGF, *50 ng/mL NRG-1, or ****10 ng/mL beta-estradiol for 72 h before drug treatment.

Mechanistic Studies of GrB/4D5/26 Cytotoxicity.

The inventors conducted a panel of experiments to assess the potential of GrB-based fusions to initiate the proteolytic cascade culminating in apoptosis of BT474 M1 parental, HR, and LR cells.

Annexin V/Propidium Iodide (PI) Staining.

The Annexin V/PI staining assay was used to quantitatively determine the percentage of cells undergoing apoptosis after exposure to GrB/4D5/26. Cells were seeded onto 6-well plates (5×10⁵ cells per well) and incubated with 100 nM GrB/4D5/26 at 37° C. for 24 or 48 h. Aliquots of cells were washed with phosphate-buffered saline and then incubated with Annexin V-FITC antibody. PI solution was added at the end of the incubation, and the cells were analyzed immediately by flow cytometry.

Figure 7A:
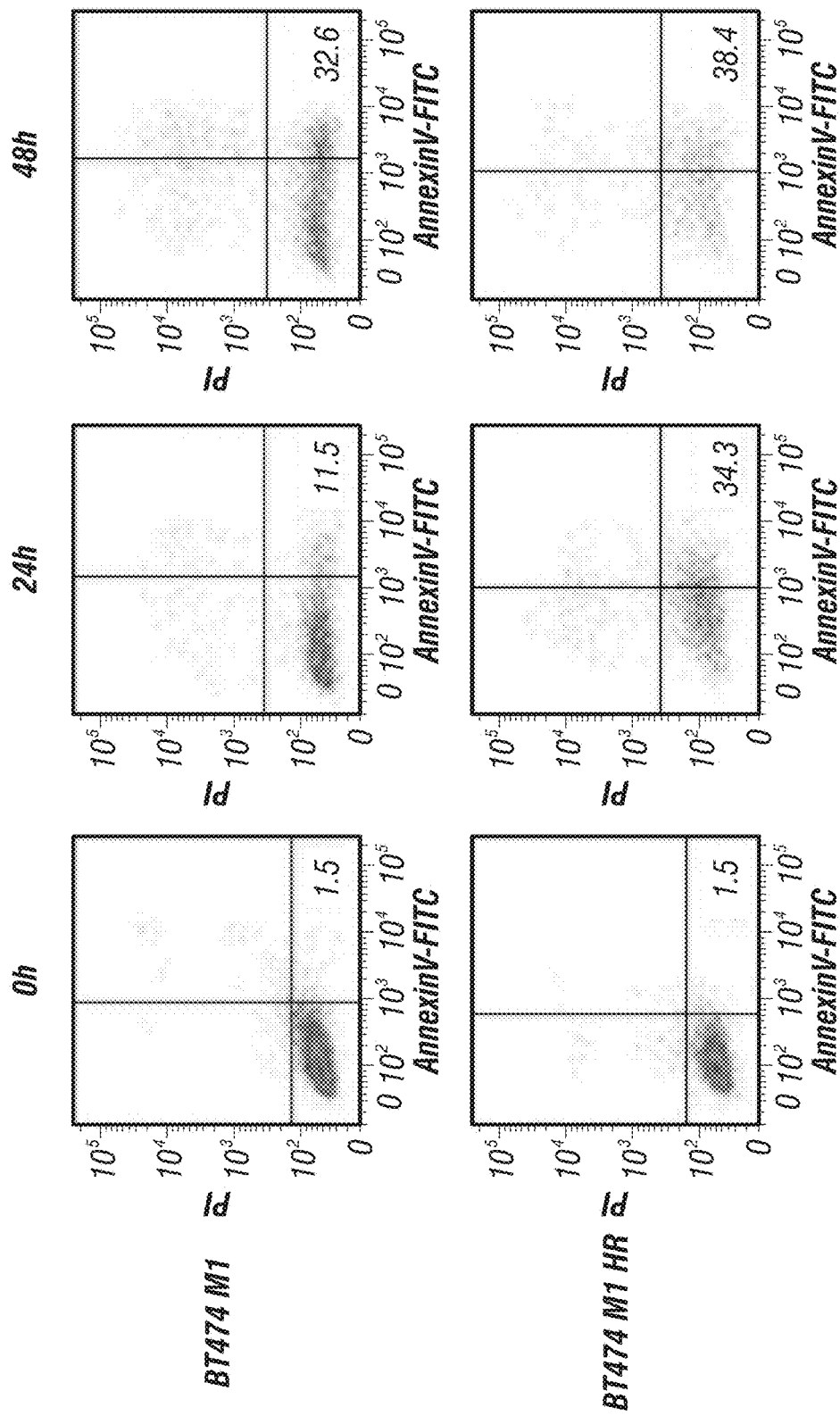
Figure 7A:
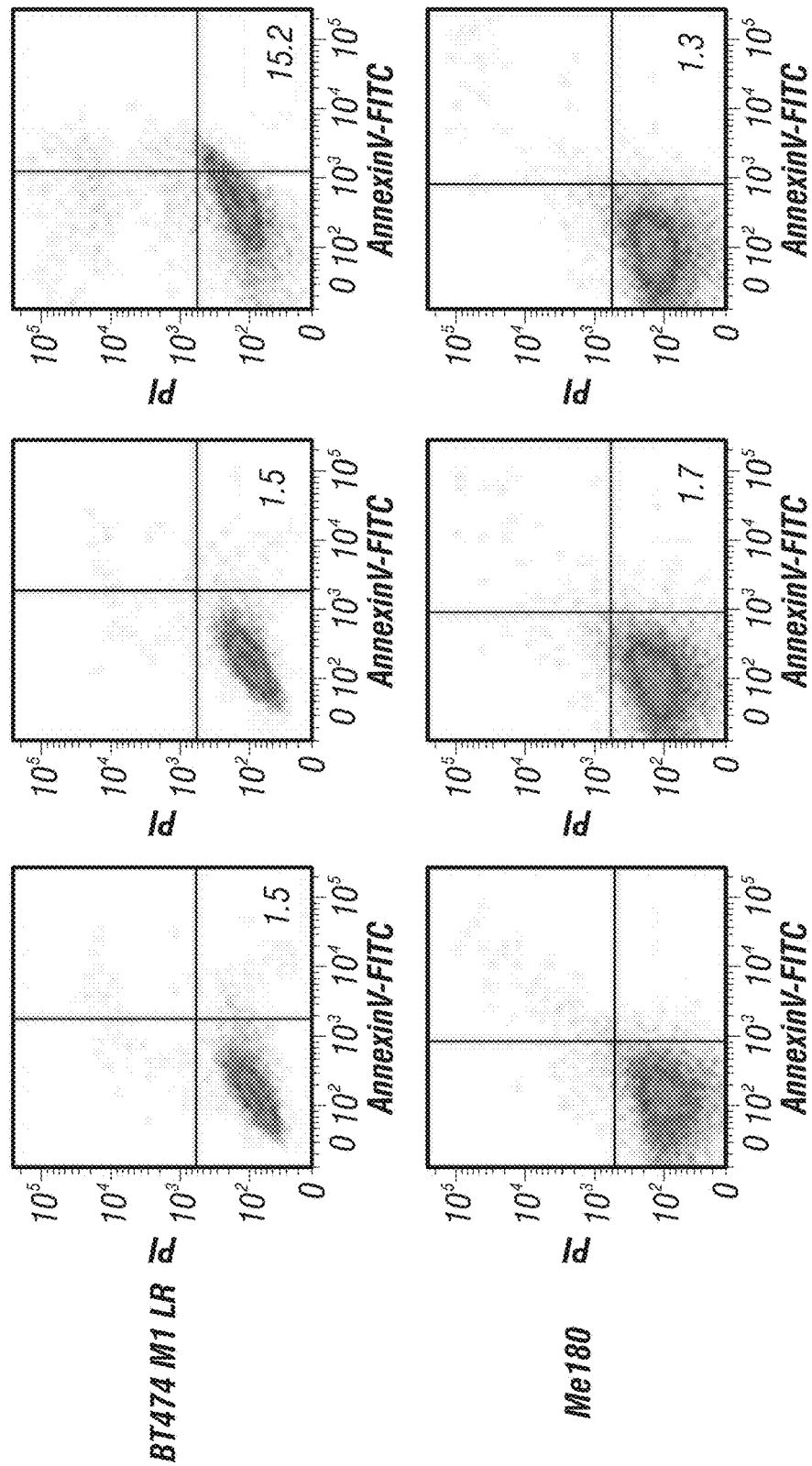
Figure 14:
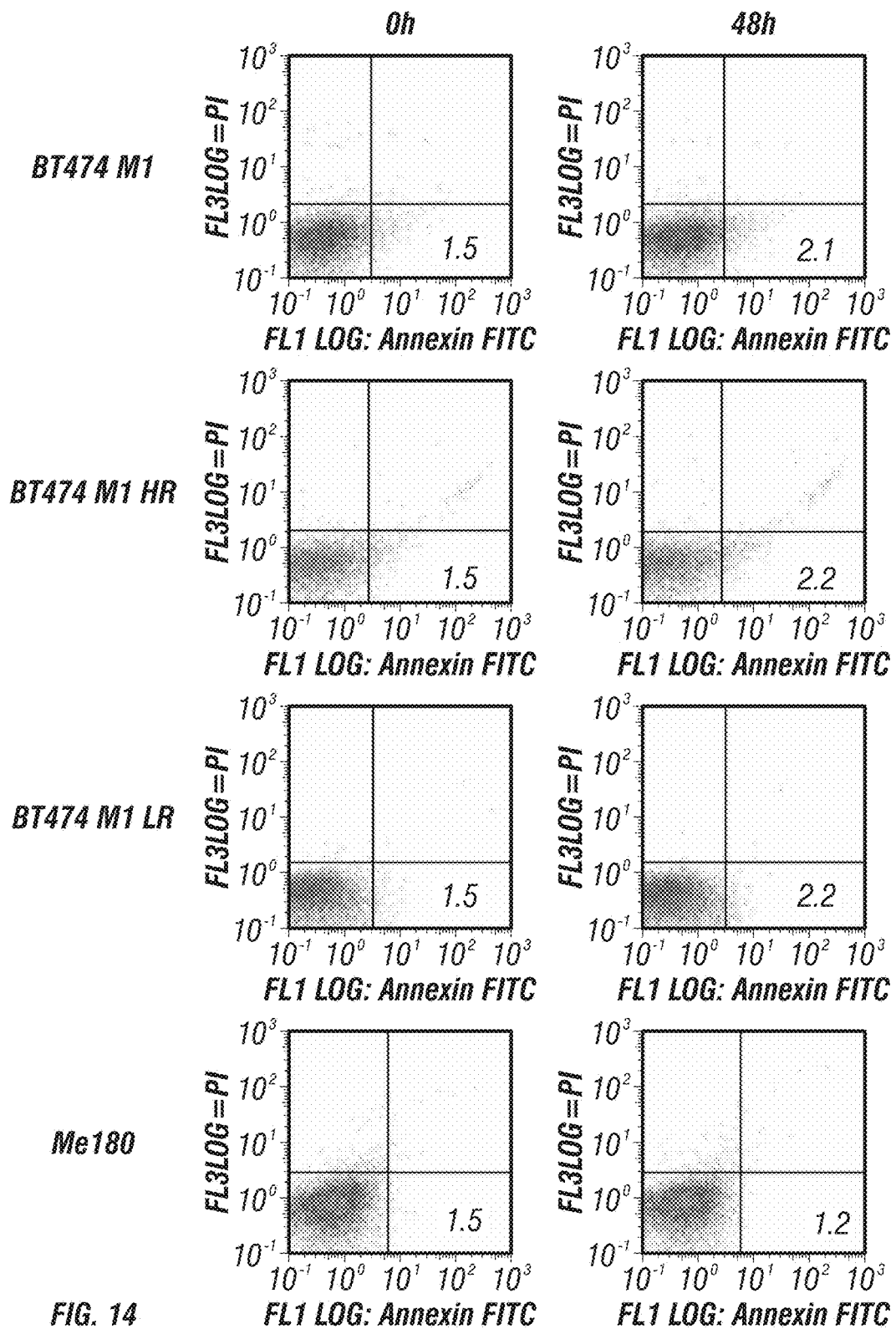
FIG. 14: Apoptotic effects of GrB/4D5 on Her2/neu positive and negative cells. To assess apoptosis, cells were seeded at $5 \times 10^5$ cells per 6-well plate, and then treated with 100 nM GrB/4D5 for 48 h. The development of apoptotic cell death was detected by Annexin V/PI staining assay.

GrB/4D5/26 induced apoptosis in BT474 M1 parental, HR, and LR cells, as indicated by the reduced viable population combined with greater populations of early apoptosis (FIG. 7A). No apoptosis was induced by 100 nM GrB/4D5 in any of these cells (FIG. 14). Her2/neu-negative Me180 cells were not affected by either construct.

Activation of Caspases.

Figure 7B:
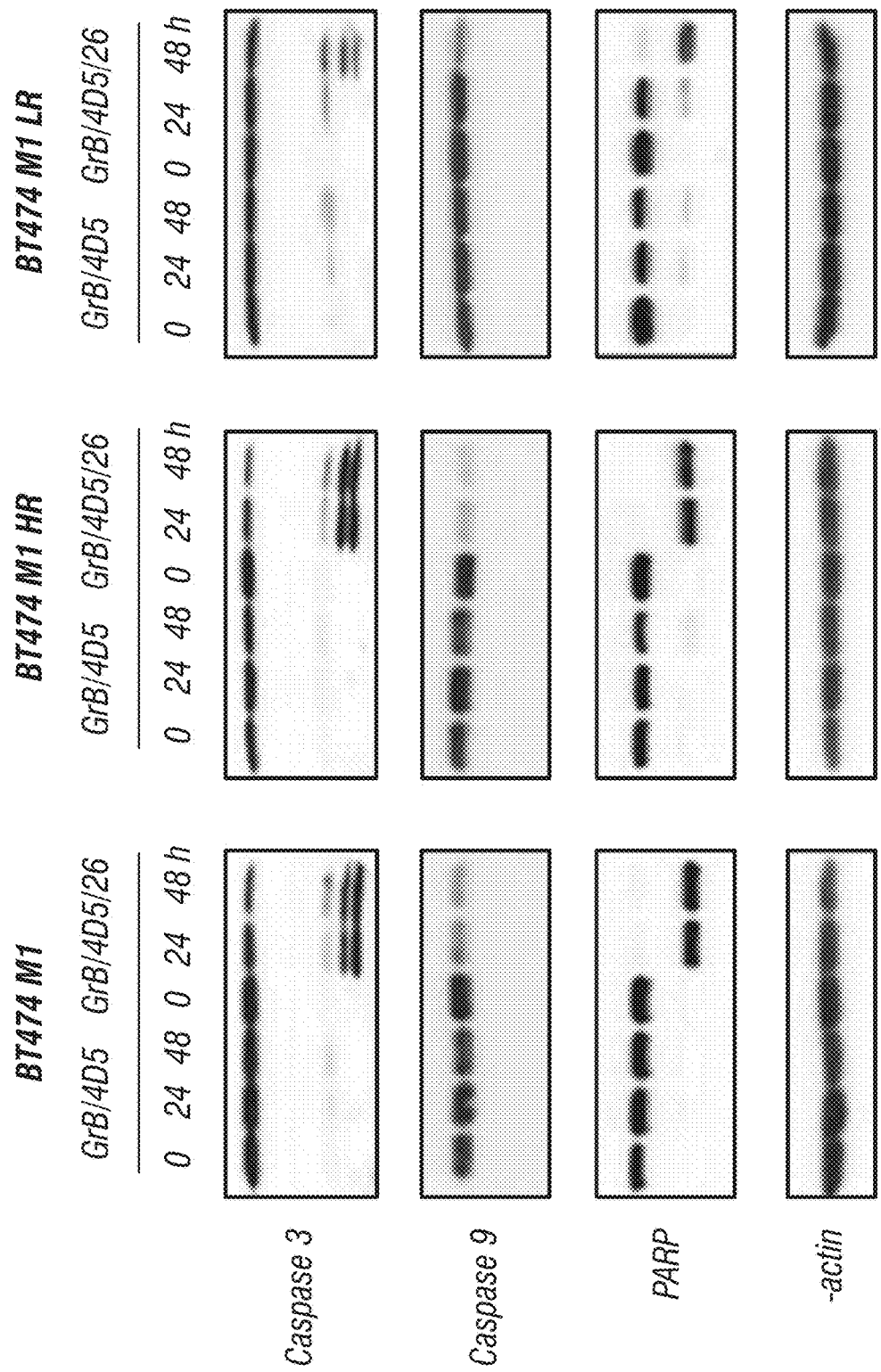

Western blot analysis was used to identify activation of caspases-3, and -9 as well as PARP cleavage. Treatment of BT474 M1 cells with GrB/4D5/26 resulted to the cleavage of caspase 3, caspase 9, and PARP in all cells, but no activation occurred when cells were treated with GrB/4D5 (FIG. 7B). Compared with BT474 M1 parental and HR cells, the activations of caspase-9, caspase-3, and PARP were delayed in LR cells, which coincided with the observed decreased cytotoxic effects.

The inventors further assessed the kinetics of PARP cleavage induced by GrB/4D5/26 on BT474 M1 parental, HR, and LR cells, and found that cleavage occurred after 2 h of drug exposure for parental and HR cells but at 24 h for LR cells (FIG. 7C). In addition, in the presence of the pan-caspase inhibitor zVAD-fmk, PARP cleavage of GrB/4D5/26 was partially inhibited in all cells. This finding is in agreement with a mechanism relying on GrB activity for caspase-3 cleavage followed by PARP cleavage.

Impact on Mitochondrial Pathways.

After treatment with GrB/4D5 or GrB/4D5/26, cells were collected and resuspended with 0.5 mL of 1× cytosol extraction buffer mix (BioVision, Milpitas, Calif.) and then homogenized in an ice-cold glass homogenizer. The homogenate was centrifuged, and the supernatant was collected and labeled as the cytosolic fraction. The pellet was resuspended in 0.1 mL of mitochondrial extraction buffer and saved as the mitochondrial fraction. Aliquots of each cytosolic and mitochondrial fraction were analyzed by western blotting with antibodies recognizing cytochrome c and Bax (Santa Cruz Biotechnology, Santa Cruz, Calif.). In addition, apoptosis was analyzed by western blot analysis using antibodies recognizing Bcl-2 and BID (Santa Cruz Biotechnology).

Figure 8B:
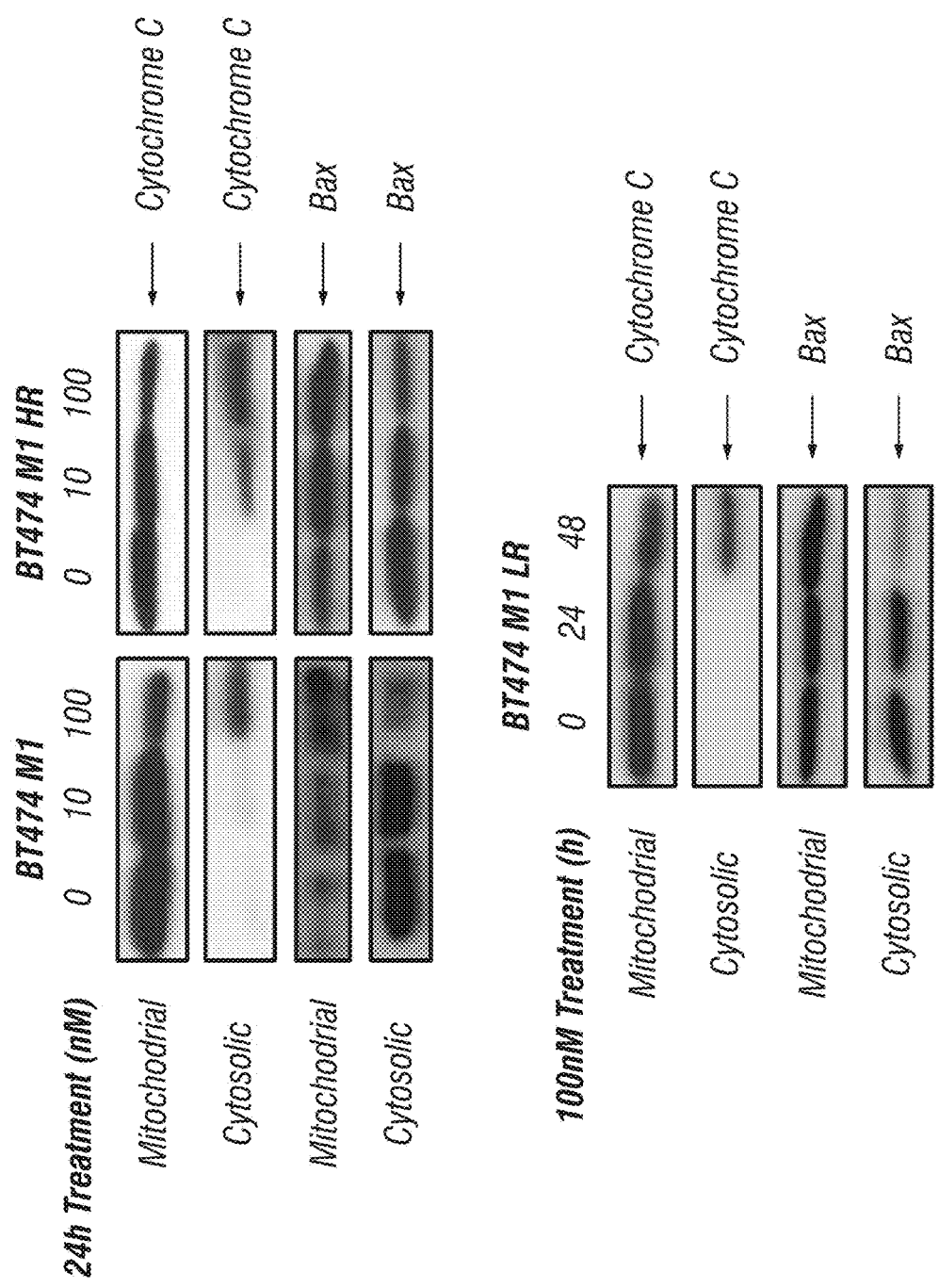

The inventors detected cell death induced by GrB/4D5/26 via several mitochondrial-related pathways. In BT474 M1 parental, HR, and LR cells, GrB/4D5/26 treatment activated BID and downregulated the anti-apoptotic Bcl-2 protein (FIG. 8A), and it triggered the release of cytochrome c from the mitochondria into the cytosol (FIG. 8B). Bax was normally present in both the cytosol and mitochondria of untreated cells. However, when the cells were treated with GrB/4D5/26, Bax was decreased in cytosol and increased in mitochondria (FIG. 8B). As previously described, treatment for 24 h with GrB/4D5/26 was shown to activate the mitochondrial pathway in both BT474 M1 parental and HR cells, but this activation was delayed in LR cells.

Effects of GrB Fusions on her- and ER-Associated Signaling Pathways.

After treatment, cell lysates were analyzed by western blotting with antibodies recognizing Her2/neu and phosphorylated (p)-mTOR (S2448) (Cell Signaling Technology, Danvers, Mass.) as well as p-Her2/neu (Tyr877), p-Her2/neu (Tyr 1221/1222), EGF receptor, p-EGF receptor (Thr845), Her3, p-Her3 (Tyr1328), IGF1 receptor, p-IGF1 receptor (Tyr 1165/1166), ER, PR, Akt, p-Akt, ERK, p-ERK (Thr 177/Thr 160), PTEN, PI-9, and β-actin (all from Santa Cruz Biotechonology). Immunoreactive proteins were visualized by enhanced chemiluminescence.

Figure 15:
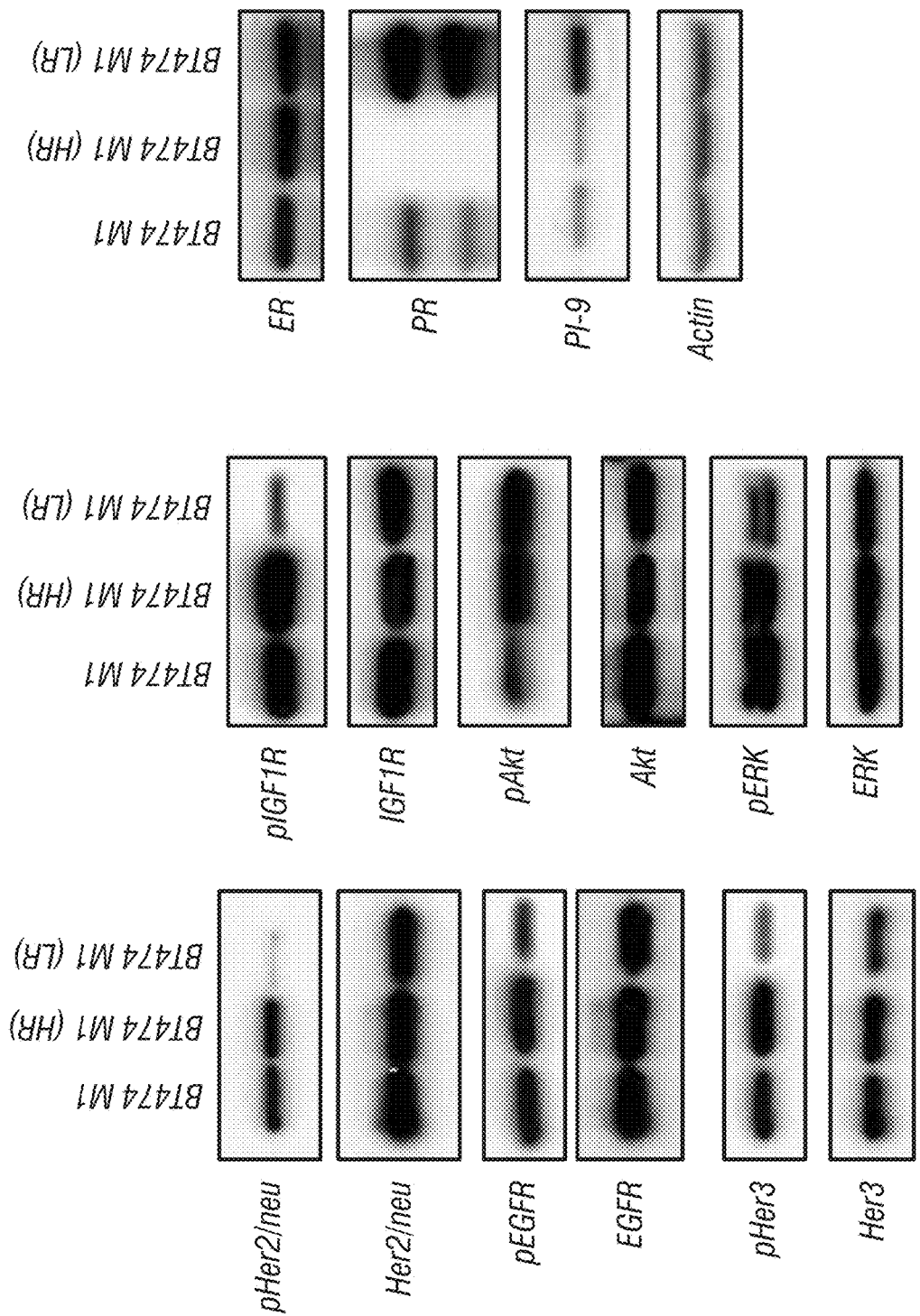
FIG. 15: Western blot characterization of BT474 M1 parental and its derived Herceptin- and Lapatinib-resistant cells. The characters included the expression and activation of Her- and ER-family members, the downstream ERK and Akt activity, and the endogenous GrB inhibitor PI-9 level in each cell line.

The inventors examined the mechanistic effects of the constructs on Her- and ER-related signaling events in BT474 M1 parental cells and the resistant variants. As shown in FIG. 15, cells resistant to Herceptin had enhanced Her family receptor activity but reduced levels of progesterone receptor (PR) and PI-9. In contrast, in LR cells there was total downregulation of Her family receptor activity but higher levels of ER, PR, and PI-9.

Figure 9:
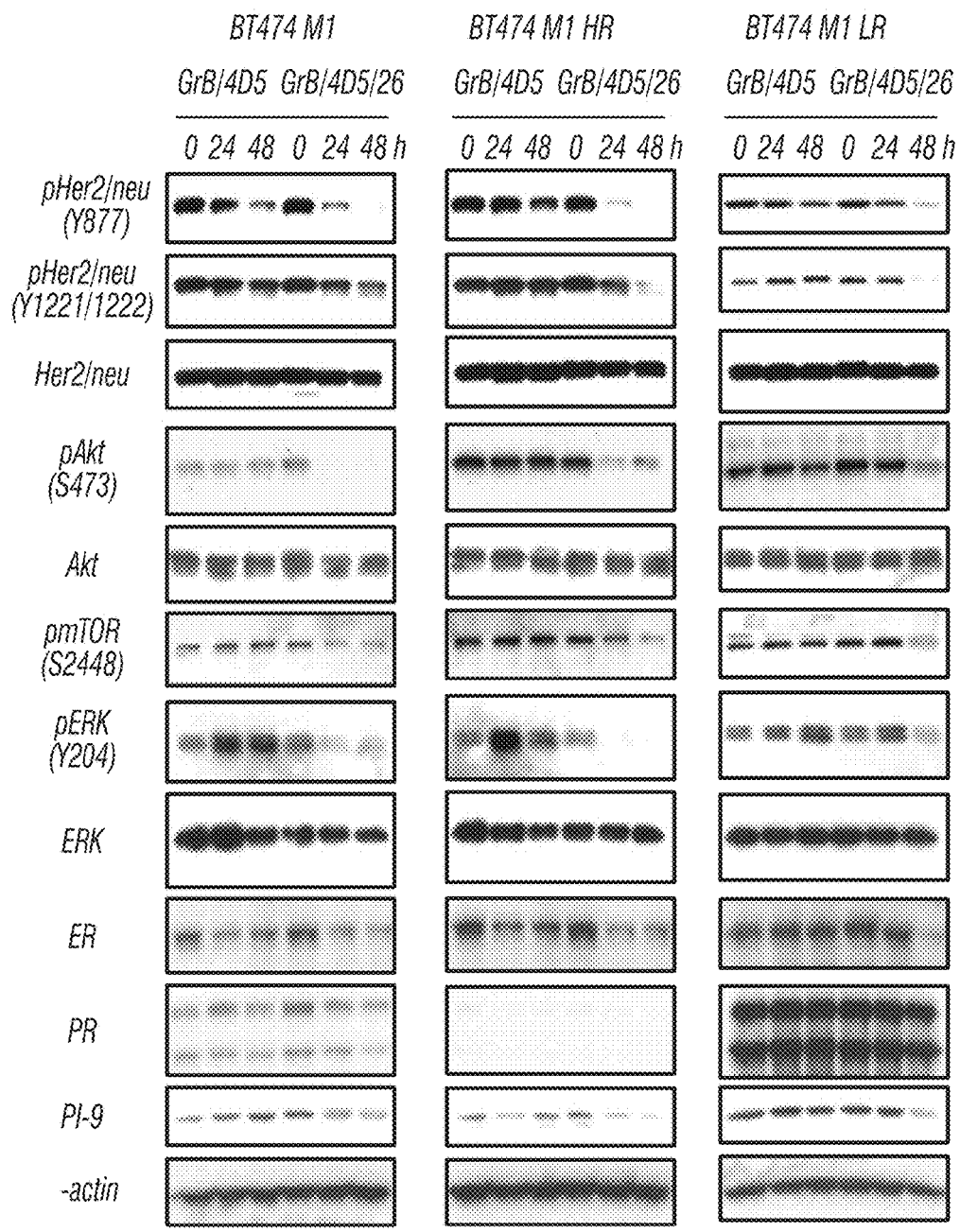
FIG. 9: Western blot analyses of the effects of GrB/4D5 and GrB/4D5/26 in BT474 M1 parental, HR, and LR cells on Her2/neu and ER signaling pathways. Cells were treated with 100 nM immunoGrB for 24 or 48 h, and total cell lysates were quantified and further evaluated by western blot analysis for pHer2/neu, pAkt, pmTOR, pERK, strogen receptor (ER), progesterone receptor m(PR), and PI-9 levels.
Figure 16:
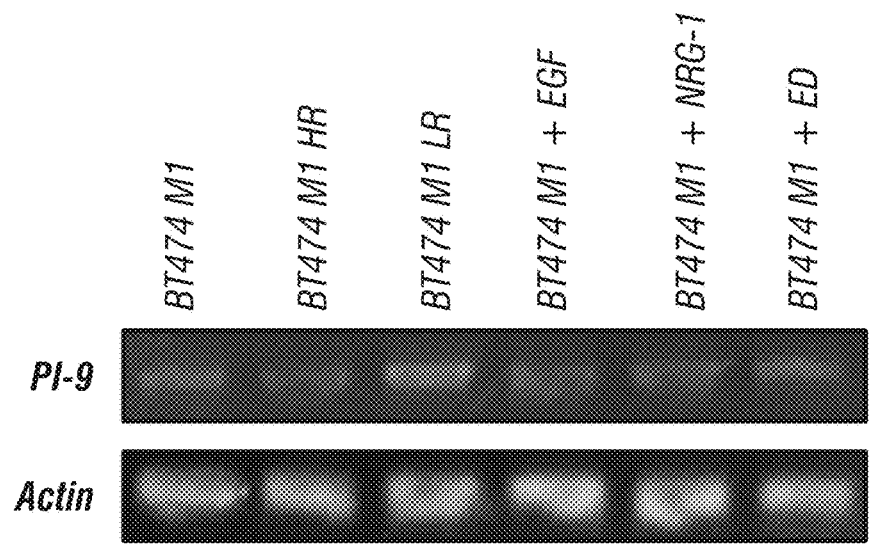
FIG. 16: mRNA level of PI-9 in BT474 M1 parental and resistant variants. Cells were harvested and RNA was extracted. The expression level of PI-9 and β-actin mRNA was detected by semi-quantitative reverse-transcription PCR.

Cells treated with GrB/4D5 or GrB/4D5/26 demonstrated the effects on these signaling pathways, corresponding to the cytotoxic results the inventors observed (FIG. 9). Treatment with GrB/4D5/26 markedly inhibited phosphorylation of Her2/neu and its downstream molecules Akt, mTOR and ERK, which are critical events in Her2/neu signaling cascade. In contrast, GrB/4D5 showed a comparatively reduced effect on these pathways. The inventors observed a reduced ER level among all cells. Evidence from other researchers has demonstrated that upregulation of the ER pathway in ER- and Her2/neu-positive cell lines with Lapatinib creates an escape/survival pathway (Wang et al., 2011; Liu et al., 2009), but GrB/4D5/26 appear to be able to inactivate all the signaling pathways in these cells. The inventors also observed the delaying signaling effects of GrB/4D5/26 on LR cells compared with parental or HR cells, which was in agreement with the apoptotic cell death results observed for the LR cells. Notably, there was an increased mRNA and protein level of PI-9 in this resistant line but not in the parental or HR cells (FIGS. 15 and 16). Taken together, these results suggest that activation of the ER pathway upregulates the expression of PI-9, which results in a slight inhibition of GrB/4D5/26 activity and a delay in apoptotic cell death compared to parental cells.

The inventor's investigation suggests that the GrB/4D5/26 fusion is more cytotoxic than GrB/4D5 construct to Her2/neu-positive cells, even those that have acquired resistance to the traditional Her2/neu therapeutic agents Herceptin and Lapatinib. The cytotoxicity results coincide with the observed effects on signal transduction and monitoring these pathways may be useful as a monitor of drug efficacy.

Effects of GrB/4D5/26 on the MDR-1 Expressing Cells.

Multidrug resistance (MDR) is a phenomenon that results from various reasons. The most-characterized cause of MDR is the overexpression of a 170-kDa membrane glycoprotein known as P-glycoprotein (Pgp). To verify the effects of GrB-based fusions on the Her2/neu positive cells with MDR-1 expression, the inventors generated the BT474 M1 MDR-1 cells by the transfection of plasmid pHaMDR1 to parental BT474 M1 cells. As Table 13 shown, compared with parental cells, BT474 M1 MDR-1 showed 209-fold resistance to Taxol, and 89-fold resistance to Vinblastin. However, the inventors could not observe the cross-resistance of MDR-1 cells to GrB/4D5 and GrB/4D5/26 constructs. Therefore, GrB-based fusion constructs demonstrate a wide range cytotoxicity to target cells even those with acquired resistance to chemotherapeutic agents.

TABLE 13

Cytotoxicity of Chemical agents and GrB-based fusions on MDR-1 expressing cells.

| | IC50 (nM) | | |
|---|---|---|---|
| | BT474 M1 | BT474 M1 MDR-1 | Fold Resistance* |
| Taxol | 5.2 | 1047.3 | 209 |
| Vinblastin | 1.3 | 105.1 | 89 |
| GrB/4D5 | 311.8 | 318.9 | 1 |
| GrB/4D5/26 | 34.1 | 35.5 | 1 |

*Fold Resistance (F.R.) represents $IC_{50}$ of agent on BT474 M1 MDR-1 cells/that on BT474 M1 parental cells.

Antitumor Activity of GrB/4D5/26 Fusions in Xenograft Models.

The inventors used BALB/c nude mice to evaluate the in vivo effect of GrB/4D5/26 against aggressive breast cancer after systemic administration. Each mouse received a weekly subcutaneous injection of 3 mg/kg estradiol cypionate (Jerome et al., 2006; Gully et al., 2010) starting 2 weeks prior to the injection of $1 \times 10^7$ BT474 M1 cells into the right flank. On the third day after cell inoculation, mice were injected intravenously (tail vein) either with saline or GrB/4D5/26 (44 mg/kg) five times per week for 2 weeks. Animals were monitored, and tumors were measured (calipers) for an additional 50 days. Compared with saline, GrB/4D5/26 greatly slowed tumor progression over 50 days of observation (FIG. 10A). There were no obvious toxic effects of GrB/4D5/26 on mice at this dose suggesting that the maximum tolerated dose at this schedule had not been reached.

Finally, the inventors determined the localization of GrB/4D5/26 after administration to mice bearing BT474 M1 tumors. Twenty-four hours after the final injection of saline or GrB/4D5/26, the mice were sacrificed and tumor samples were frozen immediately in preparation for section slides. The sample slides were incubated with either anti-GrB antibody (FITC-conjugated secondary antibody) or a terminal deoxynucleotidyl transferase-mediated nick end labeling (TUNEL) reaction mixture, as well as with an anti-mouse CD31 antibody (phycoerythrin-conjugated secondary antibody), and were further subjected to nuclear counterstaining with Hoechst 33342. Immunofluorescence observation was performed under a Zeiss Axioplan 2 imaging microscope (Carl Zeiss).

Figure 10B:
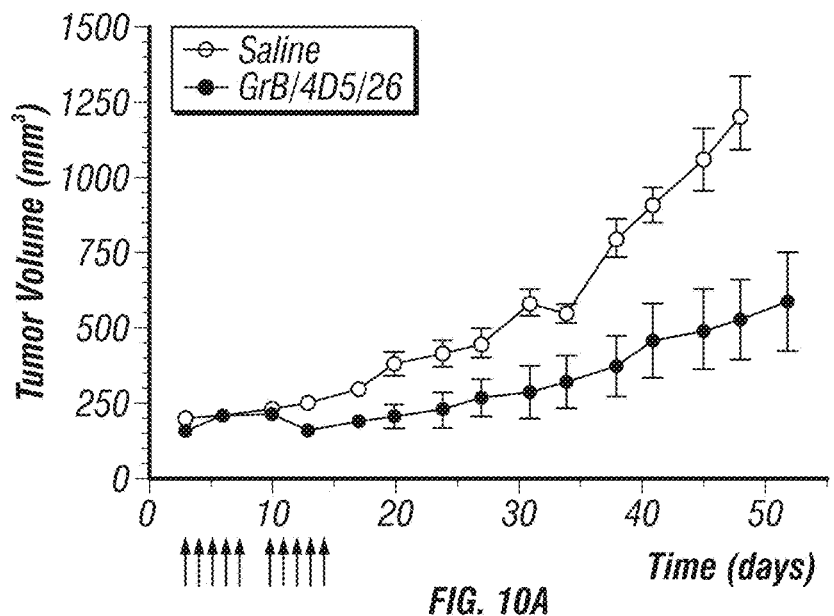
Figure 10B:
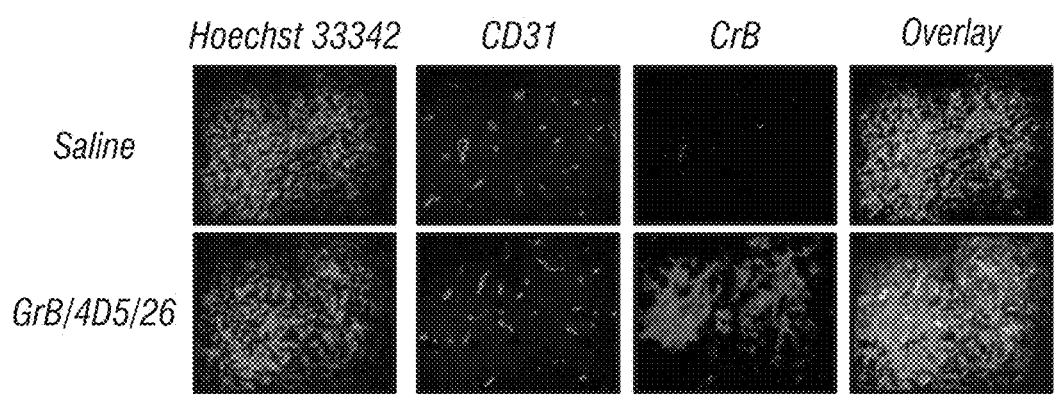
Figure 10C:
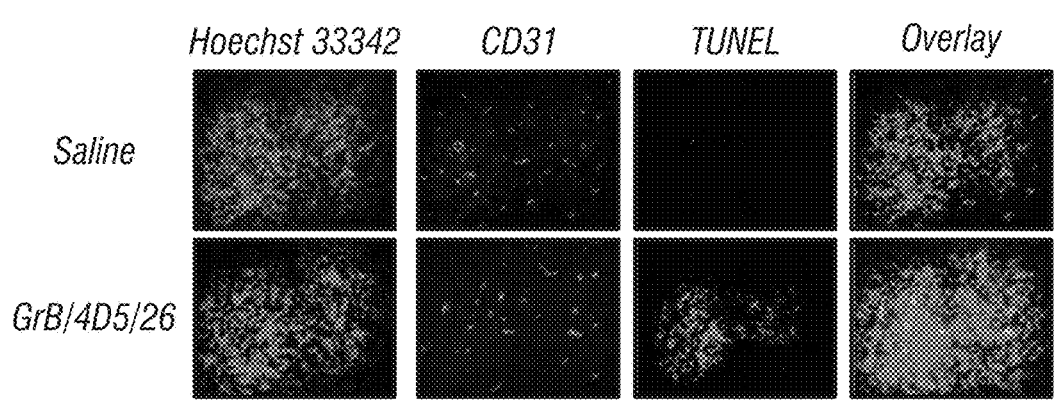

Immunofluorescence staining confirmed that GrB/4D5/26 localized quickly and specifically in tumor tissue (FIG. 10B). This observation further suggested that GrB/4D5/26 can effectively target tumor cells overexpressing Her2/neu in vivo and can demonstrate significant tumor growth-suppressive effects in the absence of observable toxicity. Staining of tumor tissue nuclei with TUNEL (FIG. 10C) clearly demonstrated that the tumor tissues displayed apoptotic nuclei in the GrB/4D5/26 treatment group. In addition, the intratumoral distribution of GrB/4D5/26 appeared to concentrate primarily in areas with extensive apoptotic response (compare Grb/4D5/26 distribution in FIG. 10B, with TUNEL staining in FIG. 10C).

In these studies, the inventors constructed novel human anti-Her2/neu immunotoxins containing human GrB as an apoptosis-inducing effector. GrB appears to be an ideal payload for targeted therapeutic applications in part because this serine protease exerts a multi-modal and well-known mechanism of cytotoxic action (Trapani and Sutton, 2003; Chowdhurty and Lieberman, 2008). Of interest, this study found that inhibitors of caspase activation had little impact on the overall cytotoxicity of the construct attesting to the presence of multiple, redundant, pro-apoptotic pathways activated by this molecule and suggesting that emergence of resistance to this class of agents may be difficult from a biological perspective.

In a nominal cytotoxic process, GrB penetrates directly into target cells through the action of perforin-mediated transmembrane pores. This process bypasses the lysosomal compartment allowing GrB accessibility directly to cytosolic substrates (Motyka et al., 2000). Internalization of GrB through antibody-mediated events provides tumor cell specificity but in the case of Her2/neu, internalization likely proceeds through the lysosomal compartment. For the inventor's optimal construct, the inventors included a 26-residue, fusogenic peptide. At neutral pH, this peptide has a random configuration, but under acidic lysosomal conditions, this peptide assumes an amphipathic helix thereby disrupting the lysosomal membrane allowing improved delivery of the fusion construct into the cytosol (Turk et al., 2002).

Dalken et al. (2006) described the construction and biological activity of Her2/neu targeted fusion construct GrB/FRP5. This agent was shown to be specifically cytotoxic to target cells with $IC_{50}$ values in the subnanomolar range but the cytotoxic activity was dependent on the addition of the lysomotropic agent chloroquine. In the absence of chloroquine, the cytotoxicity of the agent was reduced 10-300 fold thus suggesting that the construct may have been primarily sequestered into the lysozomal compartment and not available to activate apoptotic cascade mechanisms. The incorporation of the fusogenic, pH-sensitive peptide 26 in the inventor's construct appeared to circumvent the need for a lysomotropic agent to augment the activity of GrB fusion and it provided a greater concentration of target protein in the cell. The use of this peptide did not appear to impact the enzymatic activity of the GrB component nor did it influence the binding activity of the 4D5 to Her2/neu receptor. Finally, the presence of the 26 component did not appear to augment the nonspecific toxicity of the construct against antigen-negative cells in vitro nor did it increase the apparent toxicity of the construct during i.v. administration in the inventor's xenograft studies.

The antitumor efficacy studies demonstrated that GrB/4D5/26 in the BT474 M1 xenograft model was effective at a total dose of 44 mg/kg. This dose translates to a total dose of ~140 mg/m². Clinical dose levels of the T-DM1 conjugate are approximately 3.6 mg/kg (~280 mg/m²), which is approximately 2 fold higher than the inventor's extrapolated clinical doses for the GrB construct. The inventor's study demonstrated that there were no deaths or weight loss during the treatment schedule suggesting the safety and tolerability of this agent. Although the inventors did not observe complete regression of tumor xenografts, alternative schedules or higher doses need to be employed.

The Her2/neu-targeted therapeutic agents Herceptin and Lapatinib have significantly improved outcomes in cancer treatment, but their use is limited by resistance and tolerability issues (Garrett and Arteaga, 2011; Bedard et al., 2009). Evaluating the cytotoxicity of functionalized GrB fusions to HR or LR cells represents an important step. The inventor's results suggested that GrB/4D5/26 inhibits the proliferation and survival of resistant cells as a result of caspase-dependent and independent apoptotic effects. In addition, the inventor's investigation into cellular signaling indicated that GrB/4D5/26 could efficiently downregulate the phosphorylation of Her2/neu and ER family members, resulting in inhibition of both PI3K/Akt and Ras/ERK pathways.

The development of multidrug resistance mechanisms affecting groups of therapeutic agents has been shown to be a central problem resulting in reduced response in cancer treatment (Szakacs et al., 2006; Hilgeroth et al., 2012). The emergence of MDR phenotypes could also be a serious problem for the application of ADCs (Hurvitz and Kakkar, 2012; Murphy and Morris, 2012). Studies by Kovtun et al. (2010) reported that ADCs utilizing PEG-based hydrophilic linkers showed higher retention in MDR-1 expressing cells than similar conjugates made with the nonpolar linker SMCC which is found in T-DM1. Therefore, the emergence of MDR may provide cross-resistance to T-DM1, due to the efflux of free drug upon intracellular release from the antibody. In contrast, the current studies demonstrate that expression of MDR does not provide cross-resistance to GrB-based fusion constructs and this appears to be a significant advantage over the conventional ADC approach.

The only intracellular inhibitor of human GrB is the nucleocytoplasmic serpin, PI-9. PI-9 has been found to be endogenously expressed in lymphocytes, dendritic cells and mast cells, for self-protection against GrB-mediated apoptosis (Trapani and Sutton, 2003; Chowdhury and Lieberman, 2008). This may suggest that the endogenous PI-9 level in cancer cells could inhibit the GrB activity of the inventor's target molecules. However, the inventor's studies did not show any relationship between PI-9 levels and cell sensitivity to GrB/4D5/26 in Her2/neu positive cells.

The inventors examined GrB sensitivity against Lapatinib-resistant cells and found these cells showed a slight (2-fold) increase in the GrB/4D5/26 $IC_{50}$. This coincided with an upregulation of PI-9 leading to a delay in apoptosis. This upregulation may be the indirect result of ER pathway changes induced by Lapatinib resistance. Therefore, in the cell lines that are both ER- and Her2-positive, for which upregulation of the ER pathway may occur as an escape pathway, the endogenous GrB inhibitor PI-9 could be upregulated to inhibit GrB activity.

In conclusion, the foregoing studies demonstrate that a novel Her2/neu targeted functionalized GrB fusion constructs employing the pH-sensitive fusogenic peptide 26 as an endosomolytic domain efficiently promotes the release of GrB into the cytoplasm, resulting in apoptotic cell death in Her2/neu-positive cancer cells. This fusogenic peptide could be useful for studying GrB-induced apoptosis without the requirement of perforin or chloroquine. In addition, the studies demonstrate that tumor cells highly resistant to either Lapatinib or trastuzumab (Herceptin®) and the cells with MDR-1 expression resistant to chemotherapeutic agents were not cross-resistant to the GrB-based fusion protein. Although the induction of PI-9 expression in LR cells delayed the apoptotic cytotoxicity of GrB/4D5/26, this agent had an $IC_{50}$ value that was only 2-fold higher than parental cells, despite the fact that resistant cells were more than 200-fold resistant to Lapatinib.

Example 12—Construction of Cleavable Carboxyl Terminal GrB Fusions

GrB fusion constructs were constructed comprising a targeting polypeptide positioned at the N-terminus relative to the GrB coding sequence. The resulting fusion proteins are engineered to include a protease cleavage site that, after protease cleavage releases an active GrB enzyme (i.e., have a free isoleucine at the amino terminus).

Initial constructs tested comprised a targeting moiety (e.g., an antibody)+caspase cleavable peptide+Granzyme B ("the insert"). A linker, such as the $G_4S$ linker or a 218 linker, may also be incorporated between the targeting moiety and the cleavable peptide. One caspase cleavable peptide sequence of particular interest is the YVDEVD↓ (SEQ ID NO: 25; which can be followed by the GrB amino acid sequence), where the "↓" indicates the cleavage site. In some aspects, the caspase-3 cleavable peptide may be substituted with a peptide cleavable by a different protease, such as another caspase or furin.

Figure 17:
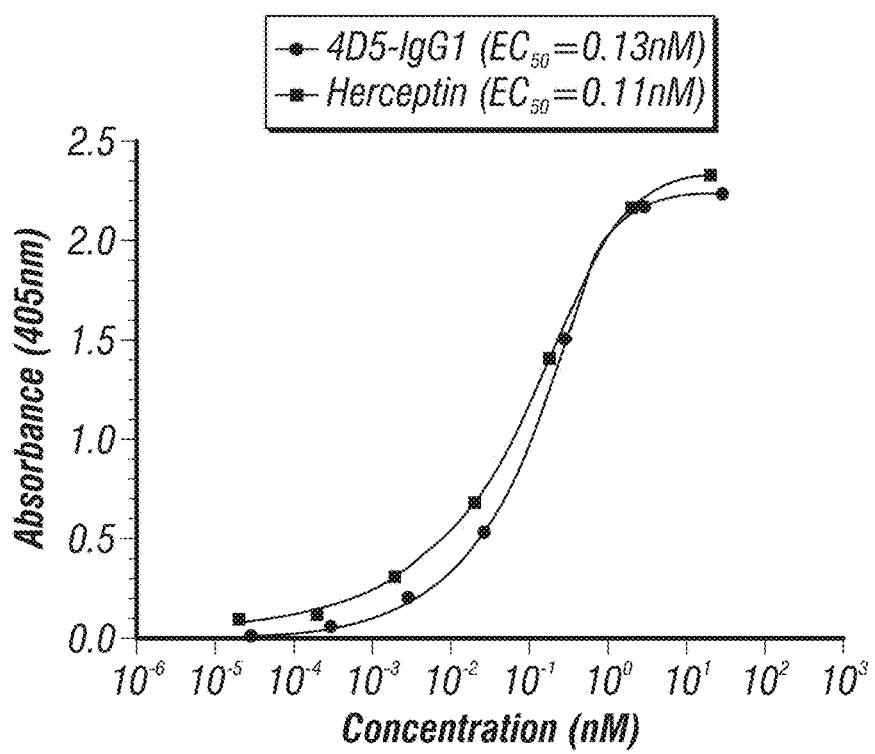
FIG. 17: Graph show the results of ELISA studies of the affinity of 4D5-IgG1 vs. Herceptin® on the Her2 extra cellular domain (ECD).

For the initial test constructs the anti-Her2/neu scFv 4D5 sequence was grafted onto a human IgG1 framework to generate the "4D5-IgG1" base construct. This grafted antibody was subject to testing of affinity to the Her2 ECD as compared to Herceptin®. These studies, shown in FIG. 17, confirm that the two antibodies display similar target affinity. Using the 4D5-IgG1 base, several GrB fusion proteins were generated and tested for cytotoxic activity against appropriate cell lines. The constructs produced were as follows:

4D5-Ac—

Figure 18:
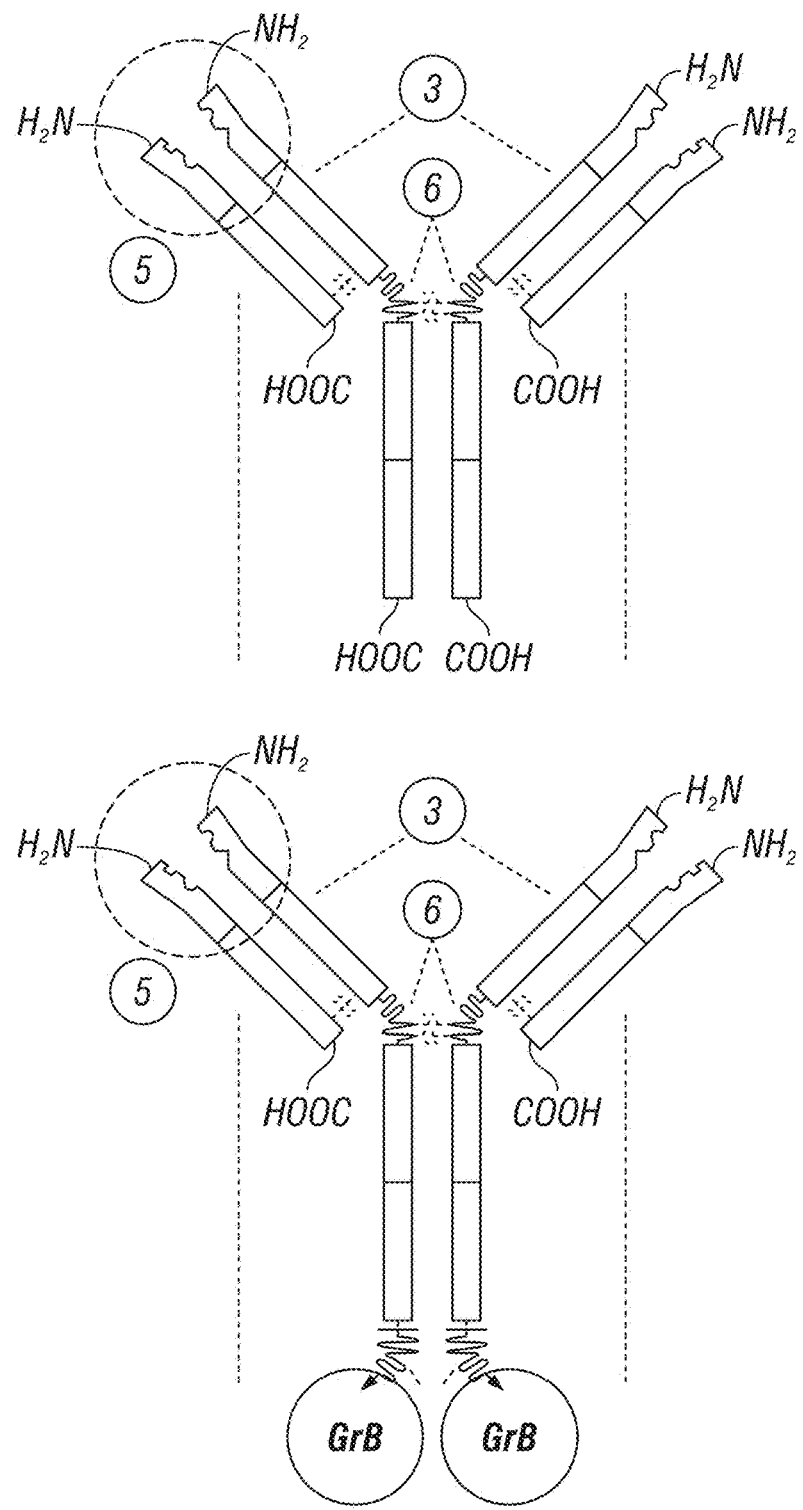
FIG. 18: A schematic showing various GrB antibody fusion constructs. Upper left panel shows a basic IgG structure. Upper right panel shows an IgG structure comprising a GrB fused to the light chain via a cleavable linker. Lower left panel shows an IgG structure comprising a GrB fused to the heavy chain via a cleavable linker. Lower right panel shows GrB fused to a heavy chain (Fc) comprising single-chain antibodies fused to its C-terminus.
Figure 18:
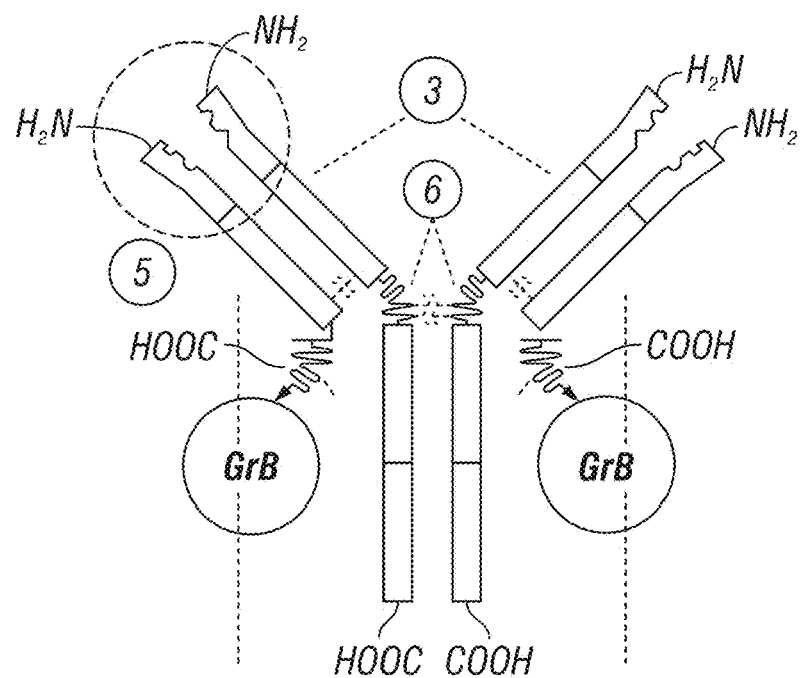
Figure 18:
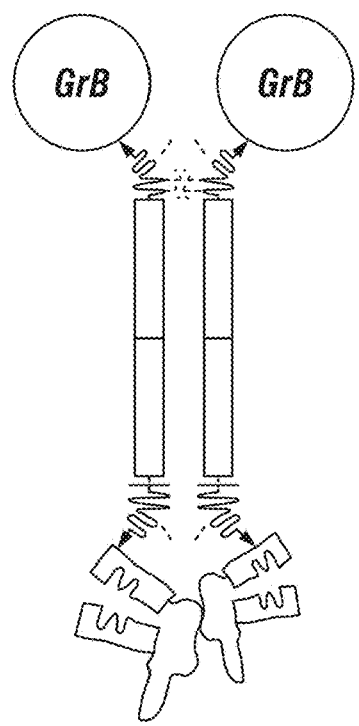

The 4D5-IgG1 heavy chain was fused to the N-terminus of GrB, such that the 4D5 heavy chain and GrB were separated by the caspase cleavable linker detailed above. In this case the GrB coding sequence comprises the N51S and C210A point mutations and included the INF7 translocation peptide at the C-terminus. Thus, from N- to C-terminus the heavy chain of the construct comprises 4D5IgG1 heavy chain—caspase cleavable linker—GrB—INF7 (see, e.g., FIG. 18, lower left panel).

4D5-AfNI—

The 4D5-IgG1 heavy chain was fused to the N-terminus of GrB, such that the 4D5 heavy chain and GrB were separated by the furin cleavable linker. The GrB coding sequence comprises the N51S and C210A point mutations. Thus, from N- to C-terminus the heavy chain of the construct comprises 4D5IgG1 heavy chain—furin cleavable linker—GrB (see, e.g., FIG. 18, lower left panel).

4D5-BfNI—

The 4D5-IgG1 light chain was fused to the N-terminus of GrB, such that the 4D5 light chain and GrB were separated by a furin cleavable linker. The GrB coding sequence comprises the N51S and C210A point mutations. Thus, from N- to C-terminus the light chain of the construct comprises 4D5IgG1 light chain—furin cleavable linker—GrB (see, e.g., FIG. 18, upper right panel).

4D5-AeafNI—

The 4D5-IgG1 heavy chain was fused to the N-terminus of GrB, such that the 4D5 heavy chain and GrB were separated by the caspase cleavable linker detailed above. In this case the GrB coding sequence comprises the N51S and C210A point mutations in addition to K27E and R28A. Thus, from N- to C-terminus the heavy chain of the construct comprises 4D5IgG1 heavy chain—caspase cleavable linker—GrB (see, e.g., FIG. 18, lower left panel).

IgG-Ac—

A murine anti-Her2 IgG1 heavy chain was fused to the N-terminus of GrB, such that the 4D5 heavy chain and GrB were separated by the caspase cleavable linker detailed above. In this case the GrB coding sequence comprises the N51S and C210A point mutations and included the INF7 translocation peptide at the C-terminus. Thus, from N- to C-terminus the heavy chain of the construct comprises a murine IgG1 heavy chain—caspase cleavable linker—GrB—INF7 (see, e.g., FIG. 18, lower left panel).

The constructs above were expressed in mammalian cells from a bicistronic expression vector arranged such that the heavy and light chain antibody polypeptides (or fusions thereof) were secreted. Assembled antibody fusion constructs were purified from the cell media. These constructs were then tested for cytotoxic activity relative to Her2-expressing SKBR3 cells or control MCF-7 cells (that do not express Her2). The results of these studies (shown below in Table 14) demonstrate that the GrB fusion antibodies all showed robust cytotoxic activity with at least 4× lower $IC_{50}$ as compared to Herceptin®.

TABLE 14

| Cytotoxicity of GrB/IgG constructs | | | | | | |
|---|---|---|---|---|---|---|
| Cell line | 4D5-Ac | 4D5-AfNI | 4D5-BfNI | 4D5-AeafNI | IgG-Ac | Herceptin ® |
| | | | $IC_{50}$ (nm) | | | |
| SKBR3 | 68 | 98 | 108 | 73 | 152 | 454 |
| MCF-7 | >200 | >200 | >200 | >200 | >200 | >1000 |

Additional studies were undertaken with GrB fusions to HMEL scFv. For these studies the cytotoxicity of constructs "HCB" (HMEL scFv-$G_4S$-YVDEVD (SEQ ID NO: 25)-GrB) was compared to control constructs "WH" (GrB-$G_4S$-

Figure 19:
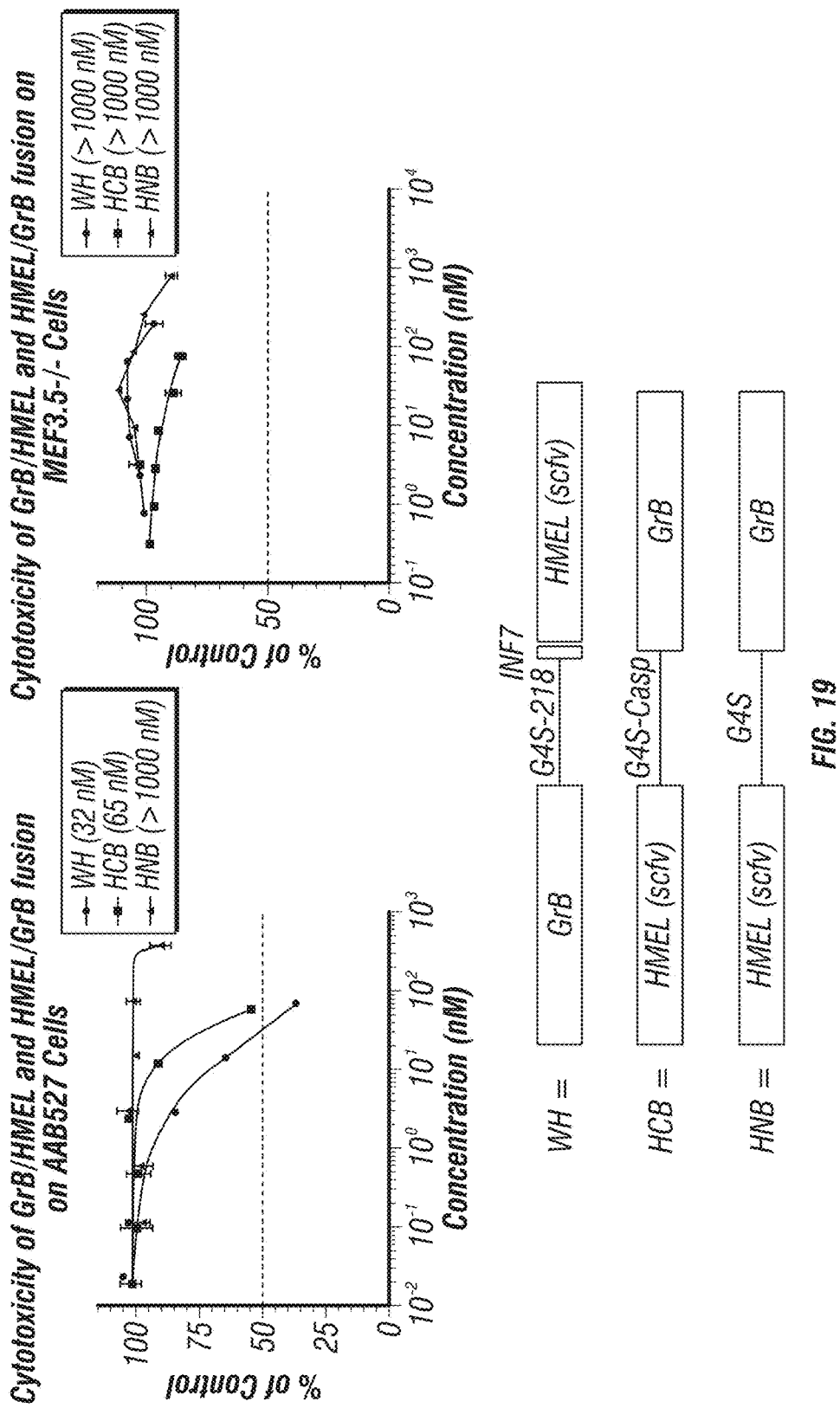
FIG. 19: The results of studies to measure the cytotoxicity of GrB constructs fused at the N-terminus versus the C-terminus with and without a proteinase cleavage site to free active GrB. Lower panel shows a schematic of constructs "HCB" (HMEL scFv-$G_4$S-YVDEVD (SEQ ID NO: 25)-GrB); "WH" (GrB-$G_4$S-INF7-HMEL scFv); and "HNB" (HMEL scFv-$G_4$S-GrB). Right panel, graph shows cytotoxicity of the constructs on MEF3.5−/− cells, which lack the HMEL scFv target receptor. Left panel, graph shows cytotoxicity of the constructs on AAB527 cells which have the HMEL scFv target receptor.
Figure 20:
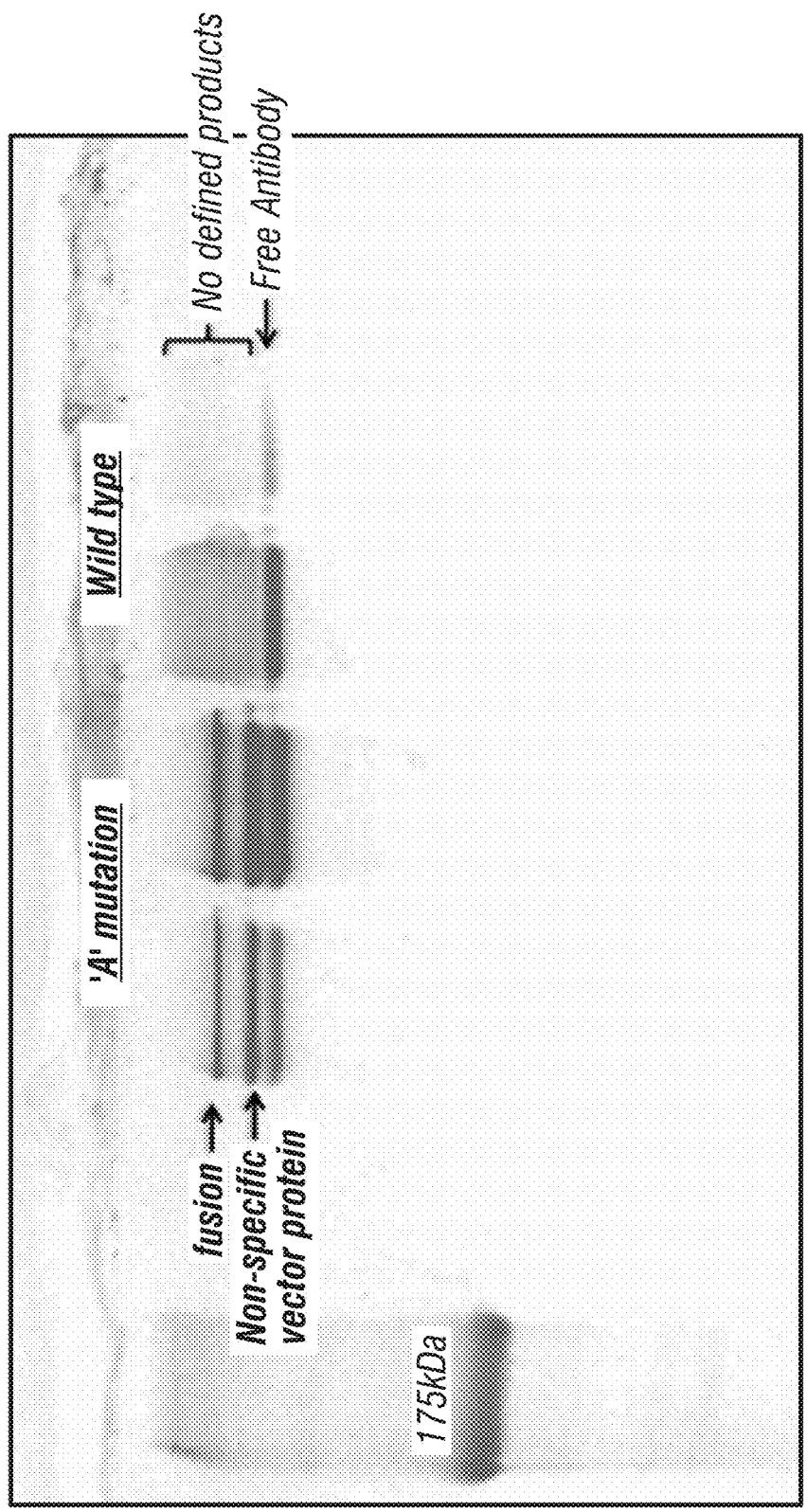
FIG. 20: A reproduction of an SDS-PAGE gel used to separate antibody fusions with wt GrB (right lanes) or GrB comprising the 'A' mutation (C210A). Results show that, in the case of antibody fusion with wt GrB, no defined band corresponding to the fusion protein was present. In contrast, the GrB 'A' mutant produced a significant amount of intact fusion protein as evidenced by the defined band apparent in the gel. Migration positions for free antibody, fusion protein and a non-specific vector protein are indicated.

INF7-HMEL scFv) and "HNB" (HMEL scFv-G$_4$S-GrB) were compared on AAB527 versus MEF3.5−/− cells (see FIG. 19, lower panel for construct schematics). The results of these studies shown in FIG. 19 demonstrate that, as expected, none of the constructs had significant activity relative to cells lacking the target receptor (right panel graph). In contrast only the WH and HCB constructs had significant activity relative to the AAB527 cells, showing the specific cleavage of the GrB into an active form was required for cytotoxic activity. Further studies will be undertaken to test constructs that comprise both a heavy chain and light chain GrB fusion.

Example 13—GrB Fusion Constructs Comprising scFv Regions Fused to Fc

Further GrB fusion constructs were designed and constructed that included scFv regions as well as antibody Fc domains. For these constructs GrB may be fused to be positioned N-terminal relative to the antibody sequences or at the c-terminus (via a cleavable linker as detailed above). Thus constructs can comprise the general structure GrB-Fc-scFv (see, e.g., FIG. 18, lower right panel) or scFv-Fc-cleavable linker-GrB.

As an initial test of this arrangement a construct was produced comprising GrB-Fc-IT4 (scFv). Specifically, the IT4 scFv targets the product of the tumor necrosis factor receptor superfamily, member 12A (TNFRSF12A) gene and was previously described in Zhou et al., 2011, which is incorporated herein by reference. The sequence of the fusion protein produced by the construct is provided as SEQ ID NO: 45. The constructs was expressed and purified as detailed supra and tested for activity against a panel of cells lines (using GrB alone a control). Results shown below in Table 15 demonstrate that the constructs were highly active with IC$_{50}$ values measure as low as 3.

TABLE 15

Cytotoxicity of GrB-Fc-IT4 constructs

| | IC50 (nM) | |
| --- | --- | --- |
| Cell lines | GrB-Fc-IT4 | GrB |
| A549 | 19 | 602 |
| AsPc-1 | 17 | 1297 |
| Capan-2 | 21 | >3200 |
| Capan-1 | 37 | 2344 |
| L3.6p1 | 35 | 1215 |
| H358 | 121 | >3200 |
| H520 | 62 | 259 |
| H1437 | 14 | >3200 |
| H1975 | >114 | >3200 |
| H2073 | >114 | >3200 |
| H3255 | 27 | 2359 |
| HCC827 | 114 | 1406 |
| HCC2279 | 19 | 526 |
| MDA-MB-435 | 12 | 445 |
| WM35P2N1 | 144 | 1543 |
| WM35 | 3 | >1923 |
| SB2 | 17 | >1923 |
| A375 | 73 | >1923 |
| SK-MEL-28 | >284 | >1923 |
| MCF-7 | 35 | >1923 |
| MDA-MB-231 | 17 | >1931 |
| MDA-MD-231-Luc | 3 | 3554 |
| HT-29 | 118 | >3200 |
| MEF 3.5 −/− | >114 | >3200 |

Example 14—Studies with Additional GrB-VEGF Fusion Constructs

Additional studies were undertaken to study the serum stability and cytotoxicity of various GrB mutants fused to a VEGF targeting moiety. The constructs tested were as follows: GrB/VEGF$_{121}$; EA-GrB/VEGF$_{121}$ (GrB mutant with the K27E, R28A point mutations); LA-GrB/VEGF$_{121}$ (GrB mutant with the K27L, R28A point mutations); EAPVPN-GrB/VEGF$_{121}$ ($^{82}$PKN$^{84}$ loop of wt GrB was mutated to PVPN and comprising the K27E, R28A point mutations); PVPN-GrB/VEGF$_{121}$ ($^{82}$PKN$^{84}$ loop of wt GrB was mutated to PVPN); LP-GrB/VEGF$_{121}$ (addition of His-tag, thrombin cleavage site and Caspase-3 cleavage site (DEVD) immediately upstream of the GrB N-terminus). These constructs were tested for enzymatic activity following incubation in serum (FBS) for 4 hours or incubation in PBS for 4 hours. The results of these studies are shown in Table 16 below. These studies showed that both the "EA" and "LA" mutations were able to remain significantly more active than control constructs following serum incubation.

The same constructs were tested for cytotoxic activity following incubation for 4 hours in serum (FBS) or in PBS. The results of these studies are shown in Table 17. These data demonstrate that, even after serum incubation, the "EA" and "LA" mutant targeting constructs remain highly active and specific against target cells. Crucially, however, the LP-GrB/VEGF$_{121}$ construct also remained highly active even after exposure to serum. It is hypothesized that the construct is protected by virtue of the fact that it is inactive until cellular uptake upon, which caspase cleavage activated GrB enzymatic activity.

TABLE 16

Resistance of GrB mutants to inactivation by serum

| | Enzymatic Activity remaining (%) | |
| --- | --- | --- |
| Construct | PBS (4 h) | FBS (4 h) |
| GrB/VEGF$_{121}$ | 82 | 36 |
| EA-GrB/VEGF$_{121}$ | 79 | 76 |
| LA-GrB/VEGF$_{121}$ | 100 | 51 |
| EAPVPN-GrB/VEGF$_{121}$ | ND | ND |
| PVPN-GrB/VEGF$_{121}$ | 100 | 34 |
| LP-GrB/VEGF$_{121}$ | Inactive | Inactive |

TABLE 17

Cytotoxicity of GrB mutants with or without pre-incubation in serum

| | IC$_{50}$ (nM) on PEA/VEGFR-2 cells | | IC$_{50}$ (nM) on PEA/VEGFR-1 cells | |
| --- | --- | --- | --- | --- |
| Construct | PBS (4 h) | FBS (4 h) | PBS (4 h) | FBS (4 h) |
| GrB/VEGF$_{121}$ | 4 | >100 | >100 | >100 |
| EA-GrB/VEGF$_{121}$ | 8 | 39 | >100 | >100 |
| LA-GrB/VEGF$_{121}$ | 8 | 63 | >100 | >100 |
| EAPVPN-GrB/VEGF$_{121}$ | 5 | Not tested | >100 | Not tested |
| PVPN-GrB/VEGF$_{121}$ | 8 | Not tested | >100 | Not tested |
| LP-GrB/VEGF$_{121}$ | 2 | 67 | >100 | >100 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,680,338
U.S. Pat. No. 5,141,648
U.S. Pat. No. 5,563,250
U.S. Pat. No. 5,856,456
U.S. Pat. No. 5,880,270
U.S. Pat. No. 6,232,287
U.S. Pat. No. 6,528,481
U.S. Pat. No. 7,452,964
U.S. Pat. No. 7,671,010
U.S. Pat. No. 7,781,565
U.S. Pat. No. 8,450,278
U.S. Pat. No. 8,507,445
U.S. Patent Appln. 2004005647
U.S. Patent Publn. 20050106660
U.S. Patent Appln. 20060234299
U.S. Patent Appln. 20060223114
U.S. Patent Publn. 20060058510
U.S. Patent Publn. 20060088908
U.S. Patent Publn. 20090253899
U.S. Patent Publn. 20100285564
U.S. Patent Publn. 20100317547
WO 97/19179
PCT Publication No. WO 1997/19179
PCT Publication No. WO2006/056464
Arai et al., 2004
Ausubel, 1996
Ausubel et al., 1998
Barclay et al. (eds.), The Leucocyte Antigen Facts Book, 1993, Academic Press.
Becker et al., *J. Neuroimmunol.*, 77:27-38, 1997.
Bedard et al., Beyond trastuzumab: overcoming resistance to targeted HER-2 therapy in breast cancer, *Curr. Cancer Drug Targets*, 9:148-162, 2009.
Bongartz et al., Improved biological activity of antisense oligonucleotides conjugated to a fusogenic peptide, *Nucleic Acids Res.*, 22:4681-4688, 1994.
Burkly et al.: TWEAKing tissue remodeling by a multifunctional cytokine: role of TWEAK/Fn14 pathway in health and disease. *Cytokine* 40:1-16 (2007).
Cao et al., Construction and characterization of novel, recombinant immunotoxins targeting the Her2/neu oncogene product: in vitro and in vivo studies, *Cancer Res.*, 69:8987-8995, 2009.
Cao et al., Single-chain antibody-based immunotoxins targeting Her2/neu: design optimization and impact of affinity on antitumor efficacy and off-target toxicity, *Mol. Cancer Ther.*, 11:143-153, 2012.
Carter et al., Humanization of an anti-p185HER2 antibody for human cancer therapy, *Proc. Natl. Acad. Sci. U.S.A.*, 89:4285-4289, 1992.
Chowdhury and Lieberman, Death by a thousand cuts: granzyme pathways of programmed cell death, *Annu. Rev. Immunol.*, 26:389-420, 2008.
Cumber et al. (1992)
Fingl et al., In: *The Pharmacological Basis of Therapeutics*, 1:1, 1975.
Garrett and Arteaga, Resistance to HER2-directed antibodies and tyrosine kinase inhibitors: mechanisms and clinical implications, *Cancer Biol. Ther.*, 11:793-800, 2011.
Goyal et al., 2000
Gully et al., Antineoplastic effects of an Aurora B kinase inhibitor in breast cancer, *Mol. Cancer*, 9:42, 2010.
Harvey et al., 2004
Hilgeroth et al., The impact of the induction of multidrug resistance transporters in therapies by used drugs: recent studies, *Mini. Rev. Med. Chem.*, 12:1127-1134, 2012.
Hurvitz and Kakkar, The potential for trastuzumab emtansine in human epidermal growth factor receptor 2 positive metastatic breast cancer: latest evidence and ongoing studies, *Ther. Adv. Med. Oncol.*, 4:235-245, 2012.
Jerome et al., Recombinant human insulin-like growth factor binding protein 3 inhibits growth of human epidermal growth factor receptor-2-overexpressing breast tumors and potentiates herceptin activity in vivo, *Cancer Res.*, 66:7245-7252, 2006.
Kohl et al., 2003
Kovtun et al., Antibody-maytansinoid conjugates designed to bypass multidrug resistance, *Cancer Res.*, 70:2528-2537, 2010.
Kyte and Doolittle, *J. Mol. Biol.*, 157(1):105-132, 1982.
Liu et al., *Mol. Cancer Ther.*, 2:1341-1350, 2003.
Liu et al., Novel mechanism of lapatinib resistance in HER2-positive breast tumor cells: activation of AXL, *Cancer Res.*, 69:6871-6878, 2009.
Motyka et al., Mannose 6-phosphate/insulin-like growth factor II receptor is a death receptor for granzyme B during cytotoxic T cell-induced apoptosis, *Cell*, 103:491-500, 2000.
Murphy and Morris, Recent advances in novel targeted therapies for HER2-positive breast cancer, *Anticancer Drugs*, 23:765-776, 2012.
Nechushtan et al., 1997
Onda et al., *Cancer Res.*, 64:1419-1424, 2004.
Pack et al. (1992)
Plank et al., The influence of endosome-disruptive peptides on gene transfer using synthetic virus-like gene transfer systems, *J. Biol. Chem.*, 269:12918-12924, 1994.
Remington's Pharmaceutical Sciences, 18th Ed. Mack Printing Company, 1990.
Remington's Pharmaceutical Sciences, 18th Ed. Mack Printing Company, 1990, pp. 1289-1329.
Robinson et al., 1998.
Sambrook et al., 1989.
Skerra, 2001.
Szakacs et al., Targeting multidrug resistance in cancer, *Nat. Rev. Drug Discov.*, 5:219-234, 2006.
Thompson (ed.), 1994, The Cytokine Handbook, Academic Press, San Diego
Thorpe et al., *J. Natl. Cancer Inst.*, 79(5):1101-1112, 1987.
Trapani and Sutton, Granzyme B: pro-apoptotic, antiviral and antitumor functions, *Curr. Opin. Immunol.*, 15:533-543, 2003.

Turk et al., Characterization of a novel pH-sensitive peptide that enhances drug release from folate-targeted liposomes at endosomal pHs, *Biochim. Biophys. Acta,* 1559:56-68, 2002.

von Minckwitz et al., *Breast Cancer Res.,* 7:R616-626, 2005.

Wang et al., Different mechanisms for resistance to trastuzumab versus lapatinib in HER2-positive breast cancers—role of estrogen receptor and HER2 reactivation, *Breast Cancer Res.,* 13:R121, 2011.

Winkles J A: The TWEAK-Fn14 cytokine-receptor axis: discovery, biology and therapeutic targeting. *Nat Rev Drug Discov* 7:411-425 (2008).

Winthrop et al., *Clin. Cancer Res.,* 9:3845s-3853s, 2003.

Whitlow et al., 1993

Zhou et al.: Development and characterization of a potent immunoconjugate targeting the Fn14 receptor on solid tumor cells. *Mol Cancer Ther.* 10(7):1276-88, 2011.

What is claimed is:

1. A recombinant polypeptide comprising a Granzyme B (GrB) coding sequence at least 85% identical to SEQ ID NO: 1 wherein the GrB coding sequence comprises an amino acid substitution or deletion at the position corresponding to Cys 210, wherein the polypeptide is conjugated to or fused with a cell binding moiety.

2. The polypeptide of claim 1, wherein the polypeptide further comprises an amino acid sequence comprising a Cys, wherein the amino acid sequence is positioned C-terminally relative to the GrB coding sequence.

3. The polypeptide of claim 2, wherein the polypeptide further comprises the sequence SSCSGSA (SEQ ID NO: 12) positioned C-terminally relative to the GrB coding sequence.

4. The polypeptide of claim 1, wherein the polypeptide comprises an Ala substitution at the position corresponding to Cys 210.

5. The polypeptide of claim 1, wherein the polypeptide is conjugated to the cell binding moiety by a thioester linkage.

6. The polypeptide of claim 1, wherein the polypeptide fused with a cell binding moiety positioned C-terminally relative to the GrB coding sequence.

7. The polypeptide of claim 1, wherein the cell binding moiety is a VEGF, BLyS, an antibody or a cell-binding portion of any of the foregoing.

8. The polypeptide of claim 7, wherein the antibody is a monoclonal, chimeric antibody, Fab', Fab, F(ab')2, single domain antibody, Fv, or single chain Fv (scFv) antibody.

9. The polypeptide of claim 7, wherein the antibody is a human antibody, a humanized antibody or a deimmunized antibody.

10. The polypeptide of claim 7, wherein the antibody is a 15A8, ZME-018, ScFvMEL, cetuximab or trastuzumab antibody.

11. The polypeptide of claim 1, wherein the cell binding moiety binds to a protein, carbohydrate or lipid expressed on cancer cells.

12. The polypeptide of claim 1, wherein the cell binding moiety binds to GP240, 5T4, HER1, HER2, CD-33, CD-38, fltI, Flk-1, CEA, FGFR3, IGFBP2 or IGF-1R.

13. The polypeptide of claim 1, wherein the polypeptide or cell binding moiety is further conjugated to an imaging agent.

14. The polypeptide of claim 1, wherein the Granzyme B (GrB) coding sequence is at least 90% identical to SEQ ID NO: 1.

15. The polypeptide of claim 14, wherein the Granzyme B (GrB) coding sequence is at least 95% identical to SEQ ID NO: 1.

16. The polypeptide of claim 15, wherein the Granzyme B (GrB) coding sequence is identical to SEQ ID NO: 1.

* * * * *